United States Patent [19]
Dale et al.

[11] Patent Number: 6,063,386
[45] Date of Patent: May 16, 2000

[54] RECOMBINANT MULTIVALENT M PROTEIN VACCINE

[75] Inventors: James B. Dale, Memphis, Tenn.; James W. Lederer, Advance, N.C.

[73] Assignee: University of Tennessee Research Corporation, Knoxville, Tenn.

[21] Appl. No.: 08/937,271

[22] Filed: Sep. 15, 1997

Related U.S. Application Data

[63] Continuation-in-part of application No. 07/945,954, Sep. 16, 1992, abandoned.

[51] Int. Cl.$^7$ .................................................. A61K 39/09
[52] U.S. Cl. .................................... 424/244.1; 424/184.1; 424/185.1; 424/192.1; 424/244.1; 536/23.1; 536/23.4; 536/23.7; 435/320.1
[58] Field of Search .............................. 424/244.1, 184.1, 424/185.1, 192.1; 536/23.1, 23.7, 23.4; 435/320.1

[56] References Cited

U.S. PATENT DOCUMENTS

| | | | |
|---|---|---|---|
| 4,284,537 | 8/1981 | Beachey | 260/6 |
| 4,454,121 | 6/1984 | Beachey | 424/177 |
| 4,521,334 | 6/1985 | Beachey | 260/112.5 R |
| 4,597,967 | 7/1986 | Beachey | 424/88 |
| 4,705,684 | 11/1987 | Beachey | 424/88 |
| 4,784,948 | 11/1988 | Scott et al. | 435/68 |
| 4,919,930 | 4/1990 | Beachey et al. | 424/88 |
| 5,124,153 | 6/1992 | Beachey et al. | 424/93 |

FOREIGN PATENT DOCUMENTS

WO 94/06421  3/1994  WIPO.

OTHER PUBLICATIONS

Dale et al. 1986. J.Exp.Med. 163:113–122.
Podbielski et al. 1991. Med.Microbiol. Immunol. 180:213–227.
Beachey et al. 1987. J. Exp.Med. 166:647–656.
Miller et al. 1988. J. Biol. Chem. 263(12):S668–S673.
Beachey et al. 1986. J. Immunol. 135(6): 2287–2292.
Bronze et al. 1988.J.Exp.Med. 167: 1849–1859.
Dale et al. J. Immunol. 1993. 151(4):2188–2194.
Ada, *Fundamental Immunology*, 2$^{nd}$ Edition, Raven Press, New York, 1989, pp. 1010–1011.
Baird et al., "Epitopes Of Group A Streptococcal M Protein Shared With Antigens Of Articular Cartilage And Synovium," *The Journal Of Immunology* 146(9):3132–3137, 1991.
Beachey and Ofek, "Epithelial Cell Binding Of Group A Streptococci By Lipoteichoic Acid On Fimbriae Denuded Of M Protein," *The Journal Of Experimental Medicine* 143:759–771, 1976.
Beachey and Seyer, "Protective And Nonprotective Epitopes Of Chemically Synthesized Peptides Of The NH$_2$–Terminal Region Of Type 6 Streptococcal M Protein," *The Journal Of Immunology* 136(6):2287–2292, 1986.

Beachey and Seyer, *Seminars in Infectious Disease. vol. IV Bacterial Vaccines,* Thieme–Stratton Inc., New York, New York, 1982, Chapter Fifty–Seven, "Primary Structure And Immuno–Chemistry Of Group A Streptococcal M Proteins," pp. 401–410.
Beachey and Stollerman, "Mediation of Cytotoxic Effects of Streptococcal M Protein by Nontype–Specific Antibody in Human Sera," *The Journal of Clinical Investigation* 52:2563–2570, 1973.
Beachey and Stollerman, "Toxic Effects Of Steptococcal M Protein On Platelets And Polymorphonuclear Leukocytes In Human Blood," *The Journal Of Experimental Medicine* 134:351–365, 1971.
Beachey et al., "Human Immune Response To Immunization With a Structurally Defined Polypeptide Fragment Of Streptococcal M Protein," *J. Exp. Med.* 150:862–877, 1979.
Beachey et al., "Immunogenicity In Animals And Man Of A Structurally Defined Polypeptide Of Streptococcal M Protein," *Transactions Of The Association Of American Physicians,* vol. XCII:pp.346–354, 1979.
Beachey et al., "Opsonic Antibodies Evoked By Hybrid Peptide Copies Of Types 5 and 24 Streptococcal M Proteins Synthesized In Tandem," *J. Exp. Med.* 163: 1451–1458, 1986.
Beachey et al., "Peptic Digestion of Streptococcal M Protein. II. Extraction of M Antigen from Group A Streptococci With Pepsin," *Infection And Immunity* 9(5):891–896, 1974.
Beachey et al., "Primary Structure of Protective Antigens of Type 24 Streptococcal M Protein," *The Journal Of Biological Chemistry* 255(13):6284–6289, 1980.
Beachey et al., "Purification And Properties Of M Protein Extracted From Group A Streptococci With Pepsin: Covalent Structure Of The Amino Terminal Region Of Type 24 M Antigen," *The Journal Of Experimental Medicine* 145:1469–1483, 1977.
Beachey et al., "Repeating Covalent Structure and Protective Immunogenicity of Native and Synthetic Polypeptide Fragments of Type 24 Streptococcal M Protein," *The Journal Of Biological Chemistry* 258(21):13250–13257, 1983.
Beachey et al., "Repeating covalent structure of streptococcal M protein," *Proc. Natl. Acad. Sci. USA* 75(7):3163–3167, 1978.

(List continued on next page.)

*Primary Examiner*—James C. Housel
*Assistant Examiner*—Jennifer Graser
*Attorney, Agent, or Firm*—Seed Intellectual Property Law Group PLLC

[57] ABSTRACT

A recombinant multivalent hybrid protein vaccine against multiple serotypes of group A streptococci that may result in rheumatic fever. The vaccine can also evoke other protective antibodies of the mucosal type DNA sequences e.g. genes which encode the necessary amino acids that carry our the desired epitopes. A method of vaccination against streptococcal infections and compositions for carrying out the same.

47 Claims, 22 Drawing Sheets

OTHER PUBLICATIONS

Beachey et al., "Separation Of The Type Specific M Protein From Toxic Cross Reactive Agents Of Group A Streptococci," *Transactions Of The Association Of American Physicians.* Ninetieth Session vol. XC: pp. 390–400, 1977.

Beachey et al., "Type–specific protective immunity evoked by synthetic peptide of *streptococcus pyogenes* M Protein," *Nature (London) 292*:457–459, 1981.

Beall et al., "Sequencing emm–Specific PCR Porducts for Routine and Accurate typing of Group A Streptococci," *Journal Of Clinical Microbiology 34*(4):953–958, 1996.

Blenden et al., "Growth of *Listeria monocytogenes* in a Corn Silage Extract Medium," *American Journal Of Veterinary Research 29*(11):2237–2242, 1968.

Bricas et al., "Structure Et Synthese De La Subunite Peptide De La Paroi De Trois Bacteries Gram–Postif," *Peptides. Proceedings of the Eight European Peptide Symposium Sep. 1966, Noordwijk, Neth.,* North–Holland Publishing Company: Amsterdam, Neth. And Interscience Publishers Division, John Wiley and Sons, Inc., New York, 1967, 286–292 (+ *Biological Abstracts 50*(4):Abstract No. 20361, 1936).

Chou and Fasman, "Prediction of Protein Conformation," *Biochemistry 13*(2):222–245, 1974.

Cunningham and Beachey, "Peptic Digestion of Streptococcal M Protein. I. Effect of Digestion at Suboptimal pH upon the Biological and Immunochemical Properties of Purified M Protein Extracts," *Infection And Immunity 9*(2):244–248, 1974.

Cunningham et al., "Human And Murine Antibodies Cross–Reactive With Streptococcal M Protein And Myosin Recognize The Sequence Gln–Lys–Ser–Gln In M Protein," *The Journal Of Immunology 143*(8):2677–2683, 1989.

Dale, "Group A Streptococcal Vaccines," *New Vaccines And New Vaccine Technology 13*(1):227–243, 1999.

Dale, "Group A Streptococcal Vaccines," *Pediatric Annals 27*:301–308, 1998.

Dale, "Multivalent group A streptococcal vaccine designed to optimize the immunogenicity of six tandem M protein fragments," *Vaccine 17*:193–200, 1999.

Dale and Beachey, "Epitopes Of Streptococcal M Proteins Shared With Cardiac Myosin," *The Journal Of Experimental Medicine 162*:583–591, 1985.

Dale and Beachey, "Multiple, Heart–Cross–Reactive Epitopes Of Streptococcal M Proteins," *Journal Of Experimental Medicine 161*:113–122, 1985.

Dale and Beachey, "Sequence Of Myosin–Crossreactive Epitopes Of Streptococcal M Protein," *Journal Of Experimental Medicine 164*:1785–1790, 1986.

Dale and Beachey, "Localization Of Protective Epitopes Of The Amino Terminus Of Type 5 Streptococcal M Protein," *The Journal Of Experimental Medicine 163*:1191–1202, 1986.

Dale et al., "Recombinant, octavalent group A streptococcal M protein vaccine," *Vaccine 14*(10):944–948, 1996.

Dale et al., "Blastogenic Responses Of Human Lymphocytes To Structurally Defined Polypeptide Fragments Of Streptococcal M Protein," *The Journal Of Immunology 126*(4):1499–1505, 1981.

Dale et al., "Heterogeneity Of Type–Specific And Cross–Reactive Antigenic Determinants Within A Single M Protein Of Group A Streptococci," *The Journal Of Experimental Medicine 151*:1026–1038, 1980.

Dale et al., "Hyaluronate Capsule and Surface M Protein in Resistance to Opsonization of Group A Streptococci," *Infection And Immunity 64*(5):1495–1501, 1996.

Dale et al., "New protective antigen of group A streptococci," *J. Clin. Invest. 103*:1261–1268, 1999.

Dale et al., "Type–Specific Immunogenicity Of A Chemically Synthesized Peptide Fragment Of Type 5 Streptococcal M Protein," *The Journal Of Experimental Medicine 158*:1727–1732, 1983.

Dixit et al., "Covalent Structure of Collagen: Amino Acid Sequence of α1–CB6A of Chick Skin Collagen," *Biochemistry 14*(9):1933–1938, 1975.

Edman and Begg, "A Protein Sequentor," *European J. Biochem. 1*:80–91, 1967.

Fischetti et al., "Surface Proteins from Gram–Positive Cocci Share Unique Structural Features," in Orefici (ed.), *New Perspectives on Streptococci and Streptococcal Infections. Proceedings of the XI Lancefield International Symposium on Streptococci and Streptococcal Diseases,* Siena, Italy, Sep. 10–14, 1990, Gustav Fischer verlag, Stuttgart, Jena, New York, 1992, pp. 165–167.

Fischetti, "Streptococcal M Protein," *Scientific American :* pp. 58–65, 1991.

Freimer and McCarty, "Rheumatic Fever," *Scientific American 213*(6):67–74, 1965.

Gibbons et al., "Studies of Individual Amino Acid Residues of the Decapeptide Tyrocidine A by Proton Double–Resonance Difference Spectroscopy in the Correlation Mode," *Biochemistry 14*(2):420–437, 1975.

Goldsberg et al., "Serological Demonstration of H–Y (Male) Antigen on Mouse Sperm," *Nature 232*:478–480, 1971.

Hollingshead et al., "Complete Nucleotide Sequence of Type 6 M Protein of the Group A Streptococcus," *The Journal Of Biological Chemistry 261*(4):1677–1686, 1986.

Hopp and Woods, "Prediction of protein antigenic determinants from amino acid sequences," *Proc. Natl. Acad. Sci. USA 78*(6):3824–3828, 1981.

Jones et al., "Differential Effects Of Antibodies To Lyt–2 And L3 T4 On Cytolysis By Cloned, Ia–Restricted T Cells Expressing Both Proteins," *The Journal Of Immunology 139*(2):380–384, 1987.

Kang, "Studies on the Location of Intermolecular Cross–Links in Collagen. Isolation of a CNBr Peptide Containing δ–Hydroxylysinonorleucine," *Biochemistry 11*(10):1828–1835, 1972.

Kang and Gross, "Amino Acid Sequence of Cyanogen Bromide Peptides from the Amino–Terminal Region of Chick Skin Collagen," *Biochemistry 9*(4):796–804, 1970.

Kaplan et al., "Group A Streptococcal Serotypes Isolated from Patients and Sibling Contacts During the Resurgence of Rheumatic Fever in the United States in the Mid–1980s," *The Journal Of Infectious Diseases 159*(1):101–103, 1989.

Koch et al., "Purification And Structural Analysis Of Streptolysin S (SLS)," *Federation Proceedings 42*(7): p. 1810, Abstract No. 309, 1983.

Kraus et al., "Identification Of An Epitope Of Type 1 Streptococcal M Protein That Is Shared With A 43–kDa Protein Of Human Myocardium And Renal Glomeruli," *The Journal Of Immunology 145*(12):4089–4093, 1990.

Kraus et al., "Sequence And Type–Specific Immunogenicity Of The Amino–Terminal Region Of Type 1 Streptococcal M Protein," *The Journal Of Immunology 139*(9):3084–3090, 1987.

Lancefield, "Persistence Of Type–Specific Antibodies In Man Following Infection With Group A Streptococci," *J. Exp. Med.* 110:271–292, 1959.

Laver et al., "Antigenic drift in type A influenza virus: Peptide mapping and antigenic analysis of A/PR/8/34 (HON1) variants selected with monoclonal antibodies," *Proc. Natl. Acad. Sci. USA* 76(3):1425–1429, 1979.

Lockey, "Urticaria of Unknown Origin," *Hospital Practice*: pp. 49–57, 1979.

Manjula and Fischetti, "Tropomyosin–Like Seven Residue Periodicity In Three Immunologically Distinct Streptococcal M Proteins And Its Implications For The Antiphagocytic Property Of The Molecule," *J. Exp. Med.* 151:695–708, 1980.

Miller et al., "Conservation of Protective and Nonprotective Epitopes in M Proteins of Group A Streptococci," *Infection And Immunity* 56(8):2198–2204, 1988.

Mouw et al., "Molecular Evolution of Streptococcal M Protein: Cloning and Nucleotide Sequence of the Type 24 M Protein Gene and Relation to Other Genes of *Streptococcus pyogenes*," *Journal Of Bacteriology* 170(2):676–684, 1988.

Phillips, Jr. et al., "Streptococcal M protein: α–Helical coiled–coil structure and arrangement on the cell surface," *Proc. Natl. Acad. Sci. USA* 78(8):4689–4693, 1981.

Rijn et al., "Group A Streptococcal Antigens Cross–Reactive With Mycocardium," *The Journal of Experimental Medicine* 146:579–599, 1977.

Robbins et al., "*Streptococcus pyogenes* Type 12 M Protein Gene Regulation by Upstream Sequences," *Journal Of Bacteriology* 169(12):5633–5640, 1987.

Sargent et al., "Sequence Of Protective Epitopes Of Streptococcal M Proteins Shared With Cardiac Sarcolemmal Membranes," *The Journal Of Immunology* 139(4):1285–1290, 1987.

Seyer and Kang, "Covalent Structure of Collagen: Amino Acid Sequence of Cyanogen Bromide Peptides from the Amino–Terminal Segment of Type III Collagen of Human Liver," *Biochemistry* 16(6):1158–1164, 1977.

Seyer et al., "Primary Structural Similarities Between Types 5 And 24 M Proteins Of *Streptococcus pyogenes*," *Biochemical And Biophysical Research Communications* 92(2):546–553, 1980.

Smithies et al., "Quantitative Procedures for Use with the Edman–Begg Sequenator. Partial Sequences of Two Unusual Immunoglobulin Light Chains, Rzf and Sac," *Biochemistry* 10(26):4912–4921, 1971.

Vashishtha et al., "Reactivity of Antisera to Peptides Corresponding to the C–repeat Region of Streptococcal M Protein with Mammalian Coiled–Coil Proteins," *Abstracts Of The 91$^{st}$ General Meeting of the Society for Microbiology 1991*:p. 129, Abstract No. E–66, 1991.

Weigent et al., "Induction of Human Gamma Interferon by Structurally Defined Polypeptide Fragments of Group A Streptococcal M Protein," *Infection And Immunity* 43(1):122–126, 1984.

Wistedt et al., "Identification of a plasminogen–binding motif in PAM, a bacterial surface protein," *Molecular Microbiology* 18(3): 569–578, 1995.

Wittner and Fox, "Homologous and Heterologous Protection of Mice with Group A Streptococcal M Protein Vaccines," *Infection and Immunity* 15(1):104–108, 1977.

M24-M5-M6 RECOMBINANT HYBRID

| | |
|---|---|
| ATG GTC GCG ACT AGG TCT CAG ACA GAT ACT CTG GAA AAA GTA CAA GAA<br>Met Val Ala Thr Arg Ser Gln Thr Asp Thr Leu Glu Lys Val Gln Glu<br>1                5                    10                  15<br>M24------------------------------------------------ | 48 |
| CGT GCT GAC AAG TTT GAG ATA GAA AAC AAT ACG TTA AAA CTT AAG AAT<br>Arg Ala Asp Lys Phe Glu Ile Glu Asn Asn Thr Leu Lys Leu Lys Asn<br>                    20                    25                  30 | 96 |
| AGT GAC TTA AGT TTT AAT AAT AAA GCG TTA AAA GAT CAT AAT GAT GAG<br>Ser Asp Leu Ser Phe Asn Asn Lys Ala Leu Lys Asp His Asn Asp Glu<br>           35                    40                    45 | 144 |
| TTA ACT GAA GAG TTG AGT AAT GCT AAA GAG AAA CTA CGT AAA AAT GAT<br>Leu Thr Glu Glu Leu Ser Asn Ala Lys Glu Lys Leu Arg Lys Asn Asp<br>     50                    55                    60 | 192 |
| AAA TCA CTA TCT GAA AAA GCT AGT AAA ATT CAA GAA TTA GAG GCA CGT<br>Lys Ser Leu Ser Glu Lys Ala Ser Lys Ile Gln Glu Leu Glu Ala Arg<br>65                70                    75                  80 | 240 |
| AAG GCT GAT CTT GAA AAA GCA TTA GAA GGC GCA ATG AAT TTT TCA ACA<br>Lys Ala Asp Leu Glu Lys Ala Leu Glu Gly Ala Met Asn Phe Ser Thr<br>                    85                    90                  95 | 288 |
| GCG GAT TCA GCT AAA ATC AAA ACC TTA GAA GCA GAG AAA GCT GCT TTA<br>Ala Asp Ser Ala Lys Ile Lys Thr Leu Glu Ala Glu Lys Ala Ala Leu<br>                    100                 105               110 | 336 |
| GCG GCA CGT AAG GCT GAT CTT GAA AAA GCA TTA GAA GGC GCA ATG AAC<br>Ala Ala Arg Lys Ala Asp Leu Glu Lys Ala Leu Glu Gly Ala Met Asn<br>            115                    120                 125 | 384 |
| TTT TCA ACA GCG GAT TCA GCT AAA ATC AAA ACC TTA GAA GCA GAG AAA<br>Phe Ser Thr Ala Asp Ser Ala Lys Ile Lys Thr Leu Glu Ala Glu Lys<br>     130                    135                    140 | 432 |
| GCT GCT TTA GAG GCA CGC CAG GCT GAA CTT GAA AAA GCA TTA GAA GGC<br>Ala Ala Leu Glu Ala Arg Gln Ala Glu Leu Glu Lys Ala Leu Glu Gly<br>145                150                    155               160 | 480 |

*Fig. 1A*

```
GCA ATG AAT TTT TCA ACA GCG GAT TCA GCT AAA ATC AAA ACC TTA GAA    528
Ala Met Asn Phe Ser Thr Ala Asp Ser Ala Lys Ile Lys Thr Leu Glu
            165                 170                 175

GCA GAG AAA GCT GCT TTA GCG GCA CGT AAG GCT GAT CTT GAA AAA GCA    576
Ala Glu Lys Ala Ala Leu Ala Ala Arg Lys Ala Asp Leu Glu Lys Ala
            180                 185                 190

TTA GAA GGC GCA ATG AAC TTT TCA ACA GCG GAT TCA GCT AAA ATC AAA    624
Leu Glu Gly Ala Met Asn Phe Ser Thr Ala Asp Ser Ala Lys Ile Lys
            195                 200                 205

ACC TTA GAA GCA GAG AAA GCT GCT TTA GAG GCA CGC CAG GCT GAA CTT    672
Thr Leu Glu Ala Glu Lys Ala Ala Leu Glu Ala Arg Gln Ala Glu Leu
    210                 215                 220

GAA AAA GCA TTA GAA GGC GCA ATG AAT TTT TCA ACA GCG GAT TCA GCT    720
Glu Lys Ala Leu Glu Gly Ala Met Asn Phe Ser Thr Ala Asp Ser Ala
225                 230                 235                 240

AAA ATC AAA ACC TTA GAA GCA GAG AAA GCT GCT TTG GAG GCA GAG AAA    768
Lys Ile Lys Thr Leu Glu Ala Glu Lys Ala Ala Leu Glu Ala Glu Lys
            245                 250                 255

GCT GAT CTT GAA GGA TCC GCC GTG ACT AGG GGT ACA ATA AAT GAC CCG    816
Ala Asp Leu Glu Gly Ser Ala Val Thr Arg Gly Thr Ile Asn Asp Pro
            260                 265                 270
                   Bam H1 M5------------------------

CAA GTC GAC AGA GTG TTT CCT AGG GGG ACG GTA GAA AAC CCG GAC        861
Gln Val Asp Arg Val Phe Pro Arg Gly Thr Val Glu Asn Pro Asp
            275                 280                 285
---- Sal I  M6----------------
```

*Fig. 1B*

M24-M5-M6-M19 RECOMBINANT HYBRID

```
ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15
M24------------------------------------

CGT GCT GAC AAG TTT GAG ATA GAA AAC AAT ACG TTA AAA CTT AAG AAT        96
Arg Ala Asp Lys Phe Glu Ile Glu Asn Asn Thr Leu Lys Leu Lys Asn
                 20                  25                  30

AGT GAC TTA AGT TTT AAT AAT AAA GCG TTA AAA GAT CAT AAT GAT GAG       144
Ser Asp Leu Ser Phe Asn Asn Lys Ala Leu Lys Asp His Asn Asp Glu
             35                  40                  45

TTA ACT GAA GAG TTG AGT AAT GCT AAA GAG AAA CTA CGT AAA AAT GAT       192
Leu Thr Glu Glu Leu Ser Asn Ala Lys Glu Lys Leu Arg Lys Asn Asp
         50                  55                  60

AAA TCA CTA TCT GAA AAA GCT AGT AAA AAT CAA GAA TTA GAG GCA CGT       240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA       288
Lys Ala Asp Leu Glu Lys Ala Leu Glu Gly Ala Met Asn Phe Ser Thr
                 85                  90                  95
                                                      Bam H1--M5-

GCG GAT TCA GCT AAA ATC AAA ACC TTA GAA GCA GAG AAA GCT GAT CTT       336
Ala Asp Ser Ala Lys Ile Lys Thr Leu Glu Ala Glu Lys Ala Asp Leu
             100                 105                 110
----------------

GAA GGA TCC GCC GTG ACT AGG GGT ACA ATA AAT GAC CCG CAA AGA GCA       384
Glu Gly Ser Ala Val Thr Arg Gly Thr Ile Asn Asp Pro Gln Arg Ala
         115                 120                 125

AAA GAA GCT CTT GAC AAG TAT GAG CTA GAA AAC CAT GAC TTA AAA ACT       432
Lys Glu Ala Leu Asp Lys Tyr Glu Leu Glu Asn His Asp Leu Lys Thr
     130                 135                 140
```

*Fig. 4A*

```
AAG AAT GAA GGG TTA AAA ACT GAG AAT GAA GGG TTA AAA ACT GAG AAT      480
Lys Asn Glu Gly Leu Lys Thr Glu Asn Glu Gly Leu Lys Thr Glu Asn
145             150             155             160
                                    Sal 1---M6-----------------

GAA GGG TTA AAA ACT GAG AAT GAA GGG TTA AAA ACT GAG GTC GAC AGA      528
Glu Gly Leu Lys Thr Glu Asn Glu Gly Leu Lys Thr Glu Val Asp Arg
            165             170             175

GTG TTT CCT AGG GGG ACG GTA GAA AAC CCG GAC AAA GCA CGA GAA CTT      576
Val Phe Pro Arg Gly Thr Val Glu Asn Pro Asp Lys Ala Arg Glu Leu
            180             185             190
                                                    Ncol--

CTT AAC AAG TAT GAC GTA GAG AAC TCT ATG TTA CAA GCT AAT AAT GAC      624
Leu Asn Lys Tyr Asp Val Glu Asn Ser Met Leu Gln Ala Asn Asn Asp
        195             200             205
M19------------------------

AAG TTA CCA TGG AGA GTG CGT TAT ACT AGG CAT ACG CCA GAA GAT AAG      672
Lys Leu Pro Trp Arg Val Arg Tyr Thr Arg His Thr Pro Glu Asp Lys
    210             215             220

CTA AAA AAA ATT ATT GAC GAT CTT GAC GCA AAA GAA CAT GAA TTA CAA      720
Leu Lys Lys Ile Ile Asp Asp Leu Asp Ala Lys Glu His Glu Leu Gln
225             230             235             240

CAA CAG AAT GAG AAG TTA TCT                                          741
Gln Gln Asn Glu Lys Leu Ser
            245
```

*Fig. 4B*

M24-M5-M6-M19 (LINKER VARIANT)

```
ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15
M24--------------

CGT GCT GAC AAG TTT GAG ATA GAA AAC AAT ACG TTA AAA CTT AAG AAT        96
Arg Ala Asp Lys Phe Glu Ile Glu Asn Asn Thr Leu Lys Leu Lys Asn
                20                  25                  30

AGT GAC TTA AGT TTT AAT AAT AAA GCG TTA AAA GAT CAT AAT GAT GAG       144
Ser Asp Leu Ser Phe Asn Asn Lys Ala Leu Lys Asp His Asn Asp Glu
                35                  40                  45

TTA ACT GAA GAG TTG AGT AAT GCT AAA GAG AAA CTA CGT AAA AAT GAT       192
Leu Thr Glu Glu Leu Ser Asn Ala Lys Glu Lys Leu Arg Lys Asn Asp
        50                  55                  60

AAA TCA CTA TCT GAA AAA GCT AGT AAA AAT CAA GAA TTA GAG GCA CGT       240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA       288
Lys Ala Asp Leu Glu Lys Ala Leu Glu Gly Ala Met Asn Phe Ser Thr
                85                  90                  95

GCG GAT TCA GCT AAA ATC AAA ACC TTA GAA GCA GAG AAA GCT GAT CTT       336
Ala Asp Ser Ala Lys Ile Lys Thr Leu Glu Ala Glu Lys Ala Asp Leu
                100                 105                 110

GAA GGA TCC CCA GGA AAC CCA GCT GTT CCA GGA TCC GCC GTG ACT AGG       384
Glu Gly Ser Pro Gly Asn Pro Ala Val Pro Gly Ser Ala Val Thr Arg
                115                 120                 125
        Bam H1--LINKER--------------------Bam H1--M5-------------

GGT ACA ATA AAT GAC CCG CAA AGA GCA AAA GAA GCT CTT GAC AAG TAT       432
Gly Thr Ile Asn Asp Pro Gln Arg Ala Lys Glu Ala Leu Asp Lys Tyr
        130                 135                 140
------------
```

*Fig. 6A*

```
GAG CTA GAA AAC CAT GAC TTA AAA ACT AAG AAT GAA GGG TTA AAA ACT      480
Glu Leu Glu Asn His Asp Leu Lys Thr Lys Asn Glu Gly Leu Lys Thr
145                 150                 155                 160

GAG AAT GAA GGG TTA AAA ACT GAG AAT GAA GGG TTA AAA ACT GAG AAT      528
Glu Asn Glu Gly Leu Lys Thr Glu Asn Glu Gly Leu Lys Thr Glu Asn
                    165                 170                 175

GAA GGG TTA AAA ACT GAG GTC GAC CCA GGA AAC CCA GCT GTT CCA GTC      576
Glu Gly Leu Lys Thr Glu Val Asp Pro Gly Asn Pro Ala Val Pro Val
                180                 185                 190
                            SalI----LINKER---------------------SalI

GAC AGA GTG TTT CCT AGG GGG ACG GTA GAA AAC CCG GAC AAA GCA CGA      624
Asp Arg Val Phe Pro Arg Gly Thr Val Glu Asn Pro Asp Lys Ala Arg
        195                 200                 205
-----M6-----------------

GAA CTT CTT AAC AAG TAT GAC GTA GAG AAC TCT ATG TTA CAA GCT AAT      672
Glu Leu Leu Asn Lys Tyr Asp Val Glu Asn Ser Met Leu Gln Ala Asn
    210                 215                 220

AAT GAC AAG TTA CCA TGG CCA GGA AAC CCA GCT GTT CCA CCA TGG AGA      720
Asn Asp Lys Leu Pro Trp Pro Gly Asn Pro Ala Val Pro Pro Trp Arg
225                 230                 235                 240
                NcoI----LINKER---------------------NcoI---M19

GTG CGT TAT ACT AGG CAT ACG CCA GAA GAT AAG CTA AAA AAA ATT ATT      768
Val Arg Tyr Thr Arg His Thr Pro Glu Asp Lys Leu Lys Lys Ile Ile
                245                 250                 255
---------------

GAC GAT CTT GAC GCA AAA GAA CAT GAA TTA CAA CAA CAG AAT GAG AAG      816
Asp Asp Leu Asp Ala Lys Glu His Glu Leu Gln Gln Gln Asn Glu Lys
                260                 265                 270

TTA TCT                                                              822
Leu Ser
```

*Fig. 6B*

M24-M5-M6-M19 (SUBUNIT VARIANT)

```
ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1           5                  10                  15
M24(A)-------------------------------------------------

GTC GCG ACT AGG TCT CAG ACA GAT ACT CTG GAA AAA GTA CAA GAA GTC        96
Val Ala Thr Arg Ser Gln Thr Asp Thr Leu Glu Lys Val Gln Glu Val
            20                  25                  30
M24(B)---------------------------------------------------M24(C)

GCG ACT AGG TCT CAG ACA GAT ACT CTG GAA AAA GTA CAA GAA GGA TCC       144
Ala Thr Arg Ser Gln Thr Asp Thr Leu Glu Lys Val Gln Glu Gly Ser
                35                  40                  45
-----------------------------------------------------BamH1--

GCC GTG ACT AGG GGT ACA ATA AAT GAC CCG CAA AGA GCA AAA GAA GCC       192
Ala Val Thr Arg Gly Thr Ile Asn Asp Pro Gln Arg Ala Lys Glu Ala
     50                  55                  60
M5(A)-------------------------------------------------M5(B)

GTG ACT AGG GGT ACA ATA AAT GAC CCG CAA AGA GCA AAA GAA GCC GTG       240
Val Thr Arg Gly Thr Ile Asn Asp Pro Gln Arg Ala Lys Glu Ala Val
 65                  70                  75                  80
-----------------------------------------------------M5(C)--

ACT AGG GGT ACA ATA AAT GAC CCG CAA AGA GCA AAA GAA GTC GAC AGA       288
Thr Arg Gly Thr Ile Asn Asp Pro Gln Arg Ala Lys Glu Val Asp Arg
                 85                  90                  95
---------------------------------------------------SalI----M6(A)

GTG TTT CCT AGG GGG ACG GTA GAA AAC CCG GAC AAA GCA CGA AGA GTG       336
Val Phe Pro Arg Gly Thr Val Glu Asn Pro Asp Lys Ala Arg Arg Val
                100                 105                 110
-----------------------------------------------------M6(B)--

TTT CCT AGG GGG ACG GTA GAA AAC CCG GAC AAA GCA CGA AGA GTG TTT       384
Phe Pro Arg Gly Thr Val Glu Asn Pro Asp Lys Ala Arg Arg Val Phe
            115                 120                 125
------------------------------------------------------M6(C)------
```

*Fig. 7A*

```
CCT AGG GGG ACG GTA GAA AAC CCG GAC AAA GCA CGA CCA TGG AGA GTG      432
Pro Arg Gly Thr Val Glu Asn Pro Asp Lys Ala Arg Pro Trp Arg Val
    130                 135                 140
-----------------------------------------------------Ncol----M19(A)-

CGT TAT ACT AGG CAT ACG CCA GAA GAT AAG CTA AAA AAA AGA GTG CGT      480
Arg Tyr Thr Arg His Thr Pro Glu Asp Lys Leu Lys Lys Arg Val Arg
145                 150                 155                 160
-------------------------------------------------------M19(B)-----

TAT ACT AGG CAT ACG CCA GAA GAT AAG CTA AAA AAA AGA GTG CGT TAT      528
Tyr Thr Arg His Thr Pro Glu Asp Lys Leu Lys Lys Arg Val Arg Tyr
            165                 170                 175
---------------------------------------------------M19(C)---------

ACT AGG CAT ACG CCA GAA GAT AAG CTA AAA AAA                          561
Thr Arg His Thr Pro Glu Asp Lys Leu Lys Lys
            180                 185
-------------------------------------------
```

*Fig. 7B*

M24-M5-M6-M19-COOH-TERMINUS

| | |
|---|---|
| ATG GTC GCG ACT AGG TCT CAG ACA GAT ACT CTG GAA AAA GTA CAA GAA<br>Met Val Ala Thr Arg Ser Gln Thr Asp Thr Leu Glu Lys Val Gln Glu<br>1              5              10             15<br>   M24------------------------------------------------------------ | 48 |
| GGA TCC GGA TCC GCC GTG ACT AGG GGT ACA ATA AAT GAC CCG CAA AGA<br>Gly Ser Gly Ser Ala Val Thr Arg Gly Thr Ile Asn Asp Pro Gln Arg<br>                20              25             30<br>-BamH1----------M5--------------------------------------------- | 96 |
| GCA AAA GAA GTC GAC AGA GTG TTT CCT AGG GGG ACG GTA GAA AAC CCG<br>Ala Lys Glu Val Asp Arg Val Phe Pro Arg Gly Thr Val Glu Asn Pro<br>        35              40             45<br>--------------SalI----M6--------------------------------------- | 144 |
| GAC AAA GCA CGA CCA TGG AGA GTG CGT TAT ACT AGG CAT ACG CCA GAA<br>Asp Lys Ala Arg Pro Trp Arg Val Arg Tyr Thr Arg His Thr Pro Glu<br>        50              55             60<br>------------------NcoI----M19---------------------------------- | 192 |
| GAT AAG CTA AAA AAA CTG CAG AAC AAA ATT TCA GAC GCA AGC CGT AAG<br>Asp Lys Leu Lys Lys Leu Gln Asn Lys Ile Ser Asp Ala Ser Arg Lys<br>        65              70             75            80<br>---------------------Pst1----M5 COOH HALF--------------------- | 240 |
| GGT CTT CGT CGT GAC TTA GAC GCA TCG CGT GAA GCT AAG AAG CAA TTA<br>Gly Leu Arg Arg Asp Leu Asp Ala Ser Arg Glu Ala Lys Lys Gln Leu<br>                    85             90            95<br>-----------TO END | 288 |
| GAA GCT GAA CAC CAA AAA CTT GAA GAA CAA AAC AAG ATT TCA GAA GCA<br>Glu Ala Glu His Gln Lys Leu Glu Glu Gln Asn Lys Ile Ser Glu Ala<br>                100            105          110 | 336 |
| AGT CGC AAA GGC CTT CGC CGT GAT TTA GAC GCA TCA CGT GAA GCT AAG<br>Ser Arg Lys Gly Leu Arg Arg Asp Leu Asp Ala Ser Arg Glu Ala Lys<br>          115             120            125 | 384 |
| AAG CAA TTA GAA GCT GAA CAA CAA AAA CTT GAA GAA CAA AAC AAG ATT<br>Lys Gln Leu Glu Ala Glu Gln Gln Lys Leu Glu Glu Gln Asn Lys Ile<br>        130             135            140 | 432 |

*Fig. 8A*

```
TCA GAA GCA AGT CGC AAA GGC CTT CGC CGT GAT TTA GAC GCA TCA CGT         480
Ser Glu Ala Ser Arg Lys Gly Leu Arg Arg Asp Leu Asp Ala Ser Arg
145                 150                 155                 160

GAA GCT AAG AAA CAA GTT GAA AAA GCT TTA GAA GAA GCA AAC AGC AAA         528
Glu Ala Lys Lys Gln Val Glu Lys Ala Leu Glu Glu Ala Asn Ser Lys
                165                 170                 175

TTA GCT GCT CTT GAA AAA CTT AAC AAA GAG CTT GAA GAA AGC AAG AAA         576
Leu Ala Ala Leu Glu Lys Leu Asn Lys Glu Leu Glu Glu Ser Lys Lys
            180                 185                 190

TTA ACA GAA AAA GAA AAA GCT GAG CTA CAA GCA AAA CTT GAA GCA GAA         624
Leu Thr Glu Lys Glu Lys Ala Glu Leu Gln Ala Lys Leu Glu Ala Glu
        195                 200                 205

GCA AAA GCA CTC AAA GAA CAA TTA GCA AAA CAA GCT GAA GAA CTT GCA         672
Ala Lys Ala Leu Lys Glu Gln Leu Ala Lys Gln Ala Glu Glu Leu Ala
    210                 215                 220

AAA CTA AGA GCT GGA AAA GCA TCA GAC TCA CAA ACC CCT GAT ACA AAA         720
Lys Leu Arg Ala Gly Lys Ala Ser Asp Ser Gln Thr Pro Asp Thr Lys
225                 230                 235                 240

CCA GGA AAC AAA GCT GTT CCA GGT AAA GGT CAA GCA CCA CAA GCA GGT         768
Pro Gly Asn Lys Ala Val Pro Gly Lys Gly Gln Ala Pro Gln Ala Gly
                245                 250                 255

ACA AAA CCA AAC CAA AAC AAA GCA CCA ATG AAG GAA ACT AAG AGA CAG         816
Thr Lys Pro Asn Gln Asn Lys Ala Pro Met Lys Glu Thr Lys Arg Gln
            260                 265                 270

TTA CCA TCA ACA GGT GAA ACA GCT AAC CCA TTC TTC ACA GCG GCA GCC         864
Leu Pro Ser Thr Gly Glu Thr Ala Asn Pro Phe Phe Thr Ala Ala Ala
        275                 280                 285

CTT ACT GTT ATG GCA ACA GCT GGA GTA GCA GCA GTT GTA AAA CGC AAA         912
Leu Thr Val Met Ala Thr Ala Gly Val Ala Ala Val Val Lys Arg Lys
    290                 295                 300

GAA GAA AAT TAA                                                         924
Glu Glu Asn ***
305
```

*Fig. 8B*

M19-M6-M5-M24 RECOMBINANT HYBRID

```
ATG AGA GTG CGT TAT ACT AGG CAT ACG CCA GAA GAT AAG CTA AAA AAA          48
Met Arg Val Arg Tyr Thr Arg His Thr Pro Glu Asp Lys Leu Lys Lys
 1               5                  10                  15
     M19----------------------

ATT ATT GAC GAT CTT GAC GCA AAA GAA CAT GAA TTA CAA CAA CAG AAT          96
Ile Ile Asp Asp Leu Asp Ala Lys Glu His Glu Leu Gln Gln Gln Asn
                 20                  25                  30

GAG AAG TTA TCT GGA TCC AGA GTG TTT CCT AGG GGG ACG GTA GAA AAC         144
Glu Lys Leu Ser Gly Ser Arg Val Phe Pro Arg Gly Thr Val Glu Asn
         35                  40                  45
             Bam H1-M6---------------

CCG GAC AAA GCA CGA GAA CTT CTT AAC AAG TAT GAC GTA GAG AAC TCT         192
Pro Asp Lys Ala Arg Glu Leu Leu Asn Lys Tyr Asp Val Glu Asn Ser
     50                  55                  60

ATG TTA CAA GCT AAT AAT GAC AAC TTA GTC GAC GCC GTG ACT AGG GGT         240
Met Leu Gln Ala Asn Asn Asp Asn Leu Val Asp Ala Val Thr Arg Gly
 65                  70                  75                  80
                                         SalI----M5----------------

ACA ATA AAT GAC CCG CAA AGA GCA AAA GAA GCT CTT GAC AAG TAT GAG         288
Thr Ile Asn Asp Pro Gln Arg Ala Lys Glu Ala Leu Asp Lys Tyr Glu
                 85                  90                  95
----------

CTA GAA AAC CAT GAC TTA AAA ACT AAG AAT GAA GGG TTA AAA ACT GAG         336
Leu Glu Asn His Asp Leu Lys Thr Lys Asn Glu Gly Leu Lys Thr Glu
                100                 105                 110

AAT GAA GGG TTA AAA ACT GAG AAT GAA GGG TTA AAA ACT GAG AAT GAA         384
Asn Glu Gly Leu Lys Thr Glu Asn Glu Gly Leu Lys Thr Glu Asn Glu
        115                 120                 125
```

Fig. 9A

```
GGG TTA AAA ACT GAG CCA TGG GTC GCG ACT AGG TCT CAG ACA GAT ACT      432
Gly Leu Lys Thr Glu Pro Trp Val Ala Thr Arg Ser Gln Thr Asp Thr
    130             135                 140
             NcoI----M24------------------------

CTG GAA AAA GTA CAA GAA CGT GCT GAC AAG TTT GAG ATA GAA AAC AAT      480
Leu Glu Lys Val Gln Glu Arg Ala Asp Lys Phe Glu Ile Glu Asn Asn
145             150                 155                 160

ACG TTA AAA CTT AAG AAT AGT GAC TTA AGT TTT AAT AAT AAA GCG TTA      528
Thr Leu Lys Leu Lys Asn Ser Asp Leu Ser Phe Asn Asn Lys Ala Leu
                165                 170                 175

AAA GAT CAT AAT GAT GAG TTA ACT GAA GAG TTG AGT AAT GCT AAA GAG      576
Lys Asp His Asn Asp Glu Leu Thr Glu Glu Leu Ser Asn Ala Lys Glu
            180                 185                 190

AAA CTA CGT AAA AAT GAT AAA TCA CTA TCT GAA AAA GCT AGT AAA AAT      624
Lys Leu Arg Lys Asn Asp Lys Ser Leu Ser Glu Lys Ala Ser Lys Asn
        195                 200                 205

CAA GAA TTA GAG GCA CGT AAG GCT GAT CTT GAA AAA GCA TTA GAA GGC      672
Gln Glu Leu Glu Ala Arg Lys Ala Asp Leu Glu Lys Ala Leu Glu Gly
    210             215                 220

GCA ATG AAT TTT TCA ACA GCG GAT TCA GCT AAA ATC AAA ACC TTA GAA      720
Ala Met Asn Phe Ser Thr Ala Asp Ser Ala Lys Ile Lys Thr Leu Glu
225             230                 235                 240

GCA GAG AAA GCT GAT CTT GAA                                          741
Ala Glu Lys Ala Asp Leu Glu
            245
```

*Fig. 9B*

M24-M5 DIVALENT HYBRID

```
ATG GTC GCG ACT AGG TCT CAG ACA GAT ACT CTG GAA AAA GTA CAA GAA     48
Met Val Ala Thr Arg Ser Gln Thr Asp Thr Leu Glu Lys Val Gln Glu
 1               5                  10                  15
    M24------------------------

CGT GCT GAC AAG TTT GAG ATA GAA AAC AAT ACG TTA AAA CTT AAG AAT     96
Arg Ala Asp Lys Phe Glu Ile Glu Asn Asn Thr Leu Lys Leu Lys Asn
                20                  25                  30

AGT GAC TTA AGT TTT AAT AAT AAA GCG TTA AAA GAT CAT AAT GAT GAG    144
Ser Asp Leu Ser Phe Asn Asn Lys Ala Leu Lys Asp His Asn Asp Glu
            35                  40                  45

TTA ACT GAA GAG TTG AGT AAT GCT AAA GAG AAA CTA CGT AAA AAT GAT    192
Leu Thr Glu Glu Leu Ser Asn Ala Lys Glu Lys Leu Arg Lys Asn Asp
        50                  55                  60

AAA TCA CTA TCT GAA AAA GCT AGT AAA AAT CAA GAA TTA GAG GCA CGT    240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA    288
Lys Ala Asp Leu Glu Lys Ala Leu Glu Gly Ala Met Asn Phe Ser Thr
                85                  90                  95

GCG GAT TCA GCT AAA ATC AAA ACC TTA GAA GCA GAG AAA GCT GAT CTT    336
Ala Asp Ser Ala Lys Ile Lys Thr Leu Glu Ala Glu Lys Ala Asp Leu
            100                 105                 110

GAA GGA TCC GCC GTG ACT AGG GGT ACA ATA AAT GAC CCG CAA AGA GCA    384
Glu Gly Ser Ala Val Thr Arg Gly Thr Ile Asn Asp Pro Gln Arg Ala
        115                 120                 125
    BamH1---M5-------------

AAA GAA GCT CTT GAC AAG TAT GAG CTA GAA AAC CAT GAC TTA AAA ACT    432
Lys Glu Ala Leu Asp Lys Tyr Glu Leu Glu Asn His Asp Leu Lys Thr
    130                 135                 140
```

*Fig. 10A*

```
AAG AAT GAA GGG TTA AAA ACT GAG AAT GAA GGG TTA AAA ACT GAG AAT        480
Lys Asn Glu Gly Leu Lys Thr Glu Asn Glu Gly Leu Lys Thr Glu Asn
145                 150                 155                 160

GAA GGG TTA AAA ACT GAG AAT GAA GGG TTA AAA ACT GAG TAA                522
Glu Gly Leu Lys Thr Glu Asn Glu Gly Leu Lys Thr Glu ***
                165                 170
```

Fig. 10B

TETRAVALENT C-REPEAT HYBRID

```
ATG AGA GTG CGT TAT ACT AGG CAT ACG CCA GAA GAT AAG CTA AAA AAA        48
Met Arg Val Arg Tyr Thr Arg His Thr Pro Glu Asp Lys Leu Lys Lys
 1           5                  10                  15
    M19----------------

ATT ATT GAC GAT CTT GAC GCA AAA GAA CAT GAA TTA CAA CAA CAG AAT        96
Ile Ile Asp Asp Leu Asp Ala Lys Glu His Glu Leu Gln Gln Gln Asn
             20                  25                  30

GAG AAG TTA TCT GGA TCC AGA GTG TTT CCT AGG GGG ACG GTA GAA AAC       144
Glu Lys Leu Ser Gly Ser Arg Val Phe Pro Arg Gly Thr Val Glu Asn
             35                  40                  45
             Bam H1-M6----------------------

CCG GAC AAA GCA CGA GAA CTT CTT AAC AAG TAT GAC GTA GAG AAC TCT       192
Pro Asp Lys Ala Arg Glu Leu Leu Asn Lys Tyr Asp Val Glu Asn Ser
         50                  55                  60

ATG TTA CAA GCT AAT AAT GAC AAC TTA GTC GAC GCC GTG ACT AGG GGT       240
Met Leu Gln Ala Asn Asn Asp Asn Leu Val Asp Ala Val Thr Arg Gly
 65                  70                  75                  80
                                    SalI----M5----------------

ACA ATA AAT GAC CCG CAA AGA GCA AAA GAA GCT CTT GAC AAG TAT GAG       288
Thr Ile Asn Asp Pro Gln Arg Ala Lys Glu Ala Leu Asp Lys Tyr Glu
             85                  90                  95
--------------

CTA GAA AAC CAT GAC TTA AAA ACT AAG AAT GAA GGG TTA AAA ACT GAG       336
Leu Glu Asn His Asp Leu Lys Thr Lys Asn Glu Gly Leu Lys Thr Glu
             100                 105                 110

AAT GAA GGG TTA AAA ACT GAG AAT GAA GGG TTA AAA ACT GAG AAT GAA       384
Asn Glu Gly Leu Lys Thr Glu Asn Glu Gly Leu Lys Thr Glu Asn Glu
         115                 120                 125

GGG TTA AAA ACT GAG CCA TGG GTC GCG ACT AGG TCT CAG ACA GAT ACT       432
Gly Leu Lys Thr Glu Pro Trp Val Ala Thr Arg Ser Gln Thr Asp Thr
 130                 135                 140
             Ncol----M24----------------------
```

*Fig. 11A*

```
CTG GAA AAA GTA CAA GAA CGT GCT GAC AAG TTT GAG ATA GAA AAC AAT    480
Leu Glu Lys Val Gln Glu Arg Ala Asp Lys Phe Glu Ile Glu Asn Asn
145             150                 155                 160

ACG TTA AAA CTT AAG AAT AGT GAC TTA AGT TTT AAT AAT AAA GCG TTA    528
Thr Leu Lys Leu Lys Asn Ser Asp Leu Ser Phe Asn Asn Lys Ala Leu
                165                 170                 175

AAA GAT CAT AAT GAT GAG TTA ACT GAA GAG TTG AGT AAT GCT AAA GAG    576
Lys Asp His Asn Asp Glu Leu Thr Glu Glu Leu Ser Asn Ala Lys Glu
            180                 185                 190

AAA CTA CGT AAA AAT GAT AAA TCA CTA TCT GAA AAA GCT AGT AAA AAT    624
Lys Leu Arg Lys Asn Asp Lys Ser Leu Ser Glu Lys Ala Ser Lys Asn
        195                 200                 205

CAA GAA TTA GAG GCA CGT AAG GCT GAT CTT GAA AAA GCA TTA GAA GGC    672
Gln Glu Leu Glu Ala Arg Lys Ala Asp Leu Glu Lys Ala Leu Glu Gly
    210                 215                 220

GCA ATG AAT TTT TCA ACA GCG GAT TCA GCT AAA ATC AAA ACC TTA GAA    720
Ala Met Asn Phe Ser Thr Ala Asp Ser Ala Lys Ile Lys Thr Leu Glu
225                 230                 235                 240

GCA GAG AAA GCT GAT CTT GAA CGA TCG AAC AAA ATT TCA GAC GCA AGC    768
Ala Glu Lys Ala Asp Leu Glu Arg Ser Asn Lys Ile Ser Asp Ala Ser
                245                 250                 255
                    Bam H1--M5 C-REPEAT #1-------------

CGT AAG GGT CTT CGT CGT GAC TTA GAC GCA TCG CGT GAA GCT AAG AAG    816
Arg Lys Gly Leu Arg Arg Asp Leu Asp Ala Ser Arg Glu Ala Lys Lys
            260                 265                 270

CAA TTA GAA GCT GAA CAC CAA AAA CTT GAA GAA CAA AAC AAG ATT TCA    864
Gln Leu Glu Ala Glu His Gln Lys Leu Glu Glu Gln Asn Lys Ile Ser
        275                 280                 285
                                            C-REPEAT #2----

GAA GCA AGT CGC AAA GGC CTT CGC CGT GAT TTA GAC GCA TCA CGT GAA    912
Glu Ala Ser Arg Lys Gly Leu Arg Arg Asp Leu Asp Ala Ser Arg Glu
    290                 295                 300
-----------------
```

*Fig. 11B*

```
GCT AAG AAG CAA TTA GAA GCT GAA CAA CAA AAA CTT GAA GAA CAA AAC      960
Ala Lys Lys Gln Leu Glu Ala Glu Gln Gln Lys Leu Glu Glu Gln Asn
305                 310                 315                 320
                                                             C-

AAG ATT TCA GAA GCA AGT CGC AAA GGC CTT CGC CGT GAT TTA GAC GCA     1008
Lys Ile Ser Glu Ala Ser Arg Lys Gly Leu Arg Arg Asp Leu Asp Ala
                325                 330                 335
REPEAT #3-----------------------

TCA CGT GAA GCT AAG AAA CAA                                         1029
Ser Arg Glu Ala Lys Lys Gln
            340
```

*Fig. 11C*

TETRAVALENT WITH SHORT SUBUNITS

```
ATG GTC GCG ACT AGG TCT CAG ACA GAT ACT CTG GAA AAA GTA CAA GAA     48
Met Val Ala Thr Arg Ser Gln Thr Asp Thr Leu Glu Lys Val Gln Glu
 1           5                  10                  15
    M24--------------------

GGA TCC GCC GTG ACT AGG GGT ACA ATA AAT GAC CCG CAA AGA GCA AAA     96
Gly Ser Ala Val Thr Arg Gly Thr Ile Asn Asp Pro Gln Arg Ala Lys
            20                  25                  30
Bam H1--M5-------------------

GAA GTC GAC AGA GTG TTT CCT AGG GGG ACG GTA GAA AAC CCG GAC AAA    144
Glu Val Asp Arg Val Phe Pro Arg Gly Thr Val Glu Asn Pro Asp Lys
        35                  40                  45
    Sal I---M6------------------

GCA CGA CCA TGG AGA GTG CGT TAT ACT AGG CAT ACG CCA GAA GAT AAG    192
Ala Arg Pro Trp Arg Val Arg Tyr Thr Arg His Thr Pro Glu Asp Lys
     50                  55                  60
         Nco I---M19-----------------

CTA AAA AAA TAA                                                    204
Leu Lys Lys ***
 65
```

*Fig. 12*

M24-M5-M6-M19-M3-M1-M18-M12 MULTIVALENT HYBRID M PROTEIN

```
ATG GTC GCG ACT AGG TCT CAG ACA GAT ACT CTG GAA AAA GTA CAA GAA          48
Met Val Ala Thr Arg Ser Gln Thr Asp Thr Leu Glu Lys Val Gln Glu
 1               5                  10                  15
    M24--------

GGA TCC GCC GTG ACT AGG GGT ACA ATA AAT GAC CCG CAA AGA GCA AAA          96
Gly Ser Ala Val Thr Arg Gly Thr Ile Asn Asp Pro Gln Arg Ala Lys
            20                  25                  30
    BamH1---M5----

GAA GTC GAC AGA GTG TTT CCT AGG GGG ACG GTA GAA AAC CCG GAC AAA         144
Glu Val Asp Arg Val Phe Pro Arg Gly Thr Val Glu Asn Pro Asp Lys
            35                  40                  45
        Sal1----M6----------

GCA CGA CCA TGG AGA GTG CGT TAT ACT AGG CAT ACG CCA GAA GAT AAG         192
Ala Arg Pro Trp Arg Val Arg Tyr Thr Arg His Thr Pro Glu Asp Lys
            50                  55                  60
            Nco1----M19--------

CTA AAA AAA CTG CAG GAT GCT AGG AGT GTT AAT GGA GAG TTT CCT AGA         240
Leu Lys Lys Leu Gln Asp Ala Arg Ser Val Asn Gly Glu Phe Pro Arg
 65                  70                  75                  80
            Pst1----M3----------------

CAT GTT AAA TTA ATC GAT AAC GGT GAT GGT AAT CCT AGG GAA GTT ATA         288
His Val Lys Leu Ile Asp Asn Gly Asp Gly Asn Pro Arg Glu Val Ile
                85                  90                  95
            Cla1----M1------------------

GAA GAT CTT GCA GCA GAA TTC GCA CCT CTT ACT CGA GCT ACA GCA GAC         336
Glu Asp Leu Ala Ala Glu Phe Ala Pro Leu Thr Arg Ala Thr Ala Asp
                100                 105                 110
            EcoR1---M18---------

AAT AAA GAC GAA TTA ATA CGA TCG CAT AGT GAT TTA GTC GCA GAA AAA         384
Asn Lys Asp Glu Leu Ile Arg Ser His Ser Asp Leu Val Ala Glu Lys
            115                 120                 125
                Pvu1----M12----------------

CAA GCT TTA GAA GAT TTA GGA TAA                                         408
Gln Ala Leu Glu Asp Leu Gly ***
            130                 135
```

Fig. 13

RECOMBINANT MULTIVALENT M PROTEIN VACCINE

CROSS-REFERENCE TO RELATED APPLICATION

This application is a continuation-in-part of U.S. patent application Ser. No. 07/945,954, now abandoned, filed Sep. 16, 1992.

FIELD OF THE INVENTION

The invention relates to recombinant multivalent M protein vaccines useful to control group A streptococcal infections of different serotypes which may result in rheumatic fever, rheumatic heart disease, and to other embodiments further described herein.

BACKGROUND OF THE INVENTION

Acute rheumatic fever (ARF) is the major cause of heart disease in children around the world. The disease is rampant in developing countries where prevalence rates of rheumatic heart disease may be as high as 35–40 per thousand individuals. By one estimate, it affects nearly six millon school-age children in India. Although the incidence of ARF in the United States and other Western countries declined markedly during the later half of the twentieth century, there has been a recent remarkable resurgence of the disease in the United States. Hence, the need for a safe and effective vaccine is urgent and serious.

Streptococci are a group of bacteria with the capacity to grow in chains. Many varieties are part of the normal bacterial flora in humans and are not especially harmful. However, a particular subgroup of streptococcal bacteria, called group A and represented by *Streptococcus pyogenes*, is a human pathogen. Between 20 and 30 millon cases of group A streptococcal infections occur every year in the United States alone. These cases include infections of the skin and throat, forms of pneumonia and a more recently identified disease resembling toxic shock. The most common infection is acute streptococcal pharyngitis, or strep throat, which occurs predominantly in school-age children. Strep throat qualifies as a major worldwide health problem if judged only by time lost from school and work and by the amount spent on related doctor's fees.

Strep throat's toll is much greater, however. In as many as 4% of the pharyngitis cases that are untreated or treated ineffectively, the strep infection leads to ARF. Current attempts to revent ARF rely on treatment of the pharyngitis with antibiotics. During a recent outbreak of ARF in Utah, only a fourth of the patients sought health care prior to the onset of symptoms, and only a third recalled a recent sore throat. The finding that ARF may follow a subclinical infection in such a high percentage of individuals and the fact that access to health care in developing countries is not widely available serve to underscore the need for a safe and effective vaccine against group A streptococci.

The causal relationship between streptococcal pharyngitis and ARF was established over 50 years ago, yet the mechanism of the pathogenesis of the disease remains unclear. It is widely held that ARF is an autoimmune disease, and that in the susceptible host the infection triggers an immune response that leads to inflammatory and sometimes destructive changes in target tissues. Streptococci have been shown to contain antigens that are immunologically cross-reactive with host tissues and heart-cross-reactive antibodies from patients with rheumatic fever have been shown to react with streptococci. However, it was also shown that sera from patients with uncomplicated pharyngitis also may contain heart-cross-reactive antibodies, yet these patients do not develop clinical evidence of carditis. Until the significance of tissue-cross-reactive antibodies in the pathogenesis of ARF is better understood, there remains a need to exclude potentially harmful epitopes from vaccine preparations.

The surface M protein of group A streptococci is the major virulence factor and protective antigen of these organisms, group A streptococci have developed a system for avoiding some of the antimicrobial defenses of a human host. Strains of streptococci that are rich in M protein evade phagocytosis by PMNs and multiply in non-immune blood. Yet, resistance to an infection by these bacteria is possible if the host's body can produce opsonic antibodies directed against the M protein. Such antibodies will neutralize the protective capacity of the M protein and allow the streptococcus to be engulfed and destroyed by phagocytes. The development of secretory or mucosal antibodies as opposed to serum opsonic antibodies, are also now suspected of playing an important role in preventing streptococcal infections.

A major obstacle to effective vaccine development has been the very large number of M protein serotypes. See, Stollerman, "Rheumatic Fever and Streptococcal Infection, Grune & Stratton (1975). These are reported to number about 82 to date and more can be expected to be identified.

It has been shown that antibodies against one serotype do not necessarily offer protection against others although some do cross-react with others. Immunity then appears to be type or sero-specific and optimal vaccines would require that most of the serotypes be represented. The concept of "rheumatogenic" and "non-rheumatogenic" organisms is supported by multiple surveillance studies over many years and in diverse areas of the world. Thus, there are probably about 12–15 serotypes responsible for most cases of ARF. Some of these are types 1, 3, 5, 6, 14, 18, 19, 24, 27 and 29.

To assist in a better understanding of the invention, a description of the M protein structure is useful. See, Scientific American, June 1991, Streptococcal M Protein by Vincent A. Fischetti. Considering a typical M protein structure such as that of type M6, approximately 80 percent of the M6 molecule is made of four distinct regions, each of which consists of repeated sequences of amino acids. These regions are arbitrarily designated by the letters A through D. Near the N-terminal, or amino end, the part of the molecule farthest from the bacterial cell, lies region A. This region has five tandem repeats, or blocks, of 14 amino acids each. The three central repeats are identical, whereas the repeats at each end of the region diverge slightly from the common amino acid sequence. Next on the molecule is region B, which has a similar five-repeat structure except that the repeated blocks contain 25 amino acids. Region C consists of two and a half tandem repeats of 42 amino acids each; these blocks are not as identical to one another as those in the A and B repeats. Region D is composed of four partial repeats containing seven amino acids. The section buried in the cell extends from about the last repeat of the C region to the C-terminus.

Adjacent to the D-repeat blocks is a non-repeat region containing an abundance of proline and glycine amino acids, which are distributed in a nearly regular pattern. Beyond that region lies the C-terminal, or carboxyl, end of the molecule, which is the part within the cell. Near the C-terminal end are 20 hydrophobic amino acids and, at the terminus, six charged amino acids.

Similar arrangements of repeat blocks occur in the M proteins from type 5, 12, 24 and other streptococci. An alignment of the amino acid sequences of these different M proteins reveals that their C-terminal ends are more than 98 percent identical. Closer to the N-terminus, however, differences in sequence among M proteins increase. Consequently, the A-repeat blocks and a short amino acid region of about 10 to about 20 amino acids at the N-terminus are unique for each M molecule. This uniqueness is the major determinant of the sero-specificity of the immunological response.

In the amino acid sequence of M6 and later discovered in other M protein, another intriguing structural detail revealed itself. Running throughout all the repeat regions is an unusual seven-amino acid pattern: the amino acids in the first and fourth positions are hydrophobic; the intervening amino acids allow the protein to twist itself into a spiral shape called an alpha helix.

The seven-unit pattern in the arrangement of the amino acids in M6 indicates that the repeat regions of the protein molecule make up a long helical rod. The pattern in M6 is not perfect, nor is that pattern found in many other coiled-coil structures. Such irregularities probably account for the flexibility of the M molecules observed in electron micrographs. More important, the characteristics of these irregularities differ in the A-, B- and C-repeat regions. This observation suggests that each repeat region evolved independently and may have a distinct function. For an illustration of the protein sequence of M6 determined by cloning its gene, and for different forms of related M proteins when mutant streptococci delete copies of the amino acid repeats found in the parental molecule, especially in the N-terminus, see Scientific American, cited above. Studies have shown that each M protein fiber on a streptococcal cell wall is about 50 to 60 billionths of a meter long and consists of a single coiled-coil dimer (two M proteins coiled around each other).

It is likely that M proteins of all serotypes are built along a basic theme; they have a lengthy coiled-coil rod region in their centers that is flanked by a floppy section at the N-terminal end and an anchoring region at the C-terminal end. Because the alpha-helical coiled-coil structure can accommodate a large number of varying amino acid sequences, many different M proteins with the same general conformation can be constructed, as is shown hereinafter.

For an M protein to protect a streptococcus, it must be able to attach to the organism. The mechanism that holds surface proteins on gram-positive bacteria is still poorly understood, but various studies of the M protein have been enlightening in that respect.

It is believed that the 20-hydrophobic amino acids near the C-terminal end are positioned into the similarly hydrophobic membrane itself, whereas the charged amino acids at the very terminus protruded into the aqueous cytoplasm. Because the charged amino acids would resist moving into a hydrophobic environment, they would act like a knot at the end of a string, preventing the M molecule from being pulled through the membrane. That mechanism may be valuable for some proteins attached to membranes. More recent evidence indicates, however, that the attachment mechanism for M protein and other bacterial surface proteins may actually be more sophisticated. Studies have revealed that all surface proteins from gram-positive bacteria have a similar arrangement of hydrophobic and charged amino acids at their C-terminal end. See for instance Fischetti et al., Surface Proteins from Gram-Positive Cocci Share Unique Structural Features, *New Perspectives on Streptococci and Streptococcal Infections*, (G. Orefici, Editor), Gustav and Jena (Publishers) 1992.

More important, however, a short six-amino acid sequence adjacent to the hydrophobic region is highly conserved in all the known surface proteins of gram-positive bacteria. The sequence consists of a leucine, a proline, a serine, a threonine, a glycine and a glutamic acid. Its designation is usually abbreviated as LPSTGE (SEQ ID NO:23).

The importance of the LPSTGE (SEQ ID NO:23) sequence in the attachment of the M protein (and probably in all other proteins with this sequence motif) was shown by reported genetic experiments. It was found that if only the LPSTGE (SEQ ID NO:23) sequence is removed from the M protein gene, the M molecule that was produced would not attach to the bacterial membrane. This result suggested that the hydrophobic domain and the charged amino acids at the C-terminus are not sufficient for membrane attachment and that the LPSTGE motif may be an important signal for initiating the process.

In nearly all surface proteins found in gram-positive bacteria, there is another distinctive region that spans about 50 to 75 amino acids on the N-terminal side of the hydrophobic region. This part is probably located within the peptidoglycan. Proline, glycine, threonine and serine constitute a high percentage of these amino acids. The reason for their prevalence has not been fully explored, but it is thought that prolines and glycines can create turns and bends in proteins. One hypothesis holds that cross-links in the peptidoglycan can weave through the proline- and glycine-induced bends, thereby stabilizing the M protein's position in the cell wall.

The knowledge that all known surface proteins on gram-positive bacteria attach themselves by a similar mechanism may open new avenues, such as controlling infections caused by these organisms. Surface proteins help pathogenic organisms initiate infections. It has been proposed that by preventing the proteins from anchoring to the bacterial cell, one should eventually be able to block infections and circumvent some of the problems associated with resistance to antibiotic therapies.

Just as the structures at the C-terminal end of the molecule provide information on how the M protein attaches to the bacterial cell, structures at the N-terminal end offer clues about how the molecule helps to fend off phagocytes. The N-terminal end of all M molecules has an excess of negatively charged amino acids, which results in a net negative charge for the region. Mammalian cells also exhibit a net negative charge on their surface. It has been suggested that the charge on M proteins may thus have evolved to hamper contact between streptococci and phagocytic cells through electrostatic repulsion. It has been proposed that one function of the central rod in the M protein is to act as a shaft for holding the negatively charged N-terminal end—and phagocytes—away from the bacterial surface.

At the N-terminal end of the coiled-coil rod, there is also a hypervariable region. This part of the molecule has a distinctive sequence in each M serotype. The hypervariable region consists of the short 10–30-amino acid non-helical sequence and if present, the adjoining A-repeat region. The hypervariable region plays an important role in the biological activity of the molecule; antibodies against this area are optimal at promoting phagocytosis and killing of the streptococci. This observation again explains why only serotype-specific antibodies protect against strep infections.

One hallmark of rheumatic fever is the presence of antibodies that react with muscle tissue, particularly heart tissue, in a patient's serum. See "Rheumatic Fever" by Earl H. Freimer and Maclyn McCarty; Scientific American, December 1965. Normally, antibodies are not made against one's own tissues. Researchers have discovered, however, that so-called cross-reacting antibodies can sometimes be induced by a molecule in an infective organism that resembles one in the mammalian host. In the process of making antibodies against the microbial molecules to clear an infection, the body is tricked into generating antibodies against its own tissues (serological cross-reactivity), a potentially harmful development.

It is evident from this description that there is an important and urgent need for a vaccine which is effective against the various serotypes of group A streptococci. The vaccine should be capable of raising sero-specific antibodies, especially those capable of triggering acute rheumatic fever, without eliciting cross-reaction with human tissue. There is also an important need for a vaccine which has not only these properties but also is capable of raising protective antibodies against infections, sore throat, skin infections, deep tissue infections and the like that are not necessarily but frequently are followed by rheumatic fever. The invention contributes to solving these important needs in human health.

Thus, there is an important need for a vaccine effective against streptococci infections which provides humoral immune against the diverse serotypes of group A streptococci and, when desired, also cellular immune responses. The vaccine should not elicit antibodies which react with human heart tissue.

In conjunction with studies of the M protein of various serotypes, it has been found that in most cases the protective epitopes of M protein may be separated from the potentially harmful, autoimmune epitopes of the molecule (see Refs. 5–7). The $NH_2$-terminal segments of M proteins have been found to evoke antibodies with the greatest bactericidal activity.

Further studies have shown that synthetic peptides copying limited regions of types 5, 6 and 24 M proteins evoked type-specific, opsonic antibodies that were not heart tissue cross-reactive. Because of their lack of immunogenicity, however, it was necessary to chemically link the synthetic peptides covalently to carrier proteins (see Refs. 5–7). Such fragments of M proteins linked to carrier proteins with chemical reagents do not result in hybrid proteins of defined structures. Thus, it has not been possible to obtain antigens which can elicit specific, desired antibodies without causing an increase of the risk of undesirable side reactions. Further, formation of hapten—carrier complexes using chemical cross-linking reagents is time-consuming and costly and results in undefined heterogenous mixtures of vaccine components. This invention provides multivalent vaccines that are type-specific and do not have the drawbacks of the prior art.

SUMMARY OF THE INVENTION

This patent application is related to and is co-filed on the same day as patent application Ser. No. 07/945,860 entitled "ANTIGEN OF HYBRID M PROTEIN AND CARRIER FOR GROUP A STREPTOCOCCAL VACCINE" with named inventor James B. Dale.

The invention relates to a recombinant multivalent hybrid M protein vaccine against multiple serotypes of group A streptococci. The vaccine comprises a protein molecule which contains epitopes (antigenic determinants) that evoke opsonic antibodies against multiple serotypes of group A streptococci. The molecule contains one amino acid fragment which contains at least one epitope which evokes humoral, opsonic antibodies of a particularly serotype. The respective fragments are optionally linked in tandem by linkers which include amino acids. The M protein is free of epitopes that raise antibodies cross-reactive with the human heart tissue. The hybrid M protein is made by recombinant DNA technology.

The multivalent hybrid M protein contains amino acid fragments which are amino terminal fragments of the M protein and hence are capable of eliciting the desired opsonic antibodies against the multiple serotypes of group A streptococci. The invention also relates to multivalent hybrid M proteins which, in addition to amino acid fragments which evoke opsonic antibodies against specific serotypes of group A streptococcus, also carry amino acid fragments with epitopes which also evoke protective, cellular or mucosal antibodies.

In the hybrid M protein of the invention, the amino acid fragments need not all be immunogenic as such, yet when co-expressed with other amino acid fragments, the hybrid molecule is immunogenic against at least more than one serotype of group A streptococci.

Of particular interest are recombinant multivalent hybrid immunogenic M proteins which comprise amino terminal fragments of the M protein which contain epitopes that elicit antibodies which are causative of rheumatic fever, such as serotypes 1, 3, 5, 6, 14, 18, 19, 24, 27 and 29 or others. Ideally, the hybrid M protein is constituted of a multiplicity of amino acid fragments preselected to elicit antibodies against the particular target serotypes of group A streptococci.

The invention also relates to a vaccine of the M protein type which is multivalent or general, such as tetra, penta or hexavalent against the corresponding number of serotypes of group A streptococci. Thus, the invention relates to hybrid proteins which comprise different amino acid fragments of the C-repeats of an M protein of different serotypes which cause cellular immune responses, particularly those which are not tissue cross-reactive. Such hybrid proteins can also include fragments of the amino-terminal of the various serotypes to give a hybrid composite which elicits a humoral immune response and one or more cellular immune responses. The multivalent vaccines may contain one or more than one, i.e. repeats of any particular amino terminal fragment of different serotype.

Further, the fragments need not, but may be of the same amino acid lengths. Further, the invention contemplates a mixture or a "cocktail" of hybrid M protein which carry appropriate epitopes to elicit the desired opsonic antibodies against the target serotypes. The mixture of these hybrids will be effective against a large number, if not all, of the target streptococcal types, particularly those which are causative of rheumatic fever.

The invention also relates to mixtures of individual hybrid M protein molecules which are capable of not only eliciting opsonic antibodies against multiple serotypes of group A streptococci but also to elicit mucosal antibodies. In this manner, the invention provides as desired, a complete vaccine not only against those serotypes more likely to initiate or cause rheumatic fever, but also those which cause infections described above, which often can lead to rheumatic fever.

In accordance with the invention, the amino acid fragments which carry the desired protective epitopes (opsonic or mucosal) may be (but need not be) fused to each other in tandem by linkers which comprise amino acids. A great variety of such amino acid linkers can be used in accordance with the invention. It is desirable that the amino acids contribute to the orientation, conformation and in effect to the immunoaccessability of the epitopes of the fragments so as to generate an optimum immune response. It is not excluded that these amino acid linkers contain one or more molecules which are not amino acids.

In accordance with the invention, the order, i.e., the sequence of the amino acid fragments that constitute the hybrid M proteins which carry the protective epitopes can be changed as desired to maximize the immunogenicity of the molecule.

As referred to above, the invention relates to hybrid M proteins which include amino acids of the amino termini of the M proteins, i.e. M24, M5, M6 and M19 and amino acids of the carboxyl-terminus of type 5M protein. This vaccine raises type-specific opsonic antibodies against all of the related M fractions, cross-protective mucosal immune responses against two or more of these and cellular immunity.

The invention also relates to a particular PCR method which permits to organize the coding nucleotide sequences to express the desired amino acid fragments (or sequences) in the order desired.

The invention also relates to a method of immunization with the therapeutic recombinant multivalent hybrid M proteins of the invention or with a composition which comprises the recombinant hybrid multivalent M protein and an appropriate biochemically or pharmaceutically-acceptable carrier. The immunogenic hybrid M proteins of the invention may be formulated with the biochemically or pharmaceutically-acceptable carrier to produce a vaccine which elicits an effective level of the desired antibody in the subject mammal, including human beings, to provide the desired immunity, i.e. humoral or humoral and cellular.

Further, the invention relates to a virulent microorganisms transformed (or transfected) with recombinant multivalent hybrid M protein genes (or portions) thereof of the invention. The microorganism can be a virulent as such or may have been rendered non-virulent by methods known in the art. The a virulent host bacterium is unable to colonize in the subject to be immunized generally by virtue of a nutritional deficiency; nonetheless the bacterium will multiply just to a limited extent to release the M protein antigen and elicit the appropriate antibodies. Such compositions are very well suited for oral administration.

The invention also relates to the hybrid genes which code for and express the desired hybrid M proteins in an appropriate self-replicative vehicle.

The invention further provides for modification of the amino acid sequences constituting the hybrid antigenic molecule by chemical method if it is desired to add to and/or replace any one of the amino acids by another molecule to increase and/or modify the immunogenicity of the hybrid molecule.

This summary of the invention is not intended to summarize all the embodiments (or aspects) of the invention.

BRIEF DESCRIPTION OF THE FIGURES

FIG. 1 shows the recombinant DNA nucleotide sequence (SEQ ID NO:1) of recombinant and trivalent amino acid sequences of M24-M5-M6 (SEQ ID NO:2).

FIG. 4 shows the recombinant DNA nucleotide sequence (SEQ ID NO:3) and deduced amino acid sequence (SEQ ID NO:4) of tetravalent amino acid sequence of tetravalent M24-M5-M6-M19 hybrid molecule.

FIG. 6 shows the DNA recombinant nucleotide sequence (SEQ ID NO:5) and deduced amino acid sequence (SEQ ID NO:6) of tetravalent hybrid M24-M5-M6-M19 with different linkers.

FIG. 7 shows the DNA recombinant nucleotide sequence (SEQ ID NO:7) and deduced amino acid sequence (SEQ ID NO:8) of tetravalent hybrid M24-M5-M6-M19 constituted of repeats of smaller fragments of each of the different serotypes with these fragments being directly linked by their respective amino and carboxy ends to the adjoining fragment at the indicated restriction sites.

FIG. 8 shows the DNA recombinant nucleotide sequence (SEQ ID NO:9) of tetravalent hybrid M24-M5-M6-M19-C-terminus of 915 nucleotides encoding the 305 amino acid long hybrid (SEQ ID NO:10) by having the COOH terminal half of M5 (SEQ ID NO:11) joined at restriction site Pst1.

FIG. 9 shows the DNA recombinant nucleotide sequence and deduced amino acid sequence (SEQ ID NO:13) of the tetravalent hybrid M19-M6-M5-M24 where the sub-units are in the reverse order than in construct shown in FIG. 4. No linkers join the fragments of the nucleotide and the of the amino acids.

FIG. 10 shows the DNA recombinant nucleotide sequence (SEQ ID NO:14) of a divalent M24-M5 hybrid (SEQ ID NO:15).

FIG. 11 shows the DNA recombinant nucleotide sequence (SEQ ID NO:16) of tetravalent M19-M6-M-5-M24 of 1029 nucleotides long linked to C-repeats of the carboxy terminal (SEQ ID NOS:17 and 18).

FIG. 12 shows the DNA recombinant nucleotide sequence (SEQ ID NO:19) of tetravalent M24-M5-M6-M19 (SEQ ID NO:20) with short 15 amino acid units linked directly to each other.

FIG. 13 shows the DNA recombinant nucleotide sequence (SEQ ID NO:21) of octavalent hybrid protein M24-M5-M6-M19-M4-M1-M18-M12 (SEQ ID NO:22) which contains a non-rheumatogenic serotype of streptococci (M12).

Figure 2:
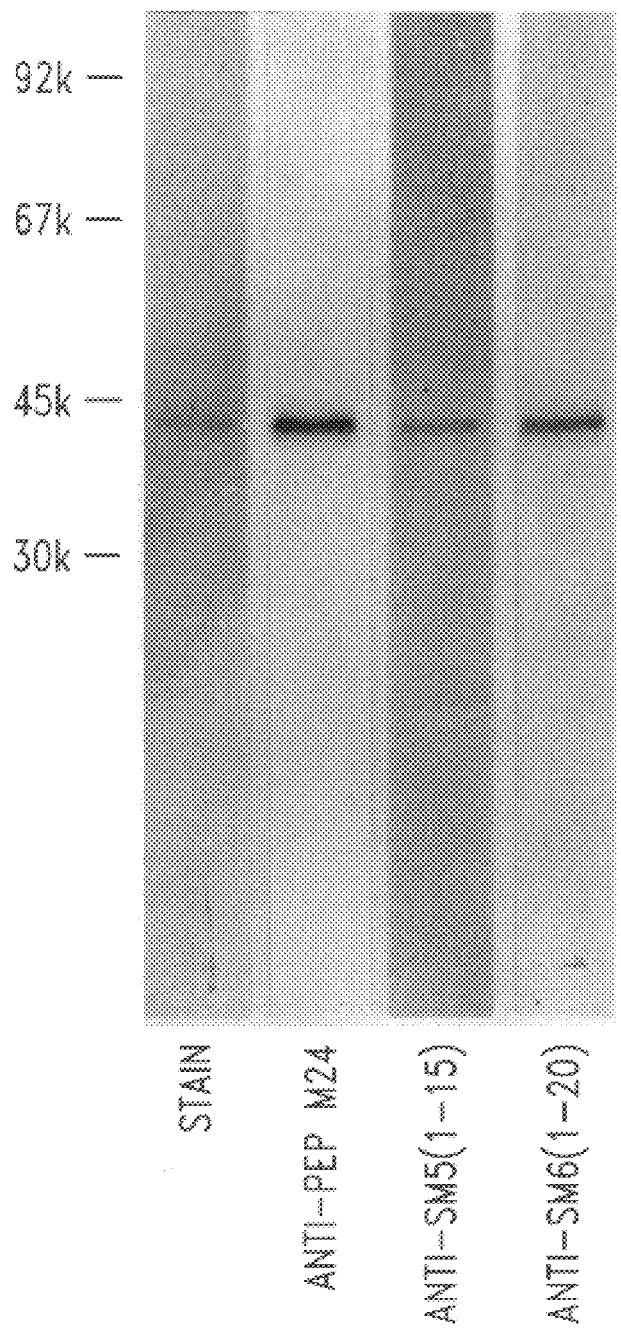
FIG. 2 shows the immunoblot analysis of purified M24-M5-M6.
Figure 3:
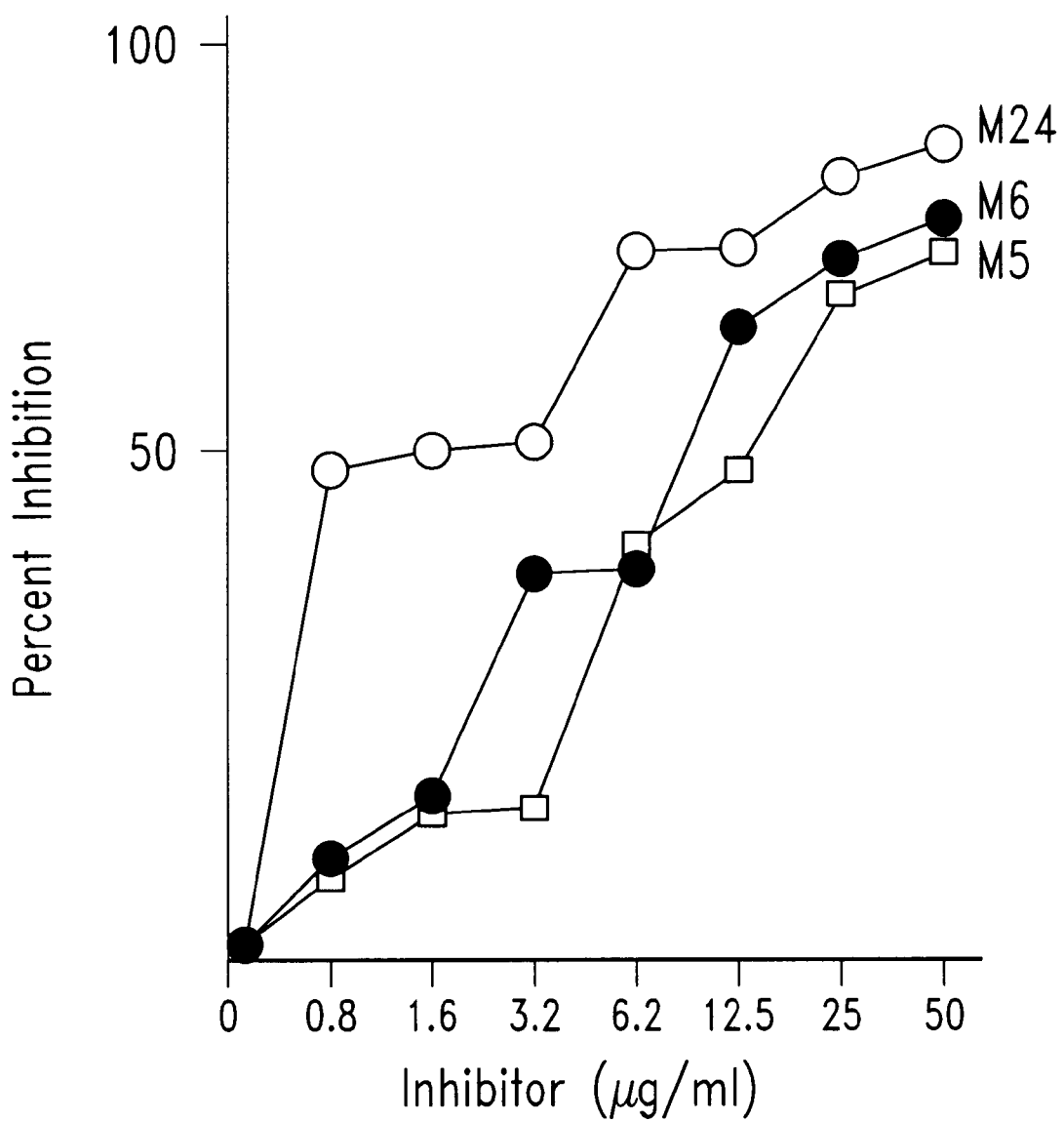
FIG. 3 shows ELISA inhibition assays.
Figure 5:
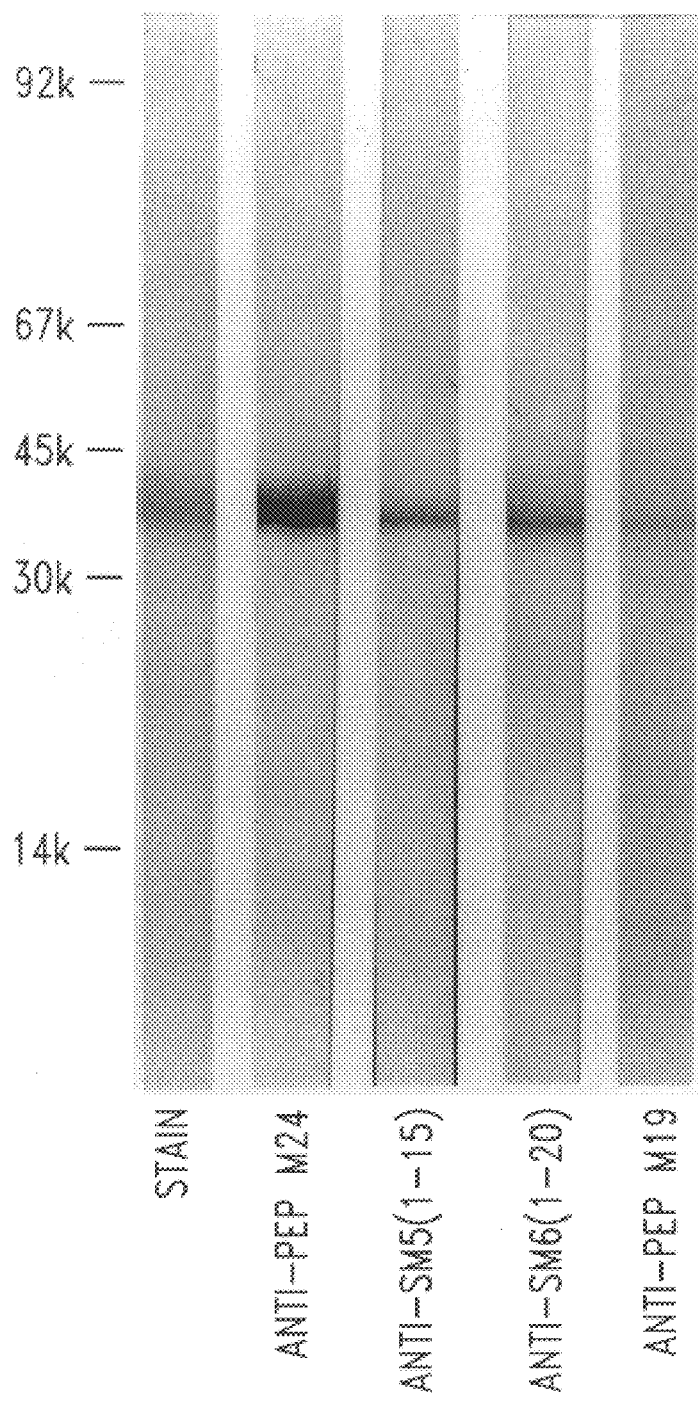
FIG. 5 shows the immunoblot analysis of M24-M5-M6-M19 hybrid vaccine.

Suitable vectors for cloning the selected DNA fragments of the M protein are available commercially. See the Bibliography provided herewith. Expression of the hybrid protein is carried out by suitable prokaryotes, like *E. coli* or if desired eukaryotes, like yeast.

DETAILED DESCRIPTION OF THE PREFERRED EMBODIMENTS

Various embodiments of the invention are more fully described hereinafter.

The construction of a trivalent and of a tetravalent hybrid antigen is described in greater detail, but it is understood that similar protocols are applicable to construct the other hybrid antigens described herein.

The method of the invention for constructing the multivalent hybrid constructs involves in vitro recombinant DNA technology. The method may be described in a general manner as follows. A polyvalent hybrid gene is constructed using a selected native fragment of the desired length and is constituted of a desired M gene like of M24, 1, 5, etc. (designated emm24, emm1 and emm5, respectively). The fragment is free of nucleotides that encode an amino acid sequence that can cause tissue cross-reactivity. The DNA sequences encoding amino acid fragments free of epitopes which cause autoimmune responses are identified as shown in the literature, for instance References 5, 6, 7 in the attached Bibliography. The fragment is amplified by polymerase chain reaction (PCR), purified and ligated into a self-replicating vehicle, e.g., a plasmid, like pBR322. Oglionucleotide pairs copying the desired codons of the structural other genes that make up the multivalent gene, respectively, are synthesized to contain appropriate restriction sites to facilitate ligation to the first selected gene, e.g. emm24. The entire polyvalent construct is excised from the vehicle (e.g., pBR322) and ligated to allow high level expression of the recombinant hybrid protein in an appropriate plasmid e.g. pKK223-3.

The selected gene (e.g. emm24) is amplified by PCR using synthetic oglionucleotide primers that specify amplification of the gene that encodes the desired region of the amino-terminal portion e.g., half of the molecule, e.g., the pep M24 region following the procedures and materials disclosed in Beachey et al., 1978 entitled "Repeating Covalent Structure of Streptococcal M Protein, *Proc. Natl. Acad. Sci. USA*, 75, 3163–3167 and Mouw et al., 1988, entitled "Molecular Evolution of Streptococcal M Protein, *J. Bacteriol.*, 170, 676. With respect to the structural gene of type 24M, the complete nucleotide sequence includes an open reading frame of 1617 base pairs encoding a pre-M24 protein of 539 amino acids a predicted M.W., of 58,738. The structural gene contains two distinct tandemly reiterated elements. The first repeated element consists of 5.3 units, and the second contains 2.7 units. Each element shows little variation of the basic 35-amino acid unit.

The (top and bottom PCR) primers are synthesized by an automated DNA synthesizer (ABI, Model 381A). When necessary i.e. when the region to be amplified does not contain an appropriate signal sequence and native start codon, the top strand primer is extended on the 5' end by an appropriate start codon like ATG.

This is performed in the case of emm24. Appropriate restriction sites (e.g. EcoR1) are also added and a GGG tail incorporated to ensure that the enzyme would recognize the cleavage site in the purified, double stranded DNA product. The bottom strand primer is extended on the 5' end by an appropriate restriction site (e.g., BamH1) and a CTC tail.

PCR amplification is performed using chromosomal DNA extracted from the selected type streptococci (e.g. type 24), which is then used as template. See Dale et al., Type-Specific Immunogenicitt of a Chemically Synthesized Peptide Fragment of Type 5 Streptococcal M Protein, *J. Exp. Med.*, 158, 1727 (1983). The reaction mixtures comprise template DNA, primer pairs, dNTPs and Taq DNA polymerase in PCR buffer. Amplification is performed in an appropriate automatic thermal cycler with denaturation, primer annealing and primer extension in accordance with standard methods. The PCR product is electrophoresed by known methodology and the purified product is, if necessary, repaired using Klenow fragment and cut sequentially with the appropriate restriction enzymes, in this case EcoR1 and BamH1 in appropriate buffers.

The purified PCR product (e.g. emm24) is ligated into an appropriate self-replicating vehicle such as pBR322 cut with restriction enzymes like EcoR1 and BamH1. The plasmid is used to transform *E. coli* strain mC1061 by standard method. Transformants are screened for the presence of plasmids containing inserts of the appropriate size and gels and one plasmid for purification and ligation of the other synthetic oglionucleotide pairs previously synthesized.

The selected oglionucleotides (emm5) are mixed in equimolar ratios and allowed to re-anneal. The selected oglionucleotide pair (e.g. emm5) is then ligated to the purified cut plasmid used to transform an appropriate strain of *E. coli*, such as mC1061. Plasmids containing appropriately sized inserts are identified and one is selected for ligation of the additional oglionucleotide pairs (e.g. emm6) which is accomplished in a similar manner. The resulting polyvalent plasmid e.g. pCDM24 M5-M6 is then purified and cut with restriction enzymes. The excised polyvalent hybrid gene (e.g. emm 24-5-6) is then ligated into a high level expression vector (e.g. pKK223-3) that contains a promoter and a ribosome binding site adjacent to the cloning side. e.g. EcoR1.

In a similar manner, other multivalent hybrid gene constructs are synthesized. For instance the M24-M5-M6-M19 tetravalent hybrid protein is constructed using fragments of the 5' region of the emm genes amplified by PCR, purified, ligated and tandem and expressed in pKK223-3.

Sequence analysis of the polyvalent hybrid emm genes are confirmed by sequencing appropriate inserts in an appropriate vehicle, such as pKK223-3 by the dideoxy-nucleotide chain termination method of Sanger et al., DNA Sequencing with Chain-Terminating Inhibitors, *Proc. Natl. Acad. Sci. USA*, 74, 5463 (1977).

The method of the invention includes the purification of the recombinant hybrid M proteins. These are purified from extracts of an *E. coli*, cells are pelleted and treated by standard purification methods, and finally lyophilized.

The invention also includes a method for synthesizing by PCR a recombinant DNA sequence which is constituted by the desired nucleotide in the particular order (sequence) and of the particular size and orientation desired. Considering that the objective is to synthesize a DNA sequence constituted of sequences A-B-C-D the following procedure is followed. After cutting PCR-generated fragment A and B with the desired restriction enzyme at the unique sites encoded by 5' end of PCR primers, A and B are ligated to each other. The A-B fragment is amplified using as primer the A top strand oligonucleotide and the B bottom strand oligonucleotide, thus amplifying only the A-B ligation product. This product is ligated to fragment C. The A-B-C fragment is in turn PCR amplified using the top oligonucleotide strand of A as primer and the C bottom strand oligonucleotide as primer, thus only amplifying the A-B-C strand.

This product is ligated to fragment D. The fragment A-B-C-D is in turn amplified using the top oglionucleotide strand of A as primer, and the bottom strand of D as primer, thus amplifying only the A-B-C-D strand desired.

In a variant of the procedure, A-B fragment can be amplified, C-D synthesized, as described for A-B. Then A-B and C-D are ligated and PCR amplified using the top oglionucleotide strand of A as primer and the D bottom strand oligonucleotide, thus amplifying the desired A-B-C-D sequence.

If it is desired to incorporate additional sequences containing for instance, amino acids as linkers (as described herein) between the amino acid segments, these molecules (e.g. amino acids) can be encoded by nucleotides contained in the primers utilized to amplify the desired fragment(s).

Thus the PCR-generated fragments are ligated in the desired order and portions are PCR amplified using the upper and lower strands as illustrated. The method avoids arrangements of nucleotide segments in an undesired sequence or orientation. The same methodology is followed for longer fragments and variations can be readily provided.

The polyvalent hybrid M proteins of the invention are tested by immunization of rabbits, a classic test animal. Assay for M protein antibodies is performed in accordance with known methods as described in the appended bibliography. So are assays for heart cross-reactive antibodies which are described in Beachey and Dale, (1982).

The invention also includes the construction of hybrid constructs containing repeating amino-terminal M protein sub-units using PCR. A non-limiting illustration is described hereinafter. The method is readily applied to any number of amino acids of any particular selected serotype to yield a hybrid gene containing its selected repeated amino acid fragment.

A typical trivalent gene M24-M5-M6, was constructed in a general manner as follows.

The M24-M5-M6 hybrid gene was constructed using a native fragment of the emm24 gene that was amplified by the polymerase chain reaction (PCR), purified and ligated into pBR322. Oligonucleotide pairs copying the first 11 and 12 codons of the structural emm5 and emm6 genes, respectively, were synthesized to contain appropriate restriction sites to facilitate ligation to the emm24 gene. The entire trivalent construct was excised from pBR322 and ligated PCR amplification was performed using chromosomal DNA extracted from type 24 streptococci which was used as the template. The reaction mixtures consisted of template DNA, primer pairs, dNTPs and Taq DNA polymerase in PCR buffer. Amplification was performed in a Perkin-Elmer Cetus automatic thermal cycler with denaturation at 95° C. for 1 min, primer annealing at 55° C. for 1 min and primer extension at 72° C. for 3 min for a total of 39 cycles. The PCR product was electrophoresed in a 1% low melting-point agarose gel, the band of the predicted size was excised and purified by adsorption to and elution from "glassmilk" (Geneclean, Bio 101). The purified product was end-repaired using Klenow fragment and cut sequentially with EcoR1 and BamH1 restriction enzymes in the appropriate buffers.

The purified emm24 PCR product was ligated into pBR322 that had been cut with EcoR1 and BamH1. The plasmid was used to transform E. coli strain MC1061 by standard methods. Transformants were screened for the presence of plasmids containing inserts of the appropriate size on agarose gels. One such plasmid (pCDM24) was then selected for purification and ligation of emm5 and emm6 synthetic oligonucleotide pairs which were synthesized as described above according to the following sequences:

```
emm5 synthetic oligonucleotide pairs

1/2 BamH1                                        1/2 Sal1
5' GA TCC GCC GTG ACT AGG GGT ACA ATA AAT GAC CCG CAA G 3'      (SEQ ID NO: 26)

3'G CGG CAC TGA TCC CCA TGT TAT TTA CTG GGC GTT CAG CT 5'    (SEQ ID NO: 27)

emm6 synthetic oligonucleotide pairs

1/2 Sal1                                         -pst 1-1/2 XbaIII
5' TC GAC AGA GTG TTT CCT AGG GGG ACG GTA GAA AAX XXG GAC CTG CAG 3'  (SEQ ID NO: 28)

3'G TCT CAC AAA GGA TCC CCC TGC CAT CTT TTG GGC CTG GAC GTC GCC GG 5'   (SEQ ID NO: 29)
``` into pKK223-3 to allow high-level expression of the recombinant hybrid protein.

The emm24 gene was amplified by PCR using synthetic oligonucleotide primers that specified amplification of the portion of the gene that encodes the pep M24 region of the protein which is approximately the amino-terminal half of the molecule. The primers were synthesized by an automated DNA synthesizer (ABI, Model 381A) and had the following structures:

M24-Top Strand PCR Primer (SEQ ID NO:24)

```
    -EcoR1    START
5' GG GAA TTC ATG GTC GCG ACT AGG TCT CAG 3'
```

M24-Bottom Strand PCR Primer (SEQ ID NO:23)

```
5' CGT CTC TTT CGA CTA GAA CTT CCT AGG CTC 5'
                                    -BamH1-
```

The top strand primer was extended on the 5' end by an ATG, since the region of emm24 to be amplified excluded the signal sequence and native start codon. An EcoR1 restriction enzyme site was also added and a GGG tail was incorporated to ensure that the enzyme would recognize the cleavage site in the purified, double-stranded DNA product. The bottom strand primer was extended on the 5' end by a BamH1 restriction site and a CTC tail.

The emm5 oligonucleotides were mixed in equimolar ratios, heated at 65° C. for 2 min and allowed to reanneal at ambient temperature. pCCDM24 was cut with BamH1 and Sal1 and purified on an agarose gel as described above. The emm5 oligonucleotide pair was then ligated to the purified, cut plasmid and used to transform E. coli strain MC1061. Plasmids containing appropriate sized inserts were identified on agarose gels and one (pCDM24.M5) was selected for ligation of the emm6 oligonucleotide pairs which was accomplished in a similar manner. The resulting pCDM24.M5-.M6 was then purified and cut with EcoR1 and Pst1, the site for which was synthesized into the emm6 oligonucleotide pair. The excised emm24.5.6 hybrid gene was then ligated into pKK223-3, a high level expression vector that contains the tac promoter and a ribosome binding site adjacent to the EcoR1 cloning site.

The construction, cloning and expression of M24-M5-M6-M19 tetravalent hybrid M protein was carried out as follows.

The M24-M5-M6-M19 tetravalent M protein was constructed using fragments of the 5' regions of emm genes that were amplified by PCR, purified, ligated in tandem and expressed in pKK223-3. The overall goal was to amplify the regions of the respective emm genes that encode protective and not tissue-cross reactive epitopes and link them into one protein molecule. The recombinant hybrid protein contained 113 amino-terminal amino acids of M24, 58 amino acids of M5, 35 from M6 and 35, from M19. Each segment was linked by 2 amino acids specified by the respective restriction enzyme sites that were synthesized into the oligonucleotide primers used to specify the PCR products.

The primers for each emm gene were synthesized as described above according to the following sequences:

M24 Top Strand (SEQ ID NO:30)
-EcoR1-Start

5' GG GAA TTC ATG GTC GCG ACT AGG TCT CAG 3'

M24 Bottom Strand (SEQ ID NO:31)
-BamH1-

5' GG GGA TCC TTC AAG ATC AGC TTT CTC TGC 3'

M5 Top Strand (SEQ ID NO:32)
-BamH1-

5' GGG GGG GGA TCC GCC GTG ACT AGG GGT ACA 3'

M5 Bottom Strand (SEQ ID NO:32)
-Sal1-

5' GGG GGG GTC GAC CTC AGT TTT TAA CCC TTC 3'

M6 Top Strand (SEQ ID NO:33)
-Sal1-

5' GGG GGG GTC GAC AGA GTG TTT CCT AGG GGG 3'

M6 Bottom Strand (SEQ ID NO:34)

-Nco1-

5' GGG GGG CCA TGG TAA GTT GTC AAT AAT AGC 3'

M19 Top Strand (SEQ ID NO:35)
-Nco1-

5' GGG GGG CCA TGG AGA GTG CGT TAT ACT AGG 3'

M19 Bottom Strand (SEQ ID NO:37) 1

-Pst1-
5' GGG GGG CTG CAG AGA TAA CTT CTC ATT CTG 3'

The M24, M5 and M6 oligonucleotide sequences were based on previously published data. See Bibliography supplied herewith and incorporated herein by reference. The M19 sequence was obtained in a similar manner from a plasmid containing the entire emm19 structural gene.

The oligonucleotide primer pairs described above were used to amplify the regions of each emm gene using chromosomal DNA from the respective serotype of group A streptococci as the template in the PCR reaction, as described above. The PCR products were purified by excision from low melting point agarose. Because some of the bottom strand PCR primers annealed to regions of the emm genes that were repeated, the PCR products were of variable sizes. In each case, the smallest major band was excised and purified for ligation.

Ligation of the purified PCR products was accomplished by first cutting the M24 and M5 fragments with BamH1 and then ligating the two cut fragments. The ligation mixture was then subjected to amplification by PCR using as primers the M24 top strand oligonucleotide and the M5 bottom strand oligonuclcotide in order to amplify only the M24-M5 ligation product. This hybrid PCR product were then purified cut with Sal1 and ligated to the M6 fragment that had also been digested with Sal1. The M24-M5-M6 hybrid was once again subjected to PCR amplification using the M24 top strand primer and in this case the M6 bottom strand primer. The same sequen events was then followed to ligate the M19 component to make the completed tetravalent gene. The purified products was cut with EcoR1 and Pst1 and ligated into the respective sites of pKK223-3 which was used to transform *E. coli* strain JM105. The recombinant expressing the hybrid M protein was initially identified by screening colony blots on nitrocellulose with rabbit antisera against pep M24.

The constructing of repeating amino-terminal M protein sub-units using PCR was carried out as follows.

Multimeric amino-terminal fragments of emm genes were constructed using PCR amplification. For example, the first 12 amino acids of M19 were expressed as three repeats by the following method:

PCR Primers:

M19-5' repeater (SEQ ID NO: 38)-5' AGA CTG CGT TAT ACT AGG CAT ACG CCA GAA GAT AAG AGA GTG CGT TAT ACT AGG

M19-3' BS (SEQ ID NO: 39)-5' GGG GGG CCA TGG CTT ATC TTC TGG CGT ATG

M19-5' Monomer (SEQ ID NO: 40)-5' GGG GGG GAA TCC AGA GTC CGT TAT ACT AGG

The M19-5' repeater encodes the first 12 amino acids of the $NH_2$ terminus with the codons for the first 6 amino acids added to the 3' end of the primer as a repeating sub-unit. M19-3' BS copies the complementary strand of codons 7–12 with an Nco1 enzyme site and a poly-G clamp. The M19-5' monomer encodes the first 6 amino acids of the $NH_2$ terminus with an EcoR1 enzyme site and a poly-G clamp at the 5' end.

Template DNA from type 19 streptococci was first amplified with the M19-5' repeater and M19-3' BS which resulted in a ladder of PCR products ranging in size from 2 to –6 sub-units. One product of the appropriate size (to encode 3 sub-units) was purified from agarose gels and then subjected to PCR amplification using the M19-5' monomer and M19-3' BS primers. The single product was then ligated into the appropriate restriction sites.

The sequence analysis of the trivalent and tetravalent hybrid emm genes was carried out as follows.

The structures of the hybrid emm genes described above were confirmed by sequencing the inserts in pKK223-3 by the dideoxy-nucleotide chain termination method of Sanger et al.

The purification of recombinant hybrid M proteins was carried out as follows. The trivalent and tetravalent hybrid M proteins were purified from extracts of JM105 *E. coli* grown overnight in 11 L broth supplemented with 75 ug/ml ampicillin, 25 ug/ml streptomycin and IPTG (1 mMol). The cells were pelleted at 7000×g and resuspended in 50 ml carbonate buffer, pH 11.0 containing 100 ug/ml lysozyme, 1 mMol EDTA and 100 ug/ml PMSF and incubated at 37° C. for 30 min. The cells were centrifuged at 7000×g and the supernatant was dialyzed against distilled water and lyophilized. Purification was performed by loading 50 mg of extract containing either the trivalent M protein hybrid onto a preparative PAGE unit (Prep Cell, Model 491, Bio Rad., Inc.) using a 37 mm column and a 9 cm 11% polyacrylamide gel. Six ml fractions were collected and assayed for the presence of recombinant proteins by Western blot analysis using pep M24 antisera. Peaks containing activity were polled and lyophilized.

Immunization of Rabbits

Rabbits were immunized with 300 ug of the selected polyvalent (e.g. the trivalent or tetravalent) hybrid M proteins emulsified in complete Freund's adjuvant. Booster injections of the same dose in PBS were given at 4, 8 and 12 weeks. Blood was obtained prior to immunization and at two-week intervals thereafter. The other polyvalent hybrid M proteins are used in the same manner. Likewise, a mixture (or "cocktail") of such hybrids are used in the same manner.

Assays for M Protein Antibodies

Total antibody activity against M protein was determined by ELISA using native pep M proteins, recombinant M proteins, synthetic peptides or purified polyvalent (e.g. trivalent or tetravalent) hybrid M proteins as solid phase antigens by methods previously described. Opsonic antibodies were assayed by in vitro opsonophagocytosis tests, as described. ELISA-inhibition and opsonization-inhibition experiments were performed using purified M proteins or synthetic peptides as soluble inhibitors of M protein antibodies in ELISA or opsonization tests. Western blots of recombinant proteins were performed using antisera raised in rabbits against synthetic peptides or native M proteins. The other polyvalent hybrids were assayed following the same protocol.

Assays for Heart-Cross-Reactive Antibodies

Antisera against recombinant multivalent M proteins were screened for the presence of heart-cross-reactive antibodies by indirect immunofluorescence tests using frozen sections of human myocardium as previously described in the literature.

Assays for M Protein Epitopes that Evoke-Mucosal Antibodies Broadly Protective Against Infection Rabbit antisera were screened for the presence of broadly protective antibodies using passive mouse protection assays (see Bronze, M. S., et al., Protective and Heat-Crossreactive Epitopes Located within the N-Terminus of Type 19 Streptococcal M Protein, *J. Exp. Med.*, 167, 1849–1859 (1988).

Antisera were first tested for the ability to react with the surface M protein of multiple heterologous serotypes of group A streptococci by ELISA. Those that recognized M protein epitopes in their native conformations were then used to passively protect mice against intranasal challenge infections. Antibodies were absorbed to virulent streptococci and mice were challenged intranasally with $10^7$ CFU. Throat cultures were obtained on alternate days and deaths were counted over the ensuing 14 days. Vaccine constructs that evoke protective antibodies in rabbits will be used to immunize mice intranasally to test directly their protective immunogenicity. Actively immunized mice will be similarly challenged with virulent streptococci.

An illustration of a tetravalent hybrid gene M24-M5-M6-M19 with different linkers than shown in the FIG. 4, is shown in FIG. 6. The sequence of the hybrid gene shows the structure of emm24, emm5, emm6 and emm19. The tetravalent emm gene expresses protein with a calculated M.W. of 30.7 kDA and contains 113-amino terminal amino acids of type 24 M protein, 58 amino acids of type M5, protein 35 amino acids of type 6M protein, and 35 amino acids of type 19 M protein. The linker is a proline rich linker Pro-Gly-Asn-Pro-Ala-Val-Pro, the codons for which are inserted into the BamH1, Sal1 and Nco1 restriction enzyme sites, respectively, which were synthesized into the original PCR primers. This linker in part includes the amino acids of the restriction site codon at the desired position.

Other linkers may be used such as for instance a sequence which include amino acids like, Ile-Pro-Gly or Asp-Pro-Arg-Val-Pro-Ser-Ser.

The sequence of the amino acid in any particular linker used appears at this time not to be critical. Theoretically, a linker could be constituted by one amino acid; if the desired effect of promoting a functionally effective conformation of the encoded protein is desired, longer linkers may be selected, such as of having 14 or more (e.g. 20) amino acids.

As described herein, linkers are not essential to the structure so that it is not necessary that any one amino acid sub-unit or for that matter all amino acid by fused to each other by an amino acid linker. For an illustration, M24 and M5 can be directly fused to each other. Further, while the description herein refers to linkers constituted by amino acids encoded by hybrid genes, some hybrid constructs may contain purified recombinant M proteins which may include one or more molecules which are not an amino acid, such as succinimidyl-4-(N-maleimido-methyl) cyclohexane-1-carboxylate (SMCC). The linkers can be of same or of varying lengths between each amino acid segment. These molecules may be introduced by chemical means as opposed to being expressed with the hybrid protein.

The tetravalent hybrid gene illustrated in FIG. 6, when tested for antigenicity by reacting with polyclonal rabbit antisera raised against each one of the components of the hybrid protein, will indicate that the epitopes are present in a conformation which resembles that of the native protein.

When the immunogenicity of the tetravalent protein and the antibody level will be determined, the immune sera will also contain opsonic antibodies against all four serotypes of group A streptococci.

It is contemplated in accordance with the invention that the amino terminal amino acid fragment be constituted to contain one or more amino-terminal portions of other potentially rheumatogenic streptococci types, for instance of types 1, 3, 18, 27 and/or 29 or any other presently known or to be discovered to have such potential rheumatogenic effect. Also it is contemplated that the constructs of the invention be constructed to contain one or more fragments of the amino terminal region of serotypes which are not known to have such rheumatogenic effect, as those described above and in the literature. In those instances where such structure have not yet been sequenced or when such sequence has not yet been published, one skilled in the art by methods readily available can sequence such structures and then construct the hybrid of the invention with the desired fractions. Thus, the invention contemplates such multivalent protein encoded by appropriate hybrid gene or genes to express in an appropriate organism a protein that will elicit the desired antibodies.

The effect of the different linkers on the immuogenicity of the hybrid molecule may justify further investigations. It is not excluded that depending on the nature of the linker and of the type and size of the amino acid fractions, a hybrid protein of ideal or close to ideal high immunogenicity be identified. Such hybrid is within the scope of the invention.

What has been described herein above also applies with respect to the carboxy-terminal fraction or the C-repeats thereof when such fraction(s) or repeats are used, as described herein.

It should be kept in mind that not all—instead none—of the fragments constituting the hybrid need be immunogenic when considered individually (and without a carrier) provided that when part of the final hybrid they contribute to the desired immunogenicity or at least do not detract therefrom.

The sequence of amplified (M-like) 2, 3, 18 and 19 M genes is discussed in Podbielski et al., Application of the Polymerase Chain Reaction to Study the M Protein(-like) Gene Family in Beta Hemolytic Streptococci, *Med. Microbiol. Immunol.*, 180, 213 (1991). Genes of the M12 type (emm12) of a nucleotide sequence of 1693 base pairs is described in Robbins et al., *Streptococcus Pyogenes* Type 12 Protein Gene Regulation by Upstream Sequences, *Journal of Bacteriology*, 5633–5640 (December 1987). The $NH_2$-terminal sequence of type 1 streptococcal M protein is discussed in Kraus et al. Sequence and Type-Specific Immunogenicity of the Amino-Terminal Region of Type 1 Streptococcal M Protein, *The Journal of Immunology*, 139, 3084–3090 (November. 1987), incorporated by reference.

The $NH_2$-terminal fragment is constituted of fragments of 28-kDA, 25-, and 23.5 kDA. The article discusses similarities and differences with other $NH_2$-terminal M protein sequences. Opsonic antibodies are developed against type 1 streptococci. It is noteworthy that the $NH_2$-terminal region of type 1M protein also retains epitopes that evoke protective immune responses.

It is therefore within the scope of the invention for the hybrid construct to contain $NH_2$-terminal regions which also raise protective mucosal responses, (not only opsonic responses) in those instances where the $NH_2$-terminal region does raise both types. Thus, the carboxy terminal fragment is not always necessary for a hybrid to raise mucosal or cellular responses.

In general, the $NH_2$-terminal residues of the different M proteins which show less ordered structure and are more variable from one type to another comprises about 10 to 20 residues.

Another embodiment of the invention is illustrated in FIG. 7 which shows a M24-M24-M24-M5-M5-M5-M6-M6-M6-M19-M19-M19 multivalent hybrid of 561 nucleotides and a calculated M.W. of 21.6 kDA constituted of 187 amino acids with restriction sites between the different fragments as shown, respectively BamH1, Sal1, and Nco1. It will be observed that the repeated amino acid fractions of the respective types M24, M5, M6 and M19 (underscored) are of the same length. They need not be so. The smaller size of the repeat fragments of the construct is to enhance the immunogenicity of the entire molecule as opposed to longer fragments as described elsewhere herein and to evoke antibodies against the distal (and most protective and least tissue-cross-reactive) epitopes. Each fifteen amino acid subunit is repeated three times. Further, such smaller amino acid fragments can be more readily synthesized by an amino acid synthesizer or by a novel modification of the classic PCR method as described herein. In this embodiment of the invention, it will observed that there are no linkers.

Contemplated within the invention are similar hybrid structures in which the individual repeated segments are longer or shorter than the shown 15 amino acids. Since the individual M fragments constituting the hybrid are when considered alone, of different immunogenicity, it appears worthwhile to consider increasing or decreasing the length of one or more of such fragments to further increase the overall immunogenicity of the molecule. Linkers can also be included.

Further, anyone of the fragments here illustrated in FIG. 1 hereinabove can be replaced by another serotype, such as serotype 1, 3 or 18. In this manner, tetravalent hybrid genes can be constructed and the corresponding hybrid protein expressed. Likewise longer, such as penta-, hexa-, octa-, nona- or decavalent hybrid genes and the corresponding expressed proteins can be obtained.

In that connection, it is noteworthy that as opposed to increasing the number of amino acid fragments constituting a particular multivalent vaccine, such as to octa-, nona- or deca-multivalent vaccine, it would be more advantageous to provide a mixture of smaller constructs, the mixture being constituted by at least 2 of such constructs. In this manner, it may be a mixture of "cocktail" of multivalent vaccines can be provided which would have an optimum maximum length (or size) such as tetra- or pentavalent structure and another one of approximate similar length and constituted of other serotypes. For instance, a multivalent hybrid vaccine constituted of M24-M5-M6-M19 can be provided in admixture with one containing M1-M3-M18 and a further admixture with a multivalent hybrid vaccine constituted of M1-M24-M5 and yet a fourth one containing any one of those above mentioned including M18. It is to be observed that the order (sequence) in which these M protein fragments have been described herein is not necessarily the sequence in which the invention is limited as has been described repeatedly herein.

Another interesting illustration of a tetravalent hybrid gene of the invention is illustrated in FIG. 8 which shows the sequence of tetravalent M24-M5-M6-M19 with the carboxy terminal half of M95 joined at restriction Pst1. The hybrid construct has 305 amino acids expressed by the 915 nucleotides. The restriction sites are shown.

It will be observed that the tetravalent amino acid fragments are each of 15 amino acids long and joined directly to each other without the intermediary of amino acid linkers. This is an illustration of the concept of the invention combining the multivalent vaccine with that of a carboxy terminal of one of the M protein serotypes.

Instead of using the carboxy terminal of M5 any other M-COOH may be used such as that of M24, M19 and M6. Care will be taken of course that the carboxy terminal not be one that would generate undesirable antibodies such as tissue-cross-reactive antibodies. In the illustrated construct, not only are there generated opsonic antibodies against the four M protein fractions, but also protective mucosal antibodies against the carboxy terminal portion of the molecule. As explained herein, such a structure has distinct advantages in that in can serve as a vaccine in controlling nasal or other infections often preceding rheumatic fever.

A vaccine constituted of the construct illustrated herein, or a similar one is therefore an effective, therapeutic prophylactic agent which interesting enough may be administered nasally as by spray.

Instead of using the entire carboxyl terminal of anyone of the M-serotypes, it may be advantageous to use only one or more amino acid of the C repeats of the carboxyl terminal of a particular serotype. It is noteworthy that the carboxy terminal or the amino acid constituting one or more C-repeats used in the construct need not be one of the same serotype(s) as that which constitutes the amino terminal portion of the construct. Thus, such vaccine will provide cellular immune responses (which normally are less type-specific or more cross-reactive) than the opsonic response and concurrently provide type-specific immunity.

It should be noted in conjunction with the invention as has been described herein, that not all M protein epitopes are sero-specific in their amino terminal portion of the molecule. Some epitopes of particular serotypes, such as M5 do cross-react to some extent with streptococci of a type other than M5, such as M6 or M19. And to some extent this also occurs with other M serotypes. Accordingly, it is within the scope of this invention that when sero-specificity is referred to, this does not exclude some cross-reactivity between certain shared structures.

However, such shared epitopes are often also most likely to cross-react with heart tissue and hence present potentially serious risks and are not opsonic or do not evoke antibodies with a high level of opsonic activity desirable.

In another embodiment of the invention, the sequence of the amino terminal amino acids of the various fragments has been co-expressed in a different order. A comparison between on one hand, the structures of FIGS. 4 and 6 and on the other hand, FIG. 9 will show that the DNA recombinant nucleotide sequence and the deduced amino acid sequence of the tetravalent hybrid M19-M6-M5-M24 is in the reverse order than in the other above-mentioned constructs. The construct of FIG. 9 illustrates a multivalent vaccine having 247 amino acids expressed from a nucleotide sequence of 741 DNA nucleotides. The respective M19, M6, M5 and M24 fragments are of the following respective amino acids length: 35, 35, 58 and 113.

In studies related to the invention, it had been found that the immunogenicity of certain sub-units or fragments is greater than others. For instance, M24 is greater than M5, which in turn is greater than M6 and which in turn is greater than M19. It was also observed that the immunogenicity against the amino terminal M24 and MS sub-units in a construct containing M24-M5-M6-M19 was greater than against the M6 and M:19 components. However, it was of interest in conjunction with this invention to determine whether such postulates would hold true in the constructs of the invention, in particularly, in a total reversal of the order of the amino acid sub-units as is shown in FIG. 9 or for that matter, in the rearrangement of some of these sub-units in any order desired such as M19 followed by M6 and then followed by M24 and then by M5.

The same remarks apply with respect to the other M protein serotypes as 3, 12 and 18. Indeed it is not seen at this time why organizing the sequence of amino acids by increasing (or decreasing) immunogenicity should apply to the constructs of the invention. In that sense, the vaccines of the invention may present another interesting departure from the conventional.

The tetravalent protein reacted with polyclonal rabbit antisera raised against each component of the hybrid protein as described herein. Thus, indicating that the epitopes were present in a conformation which mimicked the native protein. Rabbits immunized with a purified tetravalent M protein are expected to develop significant antibody levels against the tetravalent vaccine of all four serotypes of the purified native M proteins. By changing the order of the amino acid fragments in the tetravalent hybrid, different levels of opsinization can be observed.

As described herein, when linkers are used, linkers which are of particularly interest are constituted to be overall hydrophobic i.e. they are constituted by a multiplicity of amino acids with non-polar groups. Included in such amino acids are those with aliphatic groups, such as alanine, leucine, isoleucine, valine and proline; with aromatic rings like phenyalaine and tryptophan, and methionine. It is in accordance with the invention that other of the 22 amino acids may be considered with the hydrophobic acids or not to form the appropriate linkages in those hybrid construct where linkages are desired.

An illustration of a divalent hybrid gene emm24 and emm5 and the amino acid sequence is shown in FIG. 10 of 522 nucleotides has expressing the hybrid protein of 174 amino acid. The restriction site BamH1 is shown.

Opsonic antibodies are elicited against the respective native M proteins. Immunogenicity is tested in rabbits.

An illustration of a tetravalent gene of the invention in FIG. 11 shows the sequence M19-M6-M5-M24 in the reverse order than shown in FIG. 8 with two and a half C-repeats of the M5-carboxyl terminal. The 1029 nucleotide long shows the restriction sites between the respective fragments and the fused C-repeats of a total of 280 nucleotides long of the carboxyl terminal amino acid region of M5.

This construct is noteworthy in that it will elicit not only antibodies against the M6-M19-M24-M5, but also against the C-repeats. Each complete C-repeat is 35 amino acids long, the last one being approximately ½ thereof. The C repeats will generate mucosal protective antibodies. Thus, again this is an interesting multi-purpose vaccine.

In yet another embodiment of the invention, a multivalent hybrid M protein with short sub-units is illustrated in FIG. 12. FIG. 12 shows the DNA recombinant DNA nucleotide sequence and deduced amino acid sequence of tetravalent hybrid M24-M5-M6-M19 which comprises 201 nucleotides coding for 67 amino acids. Of interest in conjunction with this embodiment is the shortening of each sub-unit and linkers numbering 2 amino acids encoded by the shown restriction sites BamH1, Sal1 and Nco1. By shortening each sub-unit, the immunogenicity of each one can be determined. The total size of the molecule can be minimized. This allows for the construction of multivalent constructs to which other sub-units from heterologous serotypes of M proteins are co-fused. Thus, it can readily be seen that other rheumatogenic amino terminal fragments such as serotype M1-M3-M18 can be added to this construct to render the multivalent hybrid M protein to be of increased multivalency. Or, as described above, a mixture of such smaller structures may be provided as a vaccine to the patient.

When rabbits are immunized with the purified tetravalent M protein, significant antibody levels of all four serotypes of the purified native M protein is observable. The same construct can be made, omitting the short linkers.

In a further embodiment of the invention, there is illustrated in FIG. 13, an octavalent hybrid protein M24-M5-M6-M19-M3-M1-M18-M12. This octavalent hybrid protein vaccine is constituted of a fraction of M24 of 15 amino acids long, a fraction of M5 of 15 amino acids long, of a fraction of M6 of 15 amino acids long, a fraction of M19 of 15 amino acids long, a fraction of M3 of 15 amino acids long, a fraction of M1 of 15 amino acids long, a fraction of M18 of 15 amino acids long and a fraction of M12 of 15 amino acids long.

Each amino acid being connected by a 2 amino acid long linker to the following amino acid: the nucleotide sequence being 405 long and coding the hybrid protein molecule of 135 amino acids long.

What is of particular interest in this construct of the invention is that in addition to the sub-units from rheumatogenic end terminal fractions, a non-rheumatogenic serotype of streptococci was encoded and expressed, namely, that of M12.

This is an important aspect of the invention which is not limited to a particular non-rheumatogenic M12 serotype of streptococci as illustrated. Indeed, instead of a fraction of M12 an appropriate fraction such as of 10, 12 or more amino acids of any of the non-rheumatogenic serotypes can be used such as the following: 2, 10, 8, 9, 11, 22, 33 and others.

While a certain number of the rheumatogenic type M proteins have not yet been sequenced or their sequence not yet disclosed, such sequencing is readily performed by methods known in the art and hence appropriate fractions free of epitopes that cross-react with human tissue be made to constitute the multivalent hybrid of the invention. It is also contemplated that more than one fraction of the rheumatogenic serotype of streptococci be contained in the multivalent vaccine. When the antigenicity of this octavalent hybrid protein is tested, it reacts with polyclonal rabbit antisera raised against each component of the hybrid protein. Its immunogenicity and lack of cross-reactivity with human tissue especially myocardium, can be tested in accordance with the assays described herein. Thus, the immune sera will obtain opsonic antibodies against all seven types of serotypes of group A streptococci. The immunogenicity of the tetravalent protein and the antibody level will be determined. The immune sera will also contain opsonic antibodies against all four serotypes of group A streptococci will be tested for bacterial activity in vitro on an in vivo passive mouse protection tests as described. The multivalent protein is assayed in accordance with the assay described herein for the presence of broadly protective antibodies using passive mouse protection assays. In this case actively immunized mice will be similarly challenged with the virulent streptococci.

Thus in accordance with the invention, a multivalent hybrid M protein is provided which provides broad immunity against several serotypes and also elicit protective mucosal immunity.

It is also the contemplation of the invention to have a multivalent vaccine constituted of two different serotypes followed by a non-rheumatogenic fraction as was illustrated herein above, for example in conjunction with FIG. 13. Likewise, it should be noted that it is conceivable that the hybrid gene and hence the expressed hybrid protein have the non-rheumatogenic serotype of the streptococcus as the first fraction upstream of the rheumatogenic amino acid fractions of the amino terminal portions of the respective serotypes of streptococci. Further, it is within the contemplation of the invention to construct hybrid genes and the expressed hybrid protein constituted of one rheumatogenic serotype, such as M24-M5-M6-M19-M1-M3-M18 or others followed or preceded by a non-rheumatogenic fraction of a serotype of streptococci, such as M12 or others.

Of particular interest in conjunction with the invention are vaccines which include amino acid sub-units of any or all of the 1 through 80 different serotypes known or to be discovered of which approximately 15 are known to be causative or at least to contribute in the development of acute rheumatic fever following strep throat.

It is important to note that the invention is not limited to a particular amino acid sequence wherever herein amino acid sequences are referred to or described. In any particular amino acid sequence or fragment referred to herein, any one or more of amino acids can be removed, substituted, i.e. replaced by some other amino acid(s) as long as the desired epitopes are not adversely affected by such changes in the structure of the amino acid. Indeed this is quite commonly found in that the amino acid sequence of certain types of M proteins such as type M5 which originates from different strains of M5 (and also come from different origins and/or at different times) may have different amino acids substitutions, i.e. constitution. This has been shown for several such M proteins. Reference to that effect should be made to Miller et al., *J. Biol. Chem.*, 263: 5668 (1988) "Antigenic Variation Among Group A Streptococcal M Proteins: Nucleotide Sequence of the Serotype 5M Protein Gene and its Relationship with Genes Encoding Types 1, 6 and 24 Proteins" and also see Dale et al., *J. Exp. Med.*, 163:1191–1202 (1986), "Localization of Protective Epitopes of the Amino Terminus of Type 5 Streptococcal M Protein".

As has been described the N-terminal segment which is free of tissue cross-reactive epitopes can range from 10 to 115 amino acids and as an average be about 35 amino acids depending on the particular M protein type.

Accordingly, any single fragment of sub-unit constituting the hybrid gene and hence the expressed hybrid protein can be constructed to have a number of amino acid substitutions so as to contains such amino acid substitutions from one strain and for instance, two or more substitutions of another strain of the same serotype. Thus, functionally the antibodies generated would react optimally from and with all the strains of the particular type 5M protein.

It is therefore an important concept in this invention that when reference is made to a particular serotype (i.e. of anyone of the known or to be discovered serotypes e.g., 1–82) reference is not intended to one single type or strain such as that of M5-M6-M19-M24, but to the various strains of such serotypes which may as described, have amino acid variants. Thus, not only is the fundamental concept of the invention to provide a multivalent vaccine against different serotypes, but also different strains within that particular serotype.

Likewise, the nucleotide sequences can be so modified to code for the desired immunobiologically functionally equivalent amino acid sequences. Similarly, it is within the scope of the invention that due to degeneracy of the genetic code DNA sequences be constructed or used that encode and express the desired amino acid fragments in a selected organism transformed (or transfected) with the selected self replicating vehicle.

As has been described herein the invention is not limited to a particular maximum of multivalent hybrid gene or expressed multivalent vaccine by any specific number of serotypes. Since however there appear to be practical limits, it had been suggested that cocktail or mixture of appropriately sized multivalent hybrids be constructed.

Another aspect of the present invention are hybrid or fusion genes which have been constructed which encode the antigens of the present invention. The fusion genes code for the antigens of the invention, constituted as described above, of amino acid fragments linked to the selected carrier. The genes are inserted into suitable self-replicating vehicles, like plasmids. The plasmids containing the genes are then used to transform nonvirulent microorganisms. The transformed microorganisms express the hybrid or fusion protein antigens which are capable of eliciting opsonic and/or protective antibodies against serotypes of Group A streptococcus in immunized mammals, without eliciting cross-reactive antibodies to mammalian heart tissue antigens.

The compositions of the invention can be administered by any suited route, including orally and nasally. They can be dispersed in an appropriate propellant, as for nasal administration.

The therapeutic compositions of the present invention may also be administered parenterally. Mammals, in particular humans, immunized parenterally with a sufficient amount of the therapeutic composition of the present invention develop opsonic and/or protective antibodies directed to the epitopes of the hybrid streptococcal M protein antigen. Non-limiting examples of such parenteral routes of administration are intracutaneous and intramuscular.

For intracutaneous injection, 100–300 μg of hybrid antigen emulsified in complete or incomplete Freund's adjuvant was administered in a mammal. A booster injection of about the same dose in saline was administered about one month later. Blood was obtained prior to the first injection and at two-week intervals thereafter for eight weeks.

A topical method of administration is also provided, namely intranasal. For intranasal administration, a mammal received about 50 μg to about 10 mg of purified antigen in an appropriate diluent for administration. Such method may be particularly well suited when the vaccine is constructed to evoke secretory or mucosal immunity since nasopharyngeal infection is a common infection in humans.

In accordance with the invention, the therapeutic composition may be administered singly in series or advantageously in a mixture or cocktail of multiple compositions to elicit broad spectrum immunity versus Group A streptococci.

The vaccine compositions of the invention which include the antigens of the invention may be adminsitered as disclosed in U.S. Pat. No. 5,124,153 to BEachey et al., which is incorrporated herein by reference and optionally, biologically acceptable diluents or adjuvant. The compositions are suitable for eliciting opsonic and/or protective antibodies to serotypes of M protein of Group A streptococcus. The administered compositions of the present invention elicit such antibodies, without eliciting cross-reactive antibodies to mammalian heart tissue antigens.

The plasmids which encode the M protein hybrid genes of the present invention may be cloned first and expressed in *Escherichia coli*. Any other enteric bacilli of the coliform group such as Klebsiella or Enterobacter can be used, but normally *E. coli* is preferred. The plasmid carrying the hybrid M gene is isolated and purified and then a construct is built to transform the desired avirulent bacteria, such as the araA-*S. typhimurium* (SL3261). This mutant strain exhibits a nutritional marker both for PABA and 2,3-DHB. See Brown et al., (in Beachey patent). Another desired specie of *S. typhimurium* is recA-*S. typhimurium*, particularly strain Ty21a. See Clements, et al., "Construction of a Potential Live Aro Vaccine for typhoid type fever and cholorea-*E. coli*-related diarrheas", *Infect. Immun.*, 46:564–9 (1984). Also see the other references cited in the above cited Brown, et al., article, which are also incorporated herein by reference. Vectors that can be transformed in host cells of other gram negative bacteria such as of the Enterobacteriaceae genus (such as Shigella and Klebsiella like (*Klebsiella pneumonia*; Enterobacter like *Enterobacter aerogenes*). Salmonellae, such as *Salmonella arizona*, and Citrobacter may be used if appropriately rendered non-virulent or attenuated. Common Salmonella species which may be used when attenuated and rendered non-virulent include the following: *S. paratyphi* A, *S. schottmulleri, S. typhimurium, S. paratyphi* C, *S. choleraesuis, S. Montevideo, S. newport, S. typhi, S. enteritidis, S. gallinarum*, and *S. anatum.*

There may also be used as host bacteria of the Streptococcus genus which are non-virulent or which have been made non-virulent or attenuated, including streptococci of the immunological groups A-O generally other than A. Suitable Streptococci which can be used as bacterial host include *S. cremoris, S. faecalis, S. salivarius, S. mitior, S. mitis, S. mutans* and *S. sanguis*. Particularly preferred are *S. sanguis, S. mutans*, which is non-cariogenic.

Additional appropriate microorganisms which may be attenuated and transformed in accordance with the invention are known. Reference may be made to Davis, et al., *Microbiology*, (Harper & Row, Second edition, 1973).

Generally any enteric bacterium may serve as the host bacterium. It is preferable that the host bacterium only survive in the subject long enough to elicit the opsonic response, but generally any bacterial strain that has been attenuated so as not to colonize yet still multiply to a limited degree to elicit antibodies to the protein antigen of the present invention can be used. In a preferred embodiment of the invention the $Aro^-$ strain of *S. typhimurium* is used, which requires two metabolites not found in mammalian tissues, PABA and 2,3-DHB. As a result, the inoculated bacteria die after several generations from a lack of these metabolites. See Hoiseth and Stocker, (in Beachey patent). However, any mutated microbial agent with a metabolic deficiency for nutritional compounds not found in the tissues of the subject to be immunized, or one so made by genetic manipulations, may be employed. The expression of the hybrid gene is confined almost exclusively to cytoplasmic compartment.

In accordance with the present invention, general molecular biology methods are used. Any suitable plasmid or bacteriophage cloning vector may be selected. The vector should have an origin of replication that is functional in the intended microbial host cells, and a selectable marker (such as an antibiotic resistance gene) to aid in identification of host cells that have been transformed with the vector. It should be able to accept inserted DNA fragments and still replicate normally. Preferably, the vector comprises one or more unique restriction endonuclease recognition sites at which hybrid DNA fragments can be inserted without destroying the vector's ability to replicate.

Suitable cloning vectors include phage derivatives such as lambda gt11 (Young and Davis, *Proc. Natl. Acad. Sci. USA*, 80, 1194–1198 (1983)), the various phage M13-derived vectors such as N13mp9 (commercially available from Bethesda Research Labs), plasmids such as pBR322, and many others (Old and Primose, *Principies of Gene Manipulation*, 2nd Ed., University of California, Press, 32–35 and 46–47 (1981)). The streptococcal DNA is inserted into the cloning vector by such standard methods as homopolymeric tailing or by using linker molecules.

In connection with the invention as described, the PCR method and other molecular biology and immunology methods and materials are used. But for the method for synthesizing particular fragments in the pre-selected sequence and orientation, the PCR method and other materials used herein are described in several general standard texts and laboratory manuals. For instance, Sambrook, section 14, in vitro Amplification of DNA by PCR; Ausbel Protocols Molecular Biology, Section 15; for protein expression see same, section 16; for prokaryote and eukaryote expression vectors, see Sambrook, Section 1.7; Protocols Molecular, Section 1, e.g. *E. coli* Plasmids, listing numerous available plasmids. For other suitable vectors for molecular cloning, see Perbal (2nd Ed.), Section 6, which lists for instance, cloning vectors desired from pBR322 (used herein). For material, protocols, etc. in immunology, see in general Current Protocols, Immunology; also see Section 7 for Immunologic Studies in Humans and Section 8 for Isolation and Analysis of Proteins. The ATCC Catalogue of Bacteria and Phages lists suitable microorganisms. For a catalogue of Yeasts, see ATCC Catalogue of Yeast (1990), 18th Ed. For available Recombinant DNA Materials (Hosts, Libraries, Vectors, Clones, etc.), see ATCC catalogue of Recombinant DNA Materials 2nd Ed. (1991).

Another worthwhile publication is Immunology of Proteins, Atassi (vol. 3), Plenium Press (1979).

This invention makes a significant contribution to the medical arts. It is contemplated to be within the scope of the invention that substantially the same results be obtained by substantially the same means operating or performing in substantially the same manner as described herein.

One skilled in the art may refer to the below listed bibliography which is incorporated herein by reference.

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
       (A) LENGTH: 861 base pairs
       (B) TYPE: nucleic acid
       (C) STRANDEDNESS: double
       (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
       (A) ORGANISM: Streptococcus pyogenes (ix) FEATURE:
       (A) NAME/KEY: CDS
       (B) LOCATION: 1..861

(xi) SEQUENCE DESCRIPTION: SEQ ID NO:1:

```
ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15

CGT GCT GAC AAG TTT GAG ATA GAA AAC AAT ACG TTA AAA CTT AAG AAT        96
Arg Ala Asp Lys Phe Glu Ile Glu Asn Asn Thr Leu Lys Leu Lys Asn
                20                  25                  30

AGT GAC TTA AGT TTT AAT AAT AAA GCG TTA AAA GAT CAT AAT GAT GAG       144
Ser Asp Leu Ser Phe Asn Asn Lys Ala Leu Lys Asp His Asn Asp Glu
            35                  40                  45

TTA ACT GAA GAG TTG AGT AAT GCT AAA GAG AAA CTA CGT AAA AAT GAT       192
Leu Thr Glu Glu Leu Ser Asn Ala Lys Glu Lys Leu Arg Lys Asn Asp
        50                  55                  60

AAA TCA CTA TCT GAA AAA GCT AGT AAA ATT CAA GAA TTA GAG GCA CGT       240
Lys Ser Leu Ser Glu Lys Ala Ser Lys Ile Gln Glu Leu Glu Ala Arg
 65                  70                  75                  80

AAG GCT GAT CTT GAA AAA GCA TTA GAA GGC GCA ATG AAT TTT TCA ACA       288
Lys Ala Asp Leu Glu Lys Ala Leu Glu Gly Ala Met Asn Phe Ser Thr
                85                  90                  95

GCG GAT TCA GCT AAA ATC AAA ACC TTA GAA GCA GAG AAA GCT GCT TTA       336
Ala Asp Ser Ala Lys Ile Lys Thr Leu Glu Ala Glu Lys Ala Ala Leu
```

```
GCG GCA CGT AAG GCT GAT CTT GAA AAA GCA TTA GAA GGC GCA ATG AAC       384
Ala Ala Arg Lys Ala Asp Leu Glu Lys Ala Leu Glu Gly Ala Met Asn
            115                 120                 125

TTT TCA ACA GCG GAT TCA GCT AAA ATC AAA ACC TTA GAA GCA GAG AAA       432
Phe Ser Thr Ala Asp Ser Ala Lys Ile Lys Thr Leu Glu Ala Glu Lys
130                 135                 140

GCT GCT TTA GAG GCA CGC CAG GCT GAA CTT GAA AAA GCA TTA GAA GGC       480
Ala Ala Leu Glu Ala Arg Gln Ala Glu Leu Glu Lys Ala Leu Glu Gly
145                 150                 155                 160

GCA ATG AAT TTT TCA ACA GCG GAT TCA GCT AAA ATC AAA ACC TTA GAA       528
Ala Met Asn Phe Ser Thr Ala Asp Ser Ala Lys Ile Lys Thr Leu Glu
            165                 170                 175

GCA GAG AAA GCT GCT TTA GCG GCA CGT AAG GCT GAT CTT GAA AAA GCA       576
Ala Glu Lys Ala Ala Leu Ala Ala Arg Lys Ala Asp Leu Glu Lys Ala
            180                 185                 190

TTA GAA GGC GCA ATG AAC TTT TCA ACA GCG GAT TCA GCT AAA ATC AAA       624
Leu Glu Gly Ala Met Asn Phe Ser Thr Ala Asp Ser Ala Lys Ile Lys
            195                 200                 205

ACC TTA GAA GCA GAG AAA GCT GCT TTA GAG GCA CGC CAG GCT GAA CTT       672
Thr Leu Glu Ala Glu Lys Ala Ala Leu Glu Ala Arg Gln Ala Glu Leu
    210                 215                 220

GAA AAA GCA TTA GAA GGC GCA ATG AAT TTT TCA ACA GCG GAT TCA GCT       720
Glu Lys Ala Leu Glu Gly Ala Met Asn Phe Ser Thr Ala Asp Ser Ala
225                 230                 235                 240

AAA ATC AAA ACC TTA GAA GCA GAG AAA GCT GCT TTG GAG GCA GAG AAA       768
Lys Ile Lys Thr Leu Glu Ala Glu Lys Ala Ala Leu Glu Ala Glu Lys
                245                 250                 255

GCT GAT CTT GAA GGA TCC GCC GTG ACT AGG GGT ACA ATA AAT GAC CCG       816
Ala Asp Leu Glu Gly Ser Ala Val Thr Arg Gly Thr Ile Asn Asp Pro
            260                 265                 270

CAA GTC GAC AGA GTG TTT CCT AGG GGG ACG GTA GAA AAC CCG GAC           861
Gln Val Asp Arg Val Phe Pro Arg Gly Thr Val Glu Asn Pro Asp
    275                 280                 285

(2) INFORMATION FOR SEQ ID NO:2:

(i) SEQUENCE CHARACTERISTICS:
        (A) LENGTH: 287 amino acids
        (B) TYPE: amino acid
        (D) TOPOLOGY: linear (ii) MOLECULE TYPE: protein (xi) SEQUENCE DESCRIPTION: SEQ ID NO:2:

Met Val Ala Thr Arg Ser Gln Thr Asp Thr Leu Glu Lys Val Gln Glu
1               5                   10                  15

Arg Ala Asp Lys Phe Glu Ile Glu Asn Asn Thr Leu Lys Leu Lys Asn
                20                  25                  30

Ser Asp Leu Ser Phe Asn Asn Lys Ala Leu Lys Asp His Asn Asp Glu
            35                  40                  45

Leu Thr Glu Glu Leu Ser Asn Ala Lys Glu Lys Leu Arg Lys Asn Asp
        50                  55                  60

Lys Ser Leu Ser Glu Lys Ala Ser Lys Ile Gln Glu Leu Glu Ala Arg
65                  70                  75                  80

Lys Ala Asp Leu Glu Lys Ala Leu Glu Gly Ala Met Asn Phe Ser Thr
                85                  90                  95

Ala Asp Ser Ala Lys Ile Lys Thr Leu Glu Ala Glu Lys Ala Ala Leu
            100                 105                 110
```

```
Ala Ala Arg Lys Ala Asp Leu Glu Lys Ala Leu Glu Gly Ala Met Asn
        115                 120                 125

Phe Ser Thr Ala Asp Ser Ala Lys Ile Lys Thr Leu Glu Ala Glu Lys
        130                 135             140

Ala Ala Leu Glu Ala Arg Gln Ala Glu Leu Glu Lys Ala Leu Glu Gly
145                 150                 155                 160

Ala Met Asn Phe Ser Thr Ala Asp Ser Ala Lys Ile Lys Thr Leu Glu
                165                 170                 175

Ala Glu Lys Ala Ala Leu Ala Ala Arg Lys Ala Asp Leu Glu Lys Ala
            180                 185                 190

Leu Glu Gly Ala Met Asn Phe Ser Thr Ala Asp Ser Ala Lys Ile Lys
        195                 200                 205

Thr Leu Glu Ala Glu Lys Ala Ala Leu Glu Ala Arg Gln Ala Glu Leu
        210                 215                 220

Glu Lys Ala Leu Glu Gly Ala Met Asn Phe Ser Thr Ala Asp Ser Ala
225                 230                 235                 240

Lys Ile Lys Thr Leu Glu Ala Glu Lys Ala Ala Leu Glu Ala Glu Lys
                245                 250                 255

Ala Asp Leu Glu Gly Ser Ala Val Thr Arg Gly Thr Ile Asn Asp Pro
            260                 265                 270

Gln Val Asp Arg Val Phe Pro Arg Gly Thr Val Glu Asn Pro Asp
        275                 280                 285

(2) INFORMATION FOR SEQ ID NO:3:

(i) SEQUENCE CHARACTERISTICS:
        (A) LENGTH: 741 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (ix) FEATURE:
        (A) NAME/KEY: CDS
        (B) LOCATION: 1..741

(xi) SEQUENCE DESCRIPTION: SEQ ID NO:3:

ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15

CGT GCT GAC AAG TTT GAG ATA GAA AAC AAT ACG TTA AAA CTT AAG AAT        96
Arg Ala Asp Lys Phe Glu Ile Glu Asn Asn Thr Leu Lys Leu Lys Asn
             20                  25                  30

AGT GAC TTA AGT TTT AAT AAT AAA GCG TTA AAA GAT CAT AAT GAT GAG       144
Ser Asp Leu Ser Phe Asn Asn Lys Ala Leu Lys Asp His Asn Asp Glu
         35                  40                  45

TTA ACT GAA GAG TTG AGT AAT GCT AAA GAG AAA CTA CGT AAA AAT GAT       192
Leu Thr Glu Glu Leu Ser Asn Ala Lys Glu Lys Leu Arg Lys Asn Asp
     50                  55                  60

AAA TCA CTA TCT GAA AAA GCT AGT AAA AAT CAA GAA TTA GAG GCA CGT       240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA       288
Lys Ala Asp Leu Glu Lys Ala Leu Glu Gly Ala Met Asn Phe Ser Thr
```

```
            85                    90                    95
GCG GAT TCA GCT AAA ATC AAA ACC TTA GAA GCA GAG AAA GCT GAT CTT    336
Ala Asp Ser Ala Lys Ile Lys Thr Leu Glu Ala Glu Lys Ala Asp Leu
        100                 105                 110

GAA GGA TCC GCC GTG ACT AGG GGT ACA ATA AAT GAC CCG CAA AGA GCA    384
Glu Gly Ser Ala Val Thr Arg Gly Thr Ile Asn Asp Pro Gln Arg Ala
            115                 120                 125

AAA GAA GCT CTT GAC AAG TAT GAG CTA GAA AAC CAT GAC TTA AAA ACT    432
Lys Glu Ala Leu Asp Lys Tyr Glu Leu Glu Asn His Asp Leu Lys Thr
    130                 135                 140

AAG AAT GAA GGG TTA AAA ACT GAG AAT GAA GGG TTA AAA ACT GAG AAT    480
Lys Asn Glu Gly Leu Lys Thr Glu Asn Glu Gly Leu Lys Thr Glu Asn
145                 150                 155                 160

GAA GGG TTA AAA ACT GAG AAT GAA GGG TTA AAA ACT GAG GTC GAC AGA    528
Glu Gly Leu Lys Thr Glu Asn Glu Gly Leu Lys Thr Glu Val Asp Arg
                165                 170                 175

GTG TTT CCT AGG GGG ACG GTA GAA AAC CCG GAC AAA GCA CGA GAA CTT    576
Val Phe Pro Arg Gly Thr Val Glu Asn Pro Asp Lys Ala Arg Glu Leu
            180                 185                 190

CTT AAC AAG TAT GAC GTA GAG AAC TCT ATG TTA CAA GCT AAT AAT GAC    624
Leu Asn Lys Tyr Asp Val Glu Asn Ser Met Leu Gln Ala Asn Asn Asp
                195                 200                 205

AAG TTA CCA TGG AGA GTG CGT TAT ACT AGG CAT ACG CCA GAA GAT AAG    672
Lys Leu Pro Trp Arg Val Arg Tyr Thr Arg His Thr Pro Glu Asp Lys
    210                 215                 220

CTA AAA AAA ATT ATT GAC GAT CTT GAC GCA AAA GAA CAT GAA TTA CAA    720
Leu Lys Lys Ile Ile Asp Asp Leu Asp Ala Lys Glu His Glu Leu Gln
225                 230                 235                 240

CAA CAG AAT GAG AAG TTA TCT                                        741
Gln Gln Asn Glu Lys Leu Ser
                245

(2) INFORMATION FOR SEQ ID NO:4:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:4:

Met Val Ala Thr Arg Ser Gln Thr Asp Thr Leu Glu Lys Val Gln Glu
  1               5                  10                  15

Arg Ala Asp Lys Phe Glu Ile Glu Asn Asn Thr Leu Lys Leu Lys Asn
            20                  25                  30

Ser Asp Leu Ser Phe Asn Asn Lys Ala Leu Lys Asp His Asn Asp Glu
        35                  40                  45

Leu Thr Glu Glu Leu Ser Asn Ala Lys Glu Lys Leu Arg Lys Asn Asp
    50                  55                  60

Lys Ser Leu Ser Glu Lys Ala Ser Lys Asn Gln Glu Leu Glu Ala Arg
 65                 70                  75                  80

Lys Ala Asp Leu Glu Lys Ala Leu Glu Gly Ala Met Asn Phe Ser Thr
            85                  90                  95

Ala Asp Ser Ala Lys Ile Lys Thr Leu Glu Ala Glu Lys Ala Asp Leu
            100                 105                 110

Glu Gly Ser Ala Val Thr Arg Gly Thr Ile Asn Asp Pro Gln Arg Ala
            115                 120                 125

Lys Glu Ala Leu Asp Lys Tyr Glu Leu Glu Asn His Asp Leu Lys Thr
```

```
            130                 135                 140
Lys Asn Glu Gly Leu Lys Thr Glu Asn Glu Gly Leu Lys Thr Glu Asn
145                 150                 155                 160

Glu Gly Leu Lys Thr Glu Asn Glu Gly Leu Lys Thr Glu Val Asp Arg
                165                 170                 175

Val Phe Pro Arg Gly Thr Val Glu Asn Pro Asp Lys Ala Arg Glu Leu
                180                 185                 190

Leu Asn Lys Tyr Asp Val Glu Asn Ser Met Leu Gln Ala Asn Asn Asp
                195                 200                 205

Lys Leu Pro Trp Arg Val Arg Tyr Thr Arg His Thr Pro Glu Asp Lys
                210                 215                 220

Leu Lys Lys Ile Ile Asp Asp Leu Asp Ala Lys Glu His Glu Leu Gln
225                 230                 235                 240

Gln Gln Asn Glu Lys Leu Ser
                245

(2) INFORMATION FOR SEQ ID NO:5:

(i) SEQUENCE CHARACTERISTICS:
        (A) LENGTH: 822 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (ix) FEATURE:
        (A) NAME/KEY: CDS
        (B) LOCATION: 1..822

(xi) SEQUENCE DESCRIPTION: SEQ ID NO:5:

ATG GTC GCG ACT AGG TCT CAG ACA GAT ACT CTG GAA AAA GTA CAA GAA       48
Met Val Ala Thr Arg Ser Gln Thr Asp Thr Leu Glu Lys Val Gln Glu
  1               5                  10                  15

CGT GCT GAC AAG TTT GAG ATA GAA AAC AAT ACG TTA AAA CTT AAG AAT       96
Arg Ala Asp Lys Phe Glu Ile Glu Asn Asn Thr Leu Lys Leu Lys Asn
                 20                  25                  30

AGT GAC TTA AGT TTT AAT AAT AAA GCG TTA AAA GAT CAT AAT GAT GAG      144
Ser Asp Leu Ser Phe Asn Asn Lys Ala Leu Lys Asp His Asn Asp Glu
             35                  40                  45

TTA ACT GAA GAG TTG AGT AAT GCT AAA GAG AAA CTA CGT AAA AAT GAT      192
Leu Thr Glu Glu Leu Ser Asn Ala Lys Glu Lys Leu Arg Lys Asn Asp
         50                  55                  60

AAA TCA CTA TCT GAA AAA GCT AGT AAA AAT CAA GAA TTA GAG GCA CGT      240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA      288
Lys Ala Asp Leu Glu Lys Ala Leu Glu Gly Ala Met Asn Phe Ser Thr
                     85                  90                  95

GCG GAT TCA GCT AAA ATC AAA ACC TTA GAA GCA GAG AAA GCT GAT CTT      336
Ala Asp Ser Ala Lys Ile Lys Thr Leu Glu Ala Glu Lys Ala Asp Leu
                100                 105                 110

GAA GGA TCC CCA GGA AAC CCA GCT GTT CCA GGA TCC GCC GTG ACT AGG      384
Glu Gly Ser Pro Gly Asn Pro Ala Val Pro Gly Ser Ala Val Thr Arg
            115                 120                 125
```

```
GGT ACA ATA AAT GAC CCG CAA AGA GCA AAA GAA GCT CTT GAC AAG TAT       432
Gly Thr Ile Asn Asp Pro Gln Arg Ala Lys Glu Ala Leu Asp Lys Tyr
        130                 135                 140

GAG CTA GAA AAC CAT GAC TTA AAA ACT AAG AAT GAA GGG TTA AAA ACT       480
Glu Leu Glu Asn His Asp Leu Lys Thr Lys Asn Glu Gly Leu Lys Thr
145                 150                 155                 160

GAG AAT GAA GGG TTA AAA ACT GAG AAT GAA GGG TTA AAA ACT GAG AAT       528
Glu Asn Glu Gly Leu Lys Thr Glu Asn Glu Gly Leu Lys Thr Glu Asn
                165                 170                 175

GAA GGG TTA AAA ACT GAG GTC GAC CCA GGA AAC CCA GCT GTT CCA GTC       576
Glu Gly Leu Lys Thr Glu Val Asp Pro Gly Asn Pro Ala Val Pro Val
        180                 185                 190

GAC AGA GTG TTT CCT AGG GGG ACG GTA GAA AAC CCG GAC AAA GCA CGA       624
Asp Arg Val Phe Pro Arg Gly Thr Val Glu Asn Pro Asp Lys Ala Arg
            195                 200                 205

GAA CTT CTT AAC AAG TAT GAC GTA GAG AAC TCT ATG TTA CAA GCT AAT       672
Glu Leu Leu Asn Lys Tyr Asp Val Glu Asn Ser Met Leu Gln Ala Asn
210                 215                 220

AAT GAC AAG TTA CCA TGG CCA GGA AAC CCA GCT GTT CCA CCA TGG AGA       720
Asn Asp Lys Leu Pro Trp Pro Gly Asn Pro Ala Val Pro Pro Trp Arg
225                 230                 235                 240

GTG CGT TAT ACT AGG CAT ACG CCA GAA GAT AAG CTA AAA AAA ATT ATT       768
Val Arg Tyr Thr Arg His Thr Pro Glu Asp Lys Leu Lys Lys Ile Ile
                245                 250                 255

GAC GAT CTT GAC GCA AAA GAA CAT GAA TTA CAA CAA CAG AAT GAG AAG       816
Asp Asp Leu Asp Ala Lys Glu His Glu Leu Gln Gln Gln Asn Glu Lys
        260                 265                 270

TTA TCT                                                               822
Leu Ser
```

(2) INFORMATION FOR SEQ ID NO:6:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Ala Thr Arg Ser Gln Thr Asp Thr Leu Glu Lys Val Gln Glu
1               5                   10                  15

Arg Ala Asp Lys Phe Glu Ile Glu Asn Asn Thr Leu Lys Leu Lys Asn
            20                  25                  30

Ser Asp Leu Ser Phe Asn Asn Lys Ala Leu Lys Asp His Asn Asp Glu
        35                  40                  45

Leu Thr Glu Glu Leu Ser Asn Ala Lys Glu Lys Leu Arg Lys Asn Asp
    50                  55                  60

Lys Ser Leu Ser Glu Lys Ala Ser Lys Asn Gln Glu Leu Glu Ala Arg
65                  70                  75                  80

Lys Ala Asp Leu Glu Lys Ala Leu Glu Gly Ala Met Asn Phe Ser Thr
                85                  90                  95

Ala Asp Ser Ala Lys Ile Lys Thr Leu Glu Ala Glu Lys Ala Asp Leu
            100                 105                 110

Glu Gly Ser Pro Gly Asn Pro Ala Val Pro Gly Ser Ala Val Thr Arg
        115                 120                 125

Gly Thr Ile Asn Asp Pro Gln Arg Ala Lys Glu Ala Leu Asp Lys Tyr
    130                 135                 140

Glu Leu Glu Asn His Asp Leu Lys Thr Lys Asn Glu Gly Leu Lys Thr
```

```
                        145                 150                 155                 160
   Glu Asn Glu Gly Leu Lys Thr Glu Asn Glu Gly Leu Lys Thr Glu Asn
                    165                 170                 175

Glu Gly Leu Lys Thr Glu Val Asp Pro Gly Asn Pro Ala Val Pro Val
               180                 185                 190

Asp Arg Val Phe Pro Arg Gly Thr Val Glu Asn Pro Asp Lys Ala Arg
           195                 200                 205

Glu Leu Leu Asn Lys Tyr Asp Val Glu Asn Ser Met Leu Gln Ala Asn
       210                 215                 220

Asn Asp Lys Leu Pro Trp Pro Gly Asn Pro Ala Val Pro Pro Trp Arg
   225                 230                 235                 240

Val Arg Tyr Thr Arg His Thr Pro Glu Asp Lys Leu Lys Lys Ile Ile
                   245                 250                 255

Asp Asp Leu Asp Ala Lys Glu His Glu Leu Gln Gln Gln Asn Glu Lys
                   260                 265                 270

Leu Ser (2) INFORMATION FOR SEQ ID NO:7:

(i) SEQUENCE CHARACTERISTICS:
         (A) LENGTH: 561 base pairs
         (B) TYPE: nucleic acid
         (C) STRANDEDNESS: double
         (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
         (A) ORGANISM: Streptococcus pyogenes (ix) FEATURE:
         (A) NAME/KEY: CDS
         (B) LOCATION: 1..561

(xi) SEQUENCE DESCRIPTION: SEQ ID NO:7:

ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
  1               5                  10                  15

GTC GCG ACT AGG TCT CAG ACA GAT ACT CTG GAA AAA GTA CAA GAA GTC        96
Val Ala Thr Arg Ser Gln Thr Asp Thr Leu Glu Lys Val Gln Glu Val
                 20                  25                  30

GCG ACT AGG TCT CAG ACA GAT ACT CTG GAA AAA GTA CAA GAA GGA TCC       144
Ala Thr Arg Ser Gln Thr Asp Thr Leu Glu Lys Val Gln Glu Gly Ser
             35                  40                  45

GCC GTG ACT AGG GGT ACA ATA AAT GAC CCG CAA AGA GCA AAA GAA GCC       192
Ala Val Thr Arg Gly Thr Ile Asn Asp Pro Gln Arg Ala Lys Glu Ala
         50                  55                  60

GTG ACT AGG GGT ACA ATA AAT GAC CCG CAA AGA GCA AAA GAA GCC GTG       240
Val Thr Arg Gly Thr Ile Asn Asp Pro Gln Arg Ala Lys Glu Ala Val
     65                  70                  75                  80

ACT AGG GGT ACA ATA AAT GAC CCG CAA AGA GCA AAA GAA GTC GAC AGA       288
Thr Arg Gly Thr Ile Asn Asp Pro Gln Arg Ala Lys Glu Val Asp Arg
                 85                  90                  95

GTG TTT CCT AGG GGG ACG GTA GAA AAC CCG GAC AAA GCA CGA AGA GTG       336
Val Phe Pro Arg Gly Thr Val Glu Asn Pro Asp Lys Ala Arg Arg Val
            100                 105                 110

TTT CCT AGG GGG ACG GTA GAA AAC CCG GAC AAA GCA CGA AGA GTG TTT       384
Phe Pro Arg Gly Thr Val Glu Asn Pro Asp Lys Ala Arg Arg Val Phe
```

```
              115                 120                 125
CCT AGG GGG ACG GTA GAA AAC CCG GAC AAA GCA CGA CCA TGG AGA GTG      432
Pro Arg Gly Thr Val Glu Asn Pro Asp Lys Ala Arg Pro Trp Arg Val
        130                 135                 140

CGT TAT ACT AGG CAT ACG CCA GAA GAT AAG CTA AAA AAA AGA GTG CGT      480
Arg Tyr Thr Arg His Thr Pro Glu Asp Lys Leu Lys Lys Arg Val Arg
145                 150                 155                 160

TAT ACT AGG CAT ACG CCA GAA GAT AAG CTA AAA AAA AGA GTG CGT TAT      528
Tyr Thr Arg His Thr Pro Glu Asp Lys Leu Lys Lys Arg Val Arg Tyr
            165                 170                 175

ACT AGG CAT ACG CCA GAA GAT AAG CTA AAA AAA                          561
Thr Arg His Thr Pro Glu Asp Lys Leu Lys Lys
        180                 185
```

(2) INFORMATION FOR SEQ ID NO:8:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Ala Thr Arg Ser Gln Thr Asp Thr Leu Glu Lys Val Gln Glu
 1               5                  10                  15

Val Ala Thr Arg Ser Gln Thr Asp Thr Leu Glu Lys Val Gln Glu Val
                20                  25                  30

Ala Thr Arg Ser Gln Thr Asp Thr Leu Glu Lys Val Gln Glu Gly Ser
            35                  40                  45

Ala Val Thr Arg Gly Thr Ile Asn Asp Pro Gln Arg Ala Lys Glu Ala
        50                  55                  60

Val Thr Arg Gly Thr Ile Asn Asp Pro Gln Arg Ala Lys Glu Ala Val
65                  70                  75                  80

Thr Arg Gly Thr Ile Asn Asp Pro Gln Arg Ala Lys Glu Val Asp Arg
                85                  90                  95

Val Phe Pro Arg Gly Thr Val Glu Asn Pro Asp Lys Ala Arg Arg Val
               100                 105                 110

Phe Pro Arg Gly Thr Val Glu Asn Pro Asp Lys Ala Arg Arg Val Phe
            115                 120                 125

Pro Arg Gly Thr Val Glu Asn Pro Asp Lys Ala Arg Pro Trp Arg Val
        130                 135                 140

Arg Tyr Thr Arg His Thr Pro Glu Asp Lys Leu Lys Lys Arg Val Arg
145                 150                 155                 160

Tyr Thr Arg His Thr Pro Glu Asp Lys Leu Lys Lys Arg Val Arg Tyr
                165                 170                 175

Thr Arg His Thr Pro Glu Asp Lys Leu Lys Lys
            180                 185
```

(2) INFORMATION FOR SEQ ID NO:9:

(i) SEQUENCE CHARACTERISTICS:
        (A) LENGTH: 918 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
            (A) ORGANISM: Streptococcus pyogenes (ix) FEATURE:
            (A) NAME/KEY: CDS
            (B) LOCATION: 1..915

(xi) SEQUENCE DESCRIPTION: SEQ ID NO:9:

```
ATG GTC GCG ACT AGG TCT CAG ACA GAT ACT CTG GAA AAA GTA CAA GAA      48
Met Val Ala Thr Arg Ser Gln Thr Asp Thr Leu Glu Lys Val Gln Glu
 1               5                  10                  15

GGA TCC GCC GTG ACT AGG GGT ACA ATA AAT GAC CCG CAA AGA GCA AAA      96
Gly Ser Ala Val Thr Arg Gly Thr Ile Asn Asp Pro Gln Arg Ala Lys
            20                  25                  30

GAA GTC GAC AGA GTG TTT CCT AGG GGG ACG GTA GAA AAC CCG GAC AAA     144
Glu Val Asp Arg Val Phe Pro Arg Gly Thr Val Glu Asn Pro Asp Lys
        35                  40                  45

GCA CGA CCA TGG AGA GTG CGT TAT ACT AGG CAT ACG CCA GAA GAT AAG     192
Ala Arg Pro Trp Arg Val Arg Tyr Thr Arg His Thr Pro Glu Asp Lys
    50                  55                  60

CTA AAA AAA CTG CAG AAC AAA ATT TCA GAC GCA AGC CGT AAG GGT CTT     240
Leu Lys Lys Leu Gln Asn Lys Ile Ser Asp Ala Ser Arg Lys Gly Leu
65                  70                  75                  80

CGT CGT GAC TTA GAC GCA TCG CGT GAA GCT AAG AAG CAA TTA GAA GCT     288
Arg Arg Asp Leu Asp Ala Ser Arg Glu Ala Lys Lys Gln Leu Glu Ala
                85                  90                  95

GAA CAC CAA AAA CTT GAA GAA CAA AAC AAG ATT TCA GAA GCA AGT CGC     336
Glu His Gln Lys Leu Glu Glu Gln Asn Lys Ile Ser Glu Ala Ser Arg
            100                 105                 110

AAA GGC CTT CGC CGT GAT TTA GAC GCA TCA CGT GAA GCT AAG AAG CAA     384
Lys Gly Leu Arg Arg Asp Leu Asp Ala Ser Arg Glu Ala Lys Lys Gln
        115                 120                 125

TTA GAA GCT GAA CAA CAA AAA CTT GAA GAA CAA AAC AAG ATT TCA GAA     432
Leu Glu Ala Glu Gln Gln Lys Leu Glu Glu Gln Asn Lys Ile Ser Glu
    130                 135                 140

GCA AGT CGC AAA GGC CTT CGC CGT GAT TTA GAC GCA TCA CGT GAA GCT     480
Ala Ser Arg Lys Gly Leu Arg Arg Asp Leu Asp Ala Ser Arg Glu Ala
145                 150                 155                 160

AAG AAA CAA GTT GAA AAA GCT TTA GAA GAA GCA AAC AGC AAA TTA GCT     528
Lys Lys Gln Val Glu Lys Ala Leu Glu Glu Ala Asn Ser Lys Leu Ala
                165                 170                 175

GCT CTT GAA AAA CTT AAC AAA GAG CTT GAA GAA AGC AAG AAA TTA ACA     576
Ala Leu Glu Lys Leu Asn Lys Glu Leu Glu Glu Ser Lys Lys Leu Thr
            180                 185                 190

GAA AAA GAA AAA GCT GAG CTA CAA GCA AAA CTT GAA GCA GAA GCA AAA     624
Glu Lys Glu Lys Ala Glu Leu Gln Ala Lys Leu Glu Ala Glu Ala Lys
        195                 200                 205

GCA CTC AAA GAA CAA TTA GCA AAA CAA GCT GAA GAA CTT GCA AAA CTA     672
Ala Leu Lys Glu Gln Leu Ala Lys Gln Ala Glu Glu Leu Ala Lys Leu
    210                 215                 220

AGA GCT GGA AAA GCA TCA GAC TCA CAA ACC CCT GAT ACA AAA CCA GGA     720
Arg Ala Gly Lys Ala Ser Asp Ser Gln Thr Pro Asp Thr Lys Pro Gly
225                 230                 235                 240

AAC AAA GCT GTT CCA GGT AAA GGT CAA GCA CCA CAA GCA GGT ACA AAA     768
Asn Lys Ala Val Pro Gly Lys Gly Gln Ala Pro Gln Ala Gly Thr Lys
                245                 250                 255

CCA AAC CAA AAC AAA GCA CCA ATG AAG GAA ACT AAG AGA CAG TTA CCA     816
Pro Asn Gln Asn Lys Ala Pro Met Lys Glu Thr Lys Arg Gln Leu Pro
            260                 265                 270
```

```
TCA ACA GGT GAA ACA GCT AAC CCA TTC TTC ACA GCG GCA GCC CTT ACT       864
Ser Thr Gly Glu Thr Ala Asn Pro Phe Phe Thr Ala Ala Ala Leu Thr
        275                 280                 285

GTT ATG GCA ACA GCT GGA GTA GCA GCA GTT GTA AAA CGC AAA GAA GAA       912
Val Met Ala Thr Ala Gly Val Ala Ala Val Val Lys Arg Lys Glu Glu
290                 295                 300

AAT TAA                                                               918
Asn
305
```

(2) INFORMATION FOR SEQ ID NO:10:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO:10:

```
Met Val Ala Thr Arg Ser Gln Thr Asp Thr Leu Glu Lys Val Gln Glu
1               5                   10                  15

Gly Ser Ala Val Thr Arg Gly Thr Ile Asn Asp Pro Gln Arg Ala Lys
                20                  25                  30

Glu Val Asp Arg Val Phe Pro Arg Gly Thr Val Glu Asn Pro Asp Lys
            35                  40                  45

Ala Arg Pro Trp Arg Val Arg Tyr Thr Arg His Thr Pro Glu Asp Lys
        50                  55                  60

Leu Lys Lys Leu Gln Asn Lys Ile Ser Asp Ala Ser Arg Lys Gly Leu
65                  70                  75                  80

Arg Arg Asp Leu Asp Ala Ser Arg Glu Ala Lys Lys Gln Leu Glu Ala
                85                  90                  95

Glu His Gln Lys Leu Glu Glu Gln Asn Lys Ile Ser Glu Ala Ser Arg
            100                 105                 110

Lys Gly Leu Arg Arg Asp Leu Asp Ala Ser Arg Glu Ala Lys Lys Gln
        115                 120                 125

Leu Glu Ala Glu Gln Gln Lys Leu Glu Glu Gln Asn Lys Ile Ser Glu
130                 135                 140

Ala Ser Arg Lys Gly Leu Arg Arg Asp Leu Asp Ala Ser Arg Glu Ala
145                 150                 155                 160

Lys Lys Gln Val Glu Lys Ala Leu Glu Glu Ala Asn Ser Lys Leu Ala
                165                 170                 175

Ala Leu Glu Lys Leu Asn Lys Glu Leu Glu Ser Lys Lys Leu Thr
            180                 185                 190

Glu Lys Glu Lys Ala Glu Leu Gln Ala Lys Leu Glu Ala Glu Ala Lys
        195                 200                 205

Ala Leu Lys Glu Gln Leu Ala Lys Gln Ala Glu Leu Ala Lys Leu
210                 215                 220

Arg Ala Gly Lys Ala Ser Asp Ser Gln Thr Pro Asp Thr Lys Pro Gly
225                 230                 235                 240

Asn Lys Ala Val Pro Gly Lys Gly Gln Ala Pro Gln Ala Gly Thr Lys
                245                 250                 255

Pro Asn Gln Asn Lys Ala Pro Met Lys Glu Thr Lys Arg Gln Leu Pro
            260                 265                 270

Ser Thr Gly Glu Thr Ala Asn Pro Phe Phe Thr Ala Ala Ala Leu Thr
        275                 280                 285

Val Met Ala Thr Ala Gly Val Ala Ala Val Val Lys Arg Lys Glu Glu
```

Asn
305

(2) INFORMATION FOR SEQ ID NO:11:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:11:

```
Asn Lys Ile Ser Asp Ala Ser Arg Lys Gly Leu Arg Arg Asp Leu Asp
 1               5                  10                  15

Ala Ser Arg Glu Ala Lys Lys Gln Leu Glu Ala Glu His Gln Lys Leu
            20                  25                  30

Glu Glu Gln Asn Lys Ile Ser Glu Ala Ser Arg Lys Gly Leu Arg Arg
        35                  40                  45

Asp Leu Asp Ala Ser Arg Glu Ala Lys Lys Gln Leu Glu Ala Glu Gln
    50                  55                  60

Gln Lys Leu Glu Glu Gln Asn Lys Ile Ser Glu Ala Ser Arg Lys Gly
65                  70                  75                  80

Leu Arg Arg Asp Leu Asp Ala Ser Arg Glu Ala Lys Lys Gln Val Glu
                85                  90                  95

Lys Ala Leu Glu Glu Ala Asn Ser Lys Leu Ala Ala Leu Glu Lys Leu
            100                 105                 110

Asn Lys Glu Leu Glu Ser Lys Lys Leu Thr Glu Lys Glu Lys Ala
        115                 120                 125

Glu Leu Gln Ala Lys Leu Glu Ala Glu Ala Lys Ala Leu Lys Glu Gln
    130                 135                 140

Leu Ala Lys Gln Ala Glu Glu Leu Ala Lys Leu Arg Ala Gly Lys Ala
145                 150                 155                 160

Ser Asp Ser Gln Thr Pro Asp Thr Lys Pro Gly Asn Lys Ala Val Pro
                165                 170                 175

Gly Lys Gly Gln Ala Pro Gln Ala Gly Thr Lys Pro Asn Gln Asn Lys
            180                 185                 190

Ala Pro Met Lys Glu Thr Lys Arg Gln Leu Pro Ser Thr Gly Glu Thr
        195                 200                 205

Ala Asn Pro Phe Phe Thr Ala Ala Leu Thr Val Met Ala Thr Ala
    210                 215                 220

Gly Val Ala Ala Val Lys Arg Lys Glu Glu Asn
225                 230                 235
```

(2) INFORMATION FOR SEQ ID NO:12:

(i) SEQUENCE CHARACTERISTICS:
        (A) LENGTH: 741 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (ix) FEATURE:
      (A) NAME/KEY: CDS
      (B) LOCATION: 1..741

(xi) SEQUENCE DESCRIPTION: SEQ ID NO:12:

| | | | | | | | | | | | | | | | | |
|---|---|---|---|---|---|---|---|---|---|---|---|---|---|---|---|---|
| ATG | AGA | GTG | CGT | TAT | ACT | AGG | CAT | ACG | CCA | GAA | GAT | AAG | CTA | AAA | AAA | 48 |
| Met | Arg | Val | Arg | Tyr | Thr | Arg | His | Thr | Pro | Glu | Asp | Lys | Leu | Lys | Lys | |
| 1 | | | | 5 | | | | | 10 | | | | | 15 | | |
| ATT | ATT | GAC | GAT | CTT | GAC | GCA | AAA | GAA | CAT | GAA | TTA | CAA | CAA | CAG | AAT | 96 |
| Ile | Ile | Asp | Asp | Leu | Asp | Ala | Lys | Glu | His | Glu | Leu | Gln | Gln | Gln | Asn | |
| | | | 20 | | | | | 25 | | | | | 30 | | | |
| GAG | AAG | TTA | TCT | GGA | TCC | AGA | GTG | TTT | CCT | AGG | GGG | ACG | GTA | GAA | AAC | 144 |
| Glu | Lys | Leu | Ser | Gly | Ser | Arg | Val | Phe | Pro | Arg | Gly | Thr | Val | Glu | Asn | |
| | | 35 | | | | | 40 | | | | | 45 | | | | |
| CCG | GAC | AAA | GCA | CGA | GAA | CTT | CTT | AAC | AAG | TAT | GAC | GTA | GAG | AAC | TCT | 192 |
| Pro | Asp | Lys | Ala | Arg | Glu | Leu | Leu | Asn | Lys | Tyr | Asp | Val | Glu | Asn | Ser | |
| | 50 | | | | | 55 | | | | | 60 | | | | | |
| ATG | TTA | CAA | GCT | AAT | AAT | GAC | AAC | TTA | GTC | GAC | GCC | GTG | ACT | AGG | GGT | 240 |
| Met | Leu | Gln | Ala | Asn | Asn | Asp | Asn | Leu | Val | Asp | Ala | Val | Thr | Arg | Gly | |
| 65 | | | | | 70 | | | | | 75 | | | | | 80 | |
| ACA | ATA | AAT | GAC | CCG | CAA | AGA | GCA | AAA | GAA | GCT | CTT | GAC | AAG | TAT | GAG | 288 |
| Thr | Ile | Asn | Asp | Pro | Gln | Arg | Ala | Lys | Glu | Ala | Leu | Asp | Lys | Tyr | Glu | |
| | | | | 85 | | | | | 90 | | | | | 95 | | |
| CTA | GAA | AAC | CAT | GAC | TTA | AAA | ACT | AAG | AAT | GAA | GGG | TTA | AAA | ACT | GAG | 336 |
| Leu | Glu | Asn | His | Asp | Leu | Lys | Thr | Lys | Asn | Glu | Gly | Leu | Lys | Thr | Glu | |
| | | | 100 | | | | | 105 | | | | | 110 | | | |
| AAT | GAA | GGG | TTA | AAA | ACT | GAG | AAT | GAA | GGG | TTA | AAA | ACT | GAG | AAT | GAA | 384 |
| Asn | Glu | Gly | Leu | Lys | Thr | Glu | Asn | Glu | Gly | Leu | Lys | Thr | Glu | Asn | Glu | |
| | | 115 | | | | | 120 | | | | | 125 | | | | |
| GGG | TTA | AAA | ACT | GAG | CCA | TGG | GTC | GCG | ACT | AGG | TCT | CAG | ACA | GAT | ACT | 432 |
| Gly | Leu | Lys | Thr | Glu | Pro | Trp | Val | Ala | Thr | Arg | Ser | Gln | Thr | Asp | Thr | |
| | 130 | | | | | 135 | | | | | 140 | | | | | |
| CTG | GAA | AAA | GTA | CAA | GAA | CGT | GCT | GAC | AAG | TTT | GAG | ATA | GAA | AAC | AAT | 480 |
| Leu | Glu | Lys | Val | Gln | Glu | Arg | Ala | Asp | Lys | Phe | Glu | Ile | Glu | Asn | Asn | |
| 145 | | | | | 150 | | | | | 155 | | | | | 160 | |
| ACG | TTA | AAA | CTT | AAG | AAT | AGT | GAC | TTA | AGT | TTT | AAT | AAT | AAA | GCG | TTA | 528 |
| Thr | Leu | Lys | Leu | Lys | Asn | Ser | Asp | Leu | Ser | Phe | Asn | Asn | Lys | Ala | Leu | |
| | | | | 165 | | | | | 170 | | | | | 175 | | |
| AAA | GAT | CAT | AAT | GAT | GAG | TTA | ACT | GAA | GAG | TTG | AGT | AAT | GCT | AAA | GAG | 576 |
| Lys | Asp | His | Asn | Asp | Glu | Leu | Thr | Glu | Glu | Leu | Ser | Asn | Ala | Lys | Glu | |
| | | | 180 | | | | | 185 | | | | | 190 | | | |
| AAA | CTA | CGT | AAA | AAT | GAT | AAA | TCA | CTA | TCT | GAA | AAA | GCT | AGT | AAA | AAT | 624 |
| Lys | Leu | Arg | Lys | Asn | Asp | Lys | Ser | Leu | Ser | Glu | Lys | Ala | Ser | Lys | Asn | |
| | | 195 | | | | | 200 | | | | | 205 | | | | |
| CAA | GAA | TTA | GAG | GCA | CGT | AAG | GCT | GAT | CTT | GAA | AAA | GCA | TTA | GAA | GGC | 672 |
| Gln | Glu | Leu | Glu | Ala | Arg | Lys | Ala | Asp | Leu | Glu | Lys | Ala | Leu | Glu | Gly | |
| | 210 | | | | | 215 | | | | | 220 | | | | | |
| GCA | ATG | AAT | TTT | TCA | ACA | GCG | GAT | TCA | GCT | AAA | ATC | AAA | ACC | TTA | GAA | 720 |
| Ala | Met | Asn | Phe | Ser | Thr | Ala | Asp | Ser | Ala | Lys | Ile | Lys | Thr | Leu | Glu | |
| 225 | | | | | 230 | | | | | 235 | | | | | 240 | |
| GCA | GAG | AAA | GCT | GAT | CTT | GAA | | | | | | | | | | 741 |
| Ala | Glu | Lys | Ala | Asp | Leu | Glu | | | | | | | | | | |
| | | | 245 | | | | | | | | | | | | | |

(2) INFORMATION FOR SEQ ID NO:13:

(i) SEQUENCE CHARACTERISTICS:
      (A) LENGTH: 247 amino acids
      (B) TYPE: amino acid
      (D) TOPOLOGY: linear -continued (ii) MOLECULE TYPE: protein (xi) SEQUENCE DESCRIPTION: SEQ ID NO:13:

Met Arg Val Arg Tyr Thr Arg His Thr Pro Glu Asp Lys Leu Lys Lys
1               5                   10                  15

Ile Ile Asp Asp Leu Asp Ala Lys Glu His Glu Leu Gln Gln Gln Asn
            20                  25                  30

Glu Lys Leu Ser Gly Ser Arg Val Phe Pro Arg Gly Thr Val Glu Asn
            35                  40                  45

Pro Asp Lys Ala Arg Glu Leu Leu Asn Lys Tyr Asp Val Glu Asn Ser
        50                  55                  60

Met Leu Gln Ala Asn Asn Asp Asn Leu Val Asp Ala Val Thr Arg Gly
65                  70                  75                  80

Thr Ile Asn Asp Pro Gln Arg Ala Lys Glu Ala Leu Asp Lys Tyr Glu
                85                  90                  95

Leu Glu Asn His Asp Leu Lys Thr Lys Asn Glu Gly Leu Lys Thr Glu
            100                 105                 110

Asn Glu Gly Leu Lys Thr Glu Asn Glu Gly Leu Lys Thr Glu Asn Glu
            115                 120                 125

Gly Leu Lys Thr Glu Pro Trp Val Ala Thr Arg Ser Gln Thr Asp Thr
130                 135                 140

Leu Glu Lys Val Gln Glu Arg Ala Asp Lys Phe Glu Ile Glu Asn Asn
145                 150                 155                 160

Thr Leu Lys Leu Lys Asn Ser Asp Leu Ser Phe Asn Asn Lys Ala Leu
                165                 170                 175

Lys Asp His Asn Asp Glu Leu Thr Glu Glu Leu Ser Asn Ala Lys Glu
            180                 185                 190

Lys Leu Arg Lys Asn Asp Lys Ser Leu Ser Glu Lys Ala Ser Lys Asn
            195                 200                 205

Gln Glu Leu Glu Ala Arg Lys Ala Asp Leu Glu Lys Ala Leu Glu Gly
        210                 215                 220

Ala Met Asn Phe Ser Thr Ala Asp Ser Ala Lys Ile Lys Thr Leu Glu
225                 230                 235                 240

Ala Glu Lys Ala Asp Leu Glu
                245

(2) INFORMATION FOR SEQ ID NO:14:

(i) SEQUENCE CHARACTERISTICS:
        (A) LENGTH: 522 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (ix) FEATURE:
        (A) NAME/KEY: CDS
        (B) LOCATION: 1..519

(xi) SEQUENCE DESCRIPTION: SEQ ID NO:14:

ATG GTC GCG ACT AGG TCT CAG ACA GAT ACT CTG GAA AAA GTA CAA GAA          48
Met Val Ala Thr Arg Ser Gln Thr Asp Thr Leu Glu Lys Val Gln Glu
1               5                   10                  15

```
CGT GCT GAC AAG TTT GAG ATA GAA AAC AAT ACG TTA AAA CTT AAG AAT        96
Arg Ala Asp Lys Phe Glu Ile Glu Asn Asn Thr Leu Lys Leu Lys Asn
            20                  25                  30

AGT GAC TTA AGT TTT AAT AAT AAA GCG TTA AAA GAT CAT AAT GAT GAG       144
Ser Asp Leu Ser Phe Asn Asn Lys Ala Leu Lys Asp His Asn Asp Glu
                35                  40                  45

TTA ACT GAA GAG TTG AGT AAT GCT AAA GAG AAA CTA CGT AAA AAT GAT       192
Leu Thr Glu Glu Leu Ser Asn Ala Lys Glu Lys Leu Arg Lys Asn Asp
        50                  55                  60

AAA TCA CTA TCT GAA AAA GCT AGT AAA AAT CAA GAA TTA GAG GCA CGT       240
Lys Ser Leu Ser Glu Lys Ala Ser Lys Asn Gln Glu Leu Glu Ala Arg
 65                  70                  75                  80

AAG GCT GAT CTT GAA AAA GCA TTA GAA GGC GCA ATG AAT TTT TCA ACA       288
Lys Ala Asp Leu Glu Lys Ala Leu Glu Gly Ala Met Asn Phe Ser Thr
                    85                  90                  95

GCG GAT TCA GCT AAA ATC AAA ACC TTA GAA GCA GAG AAA GCT GAT CTT       336
Ala Asp Ser Ala Lys Ile Lys Thr Leu Glu Ala Glu Lys Ala Asp Leu
                100                 105                 110

GAA GGA TCC GCC GTG ACT AGG GGT ACA ATA AAT GAC CCG CAA AGA GCA       384
Glu Gly Ser Ala Val Thr Arg Gly Thr Ile Asn Asp Pro Gln Arg Ala
            115                 120                 125

AAA GAA GCT CTT GAC AAG TAT GAG CTA GAA AAC CAT GAC TTA AAA ACT       432
Lys Glu Ala Leu Asp Lys Tyr Glu Leu Glu Asn His Asp Leu Lys Thr
130                 135                 140

AAG AAT GAA GGG TTA AAA ACT GAG AAT GAA GGG TTA AAA ACT GAG AAT       480
Lys Asn Glu Gly Leu Lys Thr Glu Asn Glu Gly Leu Lys Thr Glu Asn
145                 150                 155                 160

GAA GGG TTA AAA ACT GAG AAT GAA GGG TTA AAA ACT GAG TAA               522
Glu Gly Leu Lys Thr Glu Asn Glu Gly Leu Lys Thr Glu
                165                 170
```

(2) INFORMATION FOR SEQ ID NO:15:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:15:

```
Met Val Ala Thr Arg Ser Gln Thr Asp Thr Leu Glu Lys Val Gln Glu
 1               5                  10                  15

Arg Ala Asp Lys Phe Glu Ile Glu Asn Asn Thr Leu Lys Leu Lys Asn
            20                  25                  30

Ser Asp Leu Ser Phe Asn Asn Lys Ala Leu Lys Asp His Asn Asp Glu
                35                  40                  45

Leu Thr Glu Glu Leu Ser Asn Ala Lys Glu Lys Leu Arg Lys Asn Asp
        50                  55                  60

Lys Ser Leu Ser Glu Lys Ala Ser Lys Asn Gln Glu Leu Glu Ala Arg
 65                  70                  75                  80

Lys Ala Asp Leu Glu Lys Ala Leu Glu Gly Ala Met Asn Phe Ser Thr
                    85                  90                  95

Ala Asp Ser Ala Lys Ile Lys Thr Leu Glu Ala Glu Lys Ala Asp Leu
                100                 105                 110

Glu Gly Ser Ala Val Thr Arg Gly Thr Ile Asn Asp Pro Gln Arg Ala
            115                 120                 125

Lys Glu Ala Leu Asp Lys Tyr Glu Leu Glu Asn His Asp Leu Lys Thr
130                 135                 140
```

```
Lys Asn Glu Gly Leu Lys Thr Glu Asn Glu Gly Leu Lys Thr Glu Asn
145                 150                 155                 160

Glu Gly Leu Lys Thr Glu Asn Glu Gly Leu Lys Thr Glu
                165                 170
```

(2) INFORMATION FOR SEQ ID NO:16:

(i) SEQUENCE CHARACTERISTICS:
        (A) LENGTH: 1029 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pyogenes (ix) FEATURE:
        (A) NAME/KEY: CDS
        (B) LOCATION: 1..1029

(xi) SEQUENCE DESCRIPTION: SEQ ID NO:16:

```
ATG AGA GTG CGT TAT ACT AGG CAT ACG CCA GAA GAT AAG CTA AAA AAA        48
Met Arg Val Arg Tyr Thr Arg His Thr Pro Glu Asp Lys Leu Lys Lys
1               5                   10                  15

ATT ATT GAC GAT CTT GAC GCA AAA GAA CAT GAA TTA CAA CAA CAG AAT        96
Ile Ile Asp Asp Leu Asp Ala Lys Glu His Glu Leu Gln Gln Gln Asn
                20                  25                  30

GAG AAG TTA TCT GGA TCC AGA GTG TTT CCT AGG GGG ACG GTA GAA AAC       144
Glu Lys Leu Ser Gly Ser Arg Val Phe Pro Arg Gly Thr Val Glu Asn
            35                  40                  45

CCG GAC AAA GCA CGA GAA CTT CTT AAC AAG TAT GAC GTA GAG AAC TCT       192
Pro Asp Lys Ala Arg Glu Leu Leu Asn Lys Tyr Asp Val Glu Asn Ser
        50                  55                  60

ATG TTA CAA GCT AAT AAT GAC AAC TTA GTC GAC GCC GTG ACT AGG GGT       240
Met Leu Gln Ala Asn Asn Asp Asn Leu Val Asp Ala Val Thr Arg Gly
65                  70                  75                  80

ACA ATA AAT GAC CCG CAA AGA GCA AAA GAA GCT CTT GAC AAG TAT GAG       288
Thr Ile Asn Asp Pro Gln Arg Ala Lys Glu Ala Leu Asp Lys Tyr Glu
                85                  90                  95

CTA GAA AAC CAT GAC TTA AAA ACT AAG AAT GAA GGG TTA AAA ACT GAG       336
Leu Glu Asn His Asp Leu Lys Thr Lys Asn Glu Gly Leu Lys Thr Glu
            100                 105                 110

AAT GAA GGG TTA AAA ACT GAG AAT GAA GGG TTA AAA ACT GAG AAT GAA       384
Asn Glu Gly Leu Lys Thr Glu Asn Glu Gly Leu Lys Thr Glu Asn Glu
        115                 120                 125

GGG TTA AAA ACT GAG CCA TGG GTC GCG ACT AGG TCT CAG ACA GAT ACT       432
Gly Leu Lys Thr Glu Pro Trp Val Ala Thr Arg Ser Gln Thr Asp Thr
130                 135                 140

CTG GAA AAA GTA CAA GAA CGT GCT GAC AAG TTT GAG ATA GAA AAC AAT       480
Leu Glu Lys Val Gln Glu Arg Ala Asp Lys Phe Glu Ile Glu Asn Asn
145                 150                 155                 160

ACG TTA AAA CTT AAG AAT AGT GAC TTA AGT TTT AAT AAT AAA GCG TTA       528
Thr Leu Lys Leu Lys Asn Ser Asp Leu Ser Phe Asn Asn Lys Ala Leu
                165                 170                 175

AAA GAT CAT AAT GAT GAG TTA ACT GAA GAG TTG AGT AAT GCT AAA GAG       576
Lys Asp His Asn Asp Glu Leu Thr Glu Glu Leu Ser Asn Ala Lys Glu
            180                 185                 190
```

```
AAA CTA CGT AAA AAT GAT AAA TCA CTA TCT GAA AAA GCT AGT AAA AAT       624
Lys Leu Arg Lys Asn Asp Lys Ser Leu Ser Glu Lys Ala Ser Lys Asn
        195                 200                 205

CAA GAA TTA GAG GCA CGT AAG GCT GAT CTT GAA AAA GCA TTA GAA GGC       672
Gln Glu Leu Glu Ala Arg Lys Ala Asp Leu Glu Lys Ala Leu Glu Gly
    210                 215                 220

GCA ATG AAT TTT TCA ACA GCG GAT TCA GCT AAA ATC AAA ACC TTA GAA       720
Ala Met Asn Phe Ser Thr Ala Asp Ser Ala Lys Ile Lys Thr Leu Glu
225                 230                 235                 240

GCA GAG AAA GCT GAT CTT GAA CGA TCG AAC AAA ATT TCA GAC GCA AGC       768
Ala Glu Lys Ala Asp Leu Glu Arg Ser Asn Lys Ile Ser Asp Ala Ser
                245                 250                 255

CGT AAG GGT CTT CGT CGT GAC TTA GAC GCA TCG CGT GAA GCT AAG AAG       816
Arg Lys Gly Leu Arg Arg Asp Leu Asp Ala Ser Arg Glu Ala Lys Lys
            260                 265                 270

CAA TTA GAA GCT GAA CAC CAA AAA CTT GAA GAA CAA AAC AAG ATT TCA       864
Gln Leu Glu Ala Glu His Gln Lys Leu Glu Glu Gln Asn Lys Ile Ser
        275                 280                 285

GAA GCA AGT CGC AAA GGC CTT CGC CGT GAT TTA GAC GCA TCA CGT GAA       912
Glu Ala Ser Arg Lys Gly Leu Arg Arg Asp Leu Asp Ala Ser Arg Glu
    290                 295                 300

GCT AAG AAG CAA TTA GAA GCT GAA CAA CAA AAA CTT GAA GAA CAA AAC       960
Ala Lys Lys Gln Leu Glu Ala Glu Gln Gln Lys Leu Glu Glu Gln Asn
305                 310                 315                 320

AAG ATT TCA GAA GCA AGT CGC AAA GGC CTT CGC CGT GAT TTA GAC GCA      1008
Lys Ile Ser Glu Ala Ser Arg Lys Gly Leu Arg Arg Asp Leu Asp Ala
                325                 330                 335

TCA CGT GAA GCT AAG AAA CAA                                         1029
Ser Arg Glu Ala Lys Lys Gln
            340
```

(2) INFORMATION FOR SEQ ID NO:17:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO:17:

```
Met Arg Val Arg Tyr Thr Arg His Thr Pro Glu Asp Lys Leu Lys Lys
 1               5                  10                  15

Ile Ile Asp Asp Leu Asp Ala Lys Glu His Glu Leu Gln Gln Gln Asn
                20                  25                  30

Glu Lys Leu Ser Gly Ser Arg Val Phe Pro Arg Gly Thr Val Glu Asn
            35                  40                  45

Pro Asp Lys Ala Arg Glu Leu Leu Asn Lys Tyr Asp Val Glu Asn Ser
        50                  55                  60

Met Leu Gln Ala Asn Asn Asp Asn Leu Val Asp Ala Val Thr Arg Gly
65                  70                  75                  80

Thr Ile Asn Asp Pro Gln Arg Ala Lys Glu Ala Leu Asp Lys Tyr Glu
                85                  90                  95

Leu Glu Asn His Asp Leu Lys Thr Lys Asn Glu Gly Leu Lys Thr Glu
            100                 105                 110

Asn Glu Gly Leu Lys Thr Glu Asn Glu Gly Leu Lys Thr Glu Asn Glu
        115                 120                 125

Gly Leu Lys Thr Glu Pro Trp Val Ala Thr Arg Ser Gln Thr Asp Thr
    130                 135                 140
```

```
Leu Glu Lys Val Gln Glu Arg Ala Asp Lys Phe Glu Ile Glu Asn Asn
145                 150                 155                 160

Thr Leu Lys Leu Lys Asn Ser Asp Leu Ser Phe Asn Asn Lys Ala Leu
                165                 170                 175

Lys Asp His Asn Asp Glu Leu Thr Glu Glu Leu Ser Asn Ala Lys Glu
            180                 185                 190

Lys Leu Arg Lys Asn Asp Lys Ser Leu Ser Glu Lys Ala Ser Lys Asn
        195                 200                 205

Gln Glu Leu Glu Ala Arg Lys Ala Asp Leu Glu Lys Ala Leu Glu Gly
210                 215                 220

Ala Met Asn Phe Ser Thr Ala Asp Ser Ala Lys Ile Lys Thr Leu Glu
225                 230                 235                 240

Ala Glu Lys Ala Asp Leu Glu Arg Ser Asn Lys Ile Ser Asp Ala Ser
                245                 250                 255

Arg Lys Gly Leu Arg Arg Asp Leu Asp Ala Ser Arg Glu Ala Lys Lys
            260                 265                 270

Gln Leu Glu Ala Glu His Gln Lys Leu Glu Glu Gln Asn Lys Ile Ser
        275                 280                 285

Glu Ala Ser Arg Lys Gly Leu Arg Arg Asp Leu Asp Ala Ser Arg Glu
290                 295                 300

Ala Lys Lys Gln Leu Glu Ala Glu Gln Lys Leu Glu Glu Gln Asn
305                 310                 315                 320

Lys Ile Ser Glu Ala Ser Arg Lys Gly Leu Arg Arg Asp Leu Asp Ala
                325                 330                 335

Ser Arg Glu Ala Lys Lys Gln
            340

(2) INFORMATION FOR SEQ ID NO:18:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:18:

Asn Lys Ile Ser Asp Ala Ser Arg Lys Gly Leu Arg Arg Asp Leu Asp
1               5                   10                  15

Ala Ser Arg Glu Ala Lys Lys Gln Leu Glu Ala Glu His Gln Lys Leu
            20                  25                  30

Glu Glu Gln Asn Lys Ile Ser Glu Ala Ser Arg Lys Gly Leu Arg Arg
        35                  40                  45

Asp Leu Asp Ala Ser Arg Glu Ala Lys Lys Gln Leu Glu Ala Glu Gln
    50                  55                  60

Gln Lys Leu Glu Glu Gln Asn Lys Ile Ser Glu Ala Ser Arg Lys Gly
65                  70                  75                  80

Leu Arg Arg Asp Leu Asp Ala Ser Arg Glu Ala Lys Lys Gln
                85                  90

(2) INFORMATION FOR SEQ ID NO:19:

(i) SEQUENCE CHARACTERISTICS:
        (A) LENGTH: 204 base pairs
        (B) TYPE: nucleic acid
        (C) STRANDEDNESS: double
        (D) TOPOLOGY: unknown (ii) MOLECULE TYPE: DNA (genomic)
```

```
        (iii) HYPOTHETICAL: NO (iv) ANTI-SENSE: NO (vi) ORIGINAL SOURCE:
             (A) ORGANISM: Streptococcus pyogenes (ix) FEATURE:
             (A) NAME/KEY: CDS
             (B) LOCATION: 1..201

(xi) SEQUENCE DESCRIPTION: SEQ ID NO:19:

ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15

GGA TCC GCC GTG ACT AGG GGT ACA ATA AAT GAC CCG CAA AGA GCA AAA        96
Gly Ser Ala Val Thr Arg Gly Thr Ile Asn Asp Pro Gln Arg Ala Lys
                20                  25                  30

GAA GTC GAC AGA GTG TTT CCT AGG GGG ACG GTA GAA AAC CCG GAC AAA       144
Glu Val Asp Arg Val Phe Pro Arg Gly Thr Val Glu Asn Pro Asp Lys
         35                  40                  45

GCA CGA CCA TGG AGA GTG CGT TAT ACT AGG CAT ACG CCA GAA GAT AAG       192
Ala Arg Pro Trp Arg Val Arg Tyr Thr Arg His Thr Pro Glu Asp Lys
 50                  55                  60

CTA AAA AAA TAA                                                       204
Leu Lys Lys
 65

(2) INFORMATION FOR SEQ ID NO:20:

(i) SEQUENCE CHARACTERISTICS:
             (A) LENGTH: 67 amino acids
             (B) TYPE: amino acid
             (D) TOPOLOGY: linear (ii) MOLECULE TYPE: protein (xi) SEQUENCE DESCRIPTION: SEQ ID NO:20:

Met Val Ala Thr Arg Ser Gln Thr Asp Thr Leu Glu Lys Val Gln Glu
 1               5                  10                  15

Gly Ser Ala Val Thr Arg Gly Thr Ile Asn Asp Pro Gln Arg Ala Lys
                20                  25                  30

Glu Val Asp Arg Val Phe Pro Arg Gly Thr Val Glu Asn Pro Asp Lys
         35                  40                  45

Ala Arg Pro Trp Arg Val Arg Tyr Thr Arg His Thr Pro Glu Asp Lys
 50                  55                  60

Leu Lys Lys
 65

(2) INFORMATION FOR SEQ ID NO:21:

(i) SEQUENCE CHARACTERISTICS:
             (A) LENGTH: 408 base pairs
             (B) TYPE: nucleic acid
             (C) STRANDEDNESS: double
             (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
             (A) ORGANISM: Streptococcus pyogenes
```

```
    (ix) FEATURE:
         (A) NAME/KEY: CDS
         (B) LOCATION: 1..405

(xi) SEQUENCE DESCRIPTION: SEQ ID NO:21:

ATG GTC GCG ACT AGG TCT CAG ACA GAT ACT CTG GAA AAA GTA CAA GAA        48
Met Val Ala Thr Arg Ser Gln Thr Asp Thr Leu Glu Lys Val Gln Glu
 1               5                  10                  15

GGA TCC GCC GTG ACT AGG GGT ACA ATA AAT GAC CCG CAA AGA GCA AAA        96
Gly Ser Ala Val Thr Arg Gly Thr Ile Asn Asp Pro Gln Arg Ala Lys
                20                  25                  30

GAA GTC GAC AGA GTG TTT CCT AGG GGG ACG GTA GAA AAC CCG GAC AAA       144
Glu Val Asp Arg Val Phe Pro Arg Gly Thr Val Glu Asn Pro Asp Lys
            35                  40                  45

GCA CGA CCA TGG AGA GTG CGT TAT ACT AGG CAT ACG CCA GAA GAT AAG       192
Ala Arg Pro Trp Arg Val Arg Tyr Thr Arg His Thr Pro Glu Asp Lys
        50                  55                  60

CTA AAA AAA CTG CAG GAT GCT AGG AGT GTT AAT GGA GAG TTT CCT AGA       240
Leu Lys Lys Leu Gln Asp Ala Arg Ser Val Asn Gly Glu Phe Pro Arg
 65              70                  75                  80

CAT GTT AAA TTA ATC GAT AAC GGT GAT GGT AAT CCT AGG GAA GTT ATA       288
His Val Lys Leu Ile Asp Asn Gly Asp Gly Asn Pro Arg Glu Val Ile
                85                  90                  95

GAA GAT CTT GCA GCA GAA TTC GCA CCT CTT ACT CGA GCT ACA GCA GAC       336
Glu Asp Leu Ala Ala Glu Phe Ala Pro Leu Thr Arg Ala Thr Ala Asp
           100                 105                 110

AAT AAA GAC GAA TTA ATA CGA TCG CAT AGT GAT TTA GTC GCA GAA AAA       384
Asn Lys Asp Glu Leu Ile Arg Ser His Ser Asp Leu Val Ala Glu Lys
       115                 120                 125

CAA GCT TTA GAA GAT TTA GGA TAA                                       408
Gln Ala Leu Glu Asp Leu Gly
       130                 135

(2) INFORMATION FOR SEQ ID NO:22:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:22:

Met Val Ala Thr Arg Ser Gln Thr Asp Thr Leu Glu Lys Val Gln Glu
 1               5                  10                  15

Gly Ser Ala Val Thr Arg Gly Thr Ile Asn Asp Pro Gln Arg Ala Lys
                20                  25                  30

Glu Val Asp Arg Val Phe Pro Arg Gly Thr Val Glu Asn Pro Asp Lys
            35                  40                  45

Ala Arg Pro Trp Arg Val Arg Tyr Thr Arg His Thr Pro Glu Asp Lys
        50                  55                  60

Leu Lys Lys Leu Gln Asp Ala Arg Ser Val Asn Gly Glu Phe Pro Arg
 65              70                  75                  80

His Val Lys Leu Ile Asp Asn Gly Asp Gly Asn Pro Arg Glu Val Ile
                85                  90                  95

Glu Asp Leu Ala Ala Glu Phe Ala Pro Leu Thr Arg Ala Thr Ala Asp
           100                 105                 110

Asn Lys Asp Glu Leu Ile Arg Ser His Ser Asp Leu Val Ala Glu Lys
       115                 120                 125

Gln Ala Leu Glu Asp Leu Gly
```

```
        130                 135
```

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:23:

```
Leu Pro Ser Thr Gly Glu
1               5
```

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:24:

```
GGGAATTCAT GGTCGCGACT AGGTCTCAG                                         29
```

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:25:

```
CGTCTCTTTC GACTAGAACT TCCTAGGCTC                                        30
```

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:26:

```
GATCCGCCGT GACTAGGGGT ACAATAAATG ACCCGCAAG                              39
```

(2) INFORMATION FOR SEQ ID NO:27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:27:

```
GCGGCACTGA TCCCCATGTT ATTTACTGGG CGTTCAGCT                              39
```

(2) INFORMATION FOR SEQ ID NO:28:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:28:

```
TCGACAGAGT GTTTCCTAGG GGGACGGTAG AAAANNNGGA CCTGCAG                47
```

(2) INFORMATION FOR SEQ ID NO:29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:29:

```
GTCTCACAAA GGATCCCCCT GCCATCTTTT GGGCCTGGAC GTCGCCGG               48
```

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:30:

```
GGGAATTCAT GGTCGCGACT AGGTCTCAG                                    29
```

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:31:

```
GGGGATCCTT CAAGATCAGC TTTCTCTGC                                    29
```

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:32:

```
GGGGGGGGAT CCGCCGTGAC TAGGGGTACA                                   30
```

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:33:

```
GGGGGGGTCG ACCTCAGTTT TAACCCTTC                                    29
```

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:34:

```
GGGGGGGTCG ACAGAGTGTT TCCTAGGGGG                                   30
```

(2) INFORMATION FOR SEQ ID NO:35:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:35:

GGGGGGCCAT GGTAAGTTGT CAATAATAGC                    30

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:36:

GGGGGGCCAT GGAGAGTGCG TTATACTAGG                    30

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:37:

GGGGGGCTGC AGAGATAACT TCTCATTCTG                    30

(2) INFORMATION FOR SEQ ID NO:38:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:38:

AGACTGCGTT ATACTAGGCA TACGCCAGAA GATAAGAGAG TGCGTTATAC TAGG      54

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:39:

GGGGGGCCAT GGCTTATCTT CTGGCGTATG                    30

(2) INFORMATION FOR SEQ ID NO:40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:40:

GGGGGGGAAT CCAGAGTCCG TTATACTAGG                    30

TABLE 1

Inhibition of opsonization of types 24, 5, and 6 streptococci by M24-M5-M6 trivalent hybrid M protein.

| Serotype | Antiserum | Inhibitor | Precent Opsonization |
|---|---|---|---|
| M24 | preimmune | — | 6 |
|  | anti-pep M24 | — | 78 |
|  |  | M24-M5-M6 | 0 |
|  |  | pep M24 | 0 |
| M5 | preimmune | — | 6 |
|  | anti SM5(1–15) | — | 64 |
|  |  | M24-M5-M6 | 16 |
|  |  | pep M5 | 6 |
| M6 | preimmune | — | 0 |
|  | anti SM6(1–20) | — | 58 |
|  |  | M24-M5-M6 | 4 |
|  |  | pep M6 | 0 |

TABLE 2

Immunogenicity of M24-M5-M6 trivalent hybrid M protein in rabbits

| Rabbit Number | | M24-M5-M6 | pep M24 | SM5 (1–15)C | pep M5 | SM6 (1–20)C | pep M6 |
|---|---|---|---|---|---|---|---|
| 9140 | Preimmune | <100 | <100 | <100 | <100 | <100 | <100 |
|  | 16 wks | 25,600 | 6,400 | 3,200 | 3,200 | 6,400 | 800 |
| 9141 | Preimmune | <100 | <100 | <100 | <100 | <100 | <100 |
|  | 16 wks | 51,200 | 1,600 | 3,200 | 800 | 3,200 | 800 |
| 9142 | Preimmune | <100 | <100 | <100 | <100 | <100 | <100 |
|  | 16 wks | 25,600 | 1,600 | 3,200 | 400 | 1,600 | 800 |

ELISA titer against:

TABLE 3

Opsonic antibodies evoked in rabbits by SM24-M5-M6 hybrid M proteins

| Antisera | Type 24 streptococci | Type 5 streptococci | Type 6 streptococci |
|---|---|---|---|
| Preimmune pool | 2 | 8 | 6 |
| 9140 | 94 | 70 | 4 |
| 9141 | 84 | 24 | 4 |
| 9142 | 58 | 10 | 4 |
| Anti pep M24 | 98 | N.D. | N.D. |
| Anti pep M5 | N.D. | 96 | N.D. |
| Anti pep M6 | N.D. | N.D. | 94 |

Percent opsonization of:

BIBLIOGRAPHIES

1. ATCC Catalogue of Bacterial & Bacteriophages, Editors, Gherna et al., 17th Ed. (1989).
2. ATCC Catalogue of Yeasts, Editors, Jong et al., 18th Ed. (1990).
3. ATCC Catalogue of Recombinant DNA Materials, Edited Maglott et al., 2nd Ed. (1991).
4. Baird, R. W. et al., Epitopes of Group A Streptococcal M Protein Shared with Antigens of Articular Cartilage and Synovium, J. Immunol., 146, 1191–1202 (1991).
5. Beachey, E. H. et al., Peptic Digestion of Streptococcal M Protein. II. Extraction of M Antigen from Group A Streptococci With Pepsin, Infec. Immun., 9, 891–896 (1974).
6. Beachey, E. H., et al., Purification and Properties of M Protein Extracted from Group A Streptococci with Pepsin: Covalent Structure of the Amino Terminal Region of the Type 24 M Antigen, J. Exp. Med., 145, 1469 (1977).
7. Beachey, E. H., et al., Repeating Covalent Structure of Streptococcal M Protein, Proc. Natl. Acad. Sci. USA, 75, 3163–3167 (1978).
8. Beachey, E. H., et al., Type-Specific Protective immunity Evoked by Synthetic Peptide of Streptococcus pyogenes M Protein, Nature (London), 292, 457–459 (1981).
9. Beachey, E. H. and Sever, J. M., Protective and Nonprotective Epitopes of Chemically Synthesized Peptides of the NH2-Terminal Region of Type 6 Streptococcal M Protein, J. Immunol., 136, 2287–2292 (1986).
10. Beachey et al., Protective Immunogenicity and T Lymphocyte Specificity of a Trivalent Hybrid Peptide containing NH2-terminal Sequences of Types 5, 6 and 24 M Proteins Synthesized in Tandem, J. Exp. Med., 166, 647 (1987)
11. Bisno, A. L., The Concept of Rheumatogenic and Non-Rheumatogenic Group A Streptococci. In Reed, S. E. and J. B. Zabrisikie (eds.) Streptococcal Diseases and the Immune Response, New York, Academic Press, 789–803.
12. Bronze, M. S., et al., Protective and Heat-Crossreactive Epitopes Located within the N-Terminus of Type 19 Streptococcal M Protein, J. Exp. Med., 167, 1849–1859 (1988).
13. Cunningham, M. W., et al., Human and Murine Antibodies Cross-Reactive with Streptococcal M Protein and Myosin Recognize the Sequence GLN-LYS-SER-LYS-GLN in M Protein, J. Immunol., 143, 2677 (1989).
14. Current Protocols in Molecular Biology, Edited by Ausubel, et al., Greene Associates and Wiley-Interscience (Publishers) (1987–88), Vols. 1 and 2.
15. Current Protocols in Immunology, Edited by (Coligan et al., Greene Associates and Wiley-Interscience (Publishers) (1991), Vol. 1.
16. Dale, J.B., et al., Heterogeneity of Type-Specific and Cross-Reactive Antigenic Determinants within a Single M Protein of Group A Streptococci, J. Exp. Med., 151, 1026 (1980).
17. Dale et al., Type-Specific Immunogenicity of a Chemically Synthesized Peptide fragment of Type 5 Streptococcal M Protein J. Exp. Med., 158, 1727 (1983).
18. Dale, J. B. and Beachey, E. H., Multiple Heart-Cross-Reactive Epitopes of Streptococcal M Proteins, J. Exp Med., 161, 113–122 (1985).
19. Dale, J. B. and Beachey, E. H., Epitopes of Streptococcal M Proteins Shared with Cardiac Myosin, J. Exp. Med., 162, 583–591 (1985).
20. Dale, J. B. and Beachey, E. H., Sequence of Myosin-Cross-Reactive Epitopes of Streptococcal M Protein, J. Exp. Med., 164, 1785–1790 (1986).
21. Dale, J. B. and Beachey, E. H., Localization of Protective Epitopes of the Amino Terminus of Type 5 Streptococcal M Protein, J. Exp. Med., 163, 1191–1202 (1986).
22. Fischetti, V. A., Streptococcal M Protein, Scientific American (1991).
23. Fischetti, et al., Surface Proteins from Gram-Positive Cocci Share Unique Structural Features, Persiective on Streptococci and Streptococcal Infections (G. Orefici, Editor), Gustave and Jena (Publishers) 1992.
24. Freimer and McCarty, Rheumatic Fever, Scientific American (December 165).
25. Guthrie & Fink, Guide to Yeast Genetics and Molecular Biology, Methods in Enzymology, Academic Press (1991).
26. Hollingshead, S. K. et al., Complete Nucleotide Sequence of Type 6M Protein of the Group A Streptococcus. Repetitive Structure and Membrane Anchor, *J. Biol. Chem.*, 261, 1677 (1986).
27. IBI Catalog, Kodak. 1990.
28. Innis, M. A., et al., PCR Protocols (eds.), San Diego, Calif., Academic Press (1990).
29. Inouye, M., Experimental Manipulation of Gene Expression, Academic Press, 100–104 (1983).
30. Jones, K. F. and Fischetti, V. A., The importance of the Location of Antibody Binding on the M6 Protein for Opsonization and Phagocytosis of Group A M6 Streptococci, *J. Exp. Med.*, 167, 1114 (1988).
31. Kraus et al., Sequence and Type-Specific Immunogenicity of the Amino-Terminal Region of Type 1 Streptococcal M Protein, *The Journal of Immunology*, 130, 3084–3090 (November 1987)
32. Lancefield, R. C., Current Knowledge of the Type-Specific M Antigens of Group A Streptococci, *J. Immunol.*, 89, 307 (1962).
33. Lancefield. R. C., Persistence of Type-Specific Antibodies in Man Following Infection with Group A Streptococci. *J. Exp. Med.*, 110, 271 (1950).
34. Miller, L., et al., Antigenic Variation Among Group A Streptococcal M Proteins: Nucleotide Sequence of the Serotype 5M Protein Gene and its relationship with Genes Encoding Types 1, 6 and 24 M Proteins, *J. Biol. Chem.*, 263, 5668 (1988).
35. Mouw, A. R., et al., Molecular Evolution of Streptococcal M Protein: Cloning and Nucleotide Sequence of the type 24 M Protein Gene and Relation to Other Genes of *Streptococcus pyogenes, J. Bacteriol.*, 170, 676 (1988).
36. Podbielski et al., Application of the Polymerase Chain Reaction to Study the M Protein(-like) Gene Family in Beta-Hemolytic Streptococci, *Med. Microbiol. Immunol.*, 180, 213 (1991)
37. Robbins et al., *Streptococcus Pyogenes* Type 12 Protein Gene Regulation by Upstream Sequences, *Journal of Bacteriology*, 5633–5640 (December 1987)
38. Sambrook, J., et al., Molecular Cloning: iA Laboratory Manual. Cold Spring Harbor Laboratory, Cold Spring Harbor, N.Y., (eds.) 1989.
39. Sanger et al., DNA Sequencing with Chain-Terminating Inhibitors, *Proc. Natl. Acad. Sci. USA*, 74, 5463 (1977).
40. Sargent, S. J., et al., Sequence of Protective Epitopes of Streptococcal M Proteins Shared with Cardiac Sarcolemmal Membranes, *J. Immunol.*, 139, 1285–1290 (1987).
41. Stollerman, Rheumatic Fever and Streptococcal Infection, Grune & Stratton (1975).
42. Watson, *Molecular Biology of the Gene*, 3rd Ed., W. A. Benjamin, Inc.
43. U.S. Pat. No. 4,284,537 Beachey, (Aug. 18, 1991).
44. U.S. Pat. No. 4,454,121 Beachey, (Jun. 12, 1984).
45. U.S. Pat. No. 4,521 334 Beachey, (Jun. 4, 1985).
46. U.S. Pat. No. 4,597,967 Beachey, (Jul. 1, 1986).
47. U.S. Pat. No. 4,919,930 Beachey et al., (Apr. 24, 1990).
48. U.S. Pat. No. 4,705,684 Beachey, (Nov. 10, 1987).
49. U.S. Pat. No. 5,124,153 to Beachey et al. (1992)

We claim:

1. An immunogenic recombinant multivalent hybrid M protein which comprises amino-terminal peptide fragments of streptococcal M protein that elicit opsonic antibodies against multiple serotypes of Group A streptococci, said protein not eliciting tissue cross-reactive antibodies, wherein at least one of said serotypes is M1.

2. An immunogenic recombinant multivalent hybrid M protein which comprises amino-terminal peptide fragments of streptococcal M protein that elicit opsonic antibodies against multiple serotypes of Group A streptococci, said protein not eliciting tissue cross-reactive antibodies wherein at least one of said serotypes is M3.

3. An immunogenic recombinant multivalent hybrid M protein which comprises amino-terminal peptide fragments of streptococcal M protein that elicit opsonic antibodies against multiple serotypes of Group A streptococci, said protein not eliciting tissue cross-reactive antibodies, wherein at least one of said serotypes is M18.

4. An immunogenic recombinant multivalent hybrid M protein which comprises amino-terminal peptide fragments of streptococcal M protein that elicit opsonic antibodies against multiple serotypes of Group A streptococci, said protein not eliciting tissue cross-reactive antibodies, wherein at least one of said serotypes is M19.

5. An immunogenic recombinant multivalent hybrid M protein according to any one of claims 1 to 4, further comprising a peptide fragment of serotype M2.

6. An immunogenic recombinant multivalent hybrid M protein according to any one of claims 1 to 4, further comprising a peptide fragment of serotype M5.

7. An immunogenic recombinant multivalent hybrid M protein according to any one of claims 1 to 4, further comprising a peptide fragment of serotype M6.

8. An immunogenic recombinant multivalent hybrid M protein according to any one of claims 1 to 4, further comprising at peptide fragment of serotype M12.

9. An immunogenic recombinant multivalent hybrid M protein according to any one of claims 1 to 4, further comprising a peptide fragment of serotype M24.

10. The immunogenic multivalent hybrid M protein of any one of claims 1 to 4, which hybrid M protein also elicits mucosal antibodies.

11. The immunogenic multivalent hybrid M protein of any one of claims 1 to 4, which is trivalent.

12. The immunogenic multivalent hybrid M protein of any one of claims 1 to 4, which is tetravalent.

13. The immunogenic multivalent hybrid M protein of any one of claims 1 to 4, which is octavalent.

14. The immunogenic multivalent hybrid M protein of any one of claims 1 to 4 wherein peptide fragments are fused to each other by a linker comprising amino acids.

15. The recombinant multivalent hybrid M protein of claim 14 wherein the linkers of the amino acids are selected from the group consisting of Arg, Ser, Val, Asp, Pro, and Trp.

16. A composition, comprising a pharmaceutically acceptable carrier and the protein according to any one of claims 1 to 4.

17. A method for immunizing a mammal against streptococci infections, comprising administering to a mammal an immunogenic multivalent hybrid M protein according to any one of claims 1 to 4 in an amount effective to confer immunity against group A streptococci infections.

18. The method according to claim 17 wherein at least one of said serotypes is M1.

19. The method according to claim 17 wherein at least one of said serotypes is M3.

20. The method according to claim 17 wherein at least one of said serotypes is M18.

21. The method according to claim 17 wherein at least one of said serotypes is M19.

22. The method according to claim 17 wherein said multivalent hybrid M protein further comprises a peptide fragment of serotype M2.

23. The method according to claim 17 wherein said multivalent hybrid M protein further comprises a peptide fragment of serotype M5.

24. The method according to claim 17 wherein said multivalent hybrid M protein further comprises a peptide fragment of serotype M6.

25. The method according to claim 17 wherein said multivalent hybrid M protein further comprises a peptide fragment of serotype M12.

26. The method according to claim 17 wherein said multivalent hybrid M protein further comprises a peptide fragment of serotype M24.

27. The method according to claim 17 wherein said multivalent hybrid M protein elicits mucosal antibodies.

28. The method according to claim 17 wherein said multivalent hybrid M protein is trivalent.

29. The method according to claim 17 wherein said multivalent hybrid M protein is tetravalent.

30. The method according to claim 17 wherein said multivalent hybrid M protein is octavalent.

31. The method according to claim 17 wherein said multivalent hybrid M protein wherein peptide fragments are fused to each other by a linker comprising amino acids.

32. The method according to claim 31 wherein said linkers are amino acids are selected from the group consisting of Arg, Ser, Val, Asp, Pro, and Trp.

33. A recombinant DNA molecule, comprising a nucleotide sequence that encodes a multivalent hybrid M protein according to any one of claims 1 to 4.

34. The recombinant DNA molecule according to claim 33 wherein at least one of said serotypes is M1.

35. The recombinant DNA molecule according to claim 33 wherein at least one of said serotypes is M3.

36. The recombinant DNA molecule according to claim 33 wherein at least one of said serotypes is M18.

37. The recombinant DNA molecule according to claim 33 wherein at least one of said serotypes is M19.

38. The recombinant DNA molecule according to claim 33, wherein said hybrid M protein further comprises a peptide fragment of serotype M2.

39. The recombinant DNA molecule according to claim 33, wherein said hybrid M protein further comprises a peptide fragment of serotype M5.

40. The recombinant DNA molecule according to claim 33, wherein said hybrid M protein further comprises a peptide fragment of serotype M6.

41. The recombinant DNA molecule according to claim 33, wherein said hybrid M protein further comprises a peptide fragment of serotype M12.

42. The recombinant DNA molecule according to claim 33, wherein said hybrid M protein further comprises a peptide fragment of serotype M24.

43. The recombinant DNA molecule according to claim 33 which encodes a hybrid M protein that elicits mucosal antibodies.

44. The recombinant DNA molecule according to claim 33 which encodes a tetravalent hybrid M protein.

45. The recombinant DNA molecule according to claim 33 which encodes an octavalent hybrid M protein.

46. The recombinant DNA molecule according to claim 33 which encodes a multivalent hybrid M protein comprising amino-terminal peptide fragments of streptococcal M protein that are fused to each other by a linker comprising amino acids.

47. The recombinant DNA molecule according to claim 46 wherein said amino acids are selected from the group consisting of Arg, Ser, Val, Asp, Pro, and Trp.

* * * * *

UNITED STATES PATENT AND TRADEMARK OFFICE
CERTIFICATE OF CORRECTION

PATENT NO. : 6,063,386
DATED : May 16, 2000
INVENTOR(S) : James B. Dale and Jame W. Lederer It is certified that error appears in the above-indentified patent and that said Letters Patent is hereby corrected as shown below:

Claim 2, column 72, line 1, "antibodies wherein" should read --antibodies, wherein--.
Claim 8, column 72, line 25, "comprising at peptide" should read --comprising a peptide--.

Signed and Sealed this

Twentieth Day of March, 2001

*Attest:*

NICHOLAS P. GODICI

*Attesting Officer*   *Acting Director of the United States Patent and Trademark Office*